United States Patent
Routier et al.

(10) Patent No.: US 9,908,863 B2
(45) Date of Patent: Mar. 6, 2018

(54) PIPERIDINYLCARBAZOLES

(71) Applicant: Merck Patent GmbH, Darmstadt (DE)

(72) Inventors: Julie Routier, Ferney-Voltaire (FR); Thomas Spangenberg, Geneva (CH)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/760,336

(22) PCT Filed: Dec. 27, 2013

(86) PCT No.: PCT/EP2013/003945
§ 371 (c)(1),
(2) Date: Jul. 10, 2015

(87) PCT Pub. No.: WO2014/108168
PCT Pub. Date: Jul. 17, 2014

(65) Prior Publication Data
US 2015/0368226 A1    Dec. 24, 2015

(30) Foreign Application Priority Data

Jan. 10, 2013 (EP) .................... 13150827

(51) Int. Cl.
| | |
|---|---|
| *C07D 401/04* | (2006.01) |
| *A61K 31/454* | (2006.01) |
| *A61K 31/4545* | (2006.01) |
| *C07D 471/04* | (2006.01) |

(52) U.S. Cl.
CPC .......... *C07D 401/04* (2013.01); *A61K 31/454* (2013.01); *A61K 31/4545* (2013.01); *C07D 471/04* (2013.01)

(58) Field of Classification Search
CPC . C07D 401/04; A61K 31/454; A61K 31/4545
USPC ........................................... 546/79
See application file for complete search history.

(56) References Cited

U.S. PATENT DOCUMENTS

| | | |
|---|---|---|
| 2011/0166169 A1 | 7/2011 | Ruxer et al. |
| 2012/0252740 A1 | 10/2012 | Kozikowski et al. |
| 2013/0281484 A1 | 10/2013 | Kozikowski et al. |

FOREIGN PATENT DOCUMENTS

| | | | |
|---|---|---|---|
| GB | 809488 | * | 2/1959 |
| WO | WO 2009/122034 A2 | | 10/2009 |
| WO | WO 2011/011186 A2 | | 1/2011 |

OTHER PUBLICATIONS

Molecular Variations based on Isosteric Replacements Wermuth, 1996, XP-002190259.*
Fluorinated Pharmaceutical, Dr. Basil Wakefield, 2016.*
International Search Report dated Mar. 5, 2014, in PCT/EP2013/003945, filed Dec. 27, 2013.
Otto Nieschulz, et al. "Pharmacological studies on some N-(alkylpiperidyl)carbazole derivatives", Arzneimittel Forschung, Drug Research, vol. 9, Jan. 1, 1959, XP 009167812, pp. 219-228.

* cited by examiner

*Primary Examiner* — Rita J Desai
(74) *Attorney, Agent, or Firm* — Grüneberg and Myers PLLC

(57) ABSTRACT

The present invention provides compounds of Formula (I) for the treatment of parasitic diseases including malaria, as well as neurodegenerative diseases. Formula (I) wherein $R^3$, $R^4$, X and Y have the meaning given in claim 1.

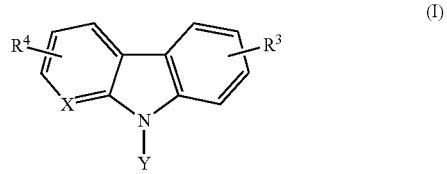

16 Claims, No Drawings

PIPERIDINYLCARBAZOLES

The present invention is applied to the pharmaceutical area for the production of antiparasitic compounds. More particularly, the present invention provides compounds of formula I, their use in the treatment of parasitic diseases including malaria, cerebral malaria and HAT (Human African Trypanosomiasis).

BACKGROUND

Malaria constitutes one of the most devastating global health problems in human history. Infection with malarial parasites affects more than 207 million people annually, killing ~627,000 children. (World Malaria Report 2013). The pathogenesis of malaria is multifactorial, and serious sequalae can result from three primary pathophysiological events: (i) red blood cell destruction; (ii) adhesion of infected erythrocytes to the capillary veins; and (iii) an excessive pro-inflammatory response. Excessive pro-inflammatory response is responsible for sepsis-like signs and symptoms such as rigors, headache, chills, spiking fever, sweating, vasodilatation and hypoglycemia. (Clark et al. Malaria Journal 5 (2006); Stevenson et al. Nat. Rev. Immunol. 4:169-180 (2004) and Schofield et al. Nature Reviews Immunology 5:722-735 (2005)). Cerebral malaria is a severe neurological complication of malarial infection and is a major cause of acute non-traumatic encephalopathy in tropical countries. (Idro et al. Lancet Neurol. 4: 827-840 (2005)).

*P. falciparum* is the species responsible for the most lethal form of such disease (Garcia C R S, Azevedo M F, Wunderlich G, Budu A, Young J and Bannister L. G (2008) *Plasmodium* in the Post Genome Era: New insights into the molecular cell biology of the malaria parasites. International Review of Molecular and Cell Biology 266: 85-156). Despite of countless efforts towards the malaria control, the number of cases continues to increase due to arising of parasites resistant to most available antimalaricals, as well as insecticides-resistant mosquitoes, which makes necessary to develop alternative strategies to eradicate such disease. In this sense, one of the huge obstacles is the complexity of malaria parasites and their interactions with the human host and vector-insect. Life-cycle of malaria parasite: parasite-host interactions Asexual cycle of *P. falciparum* occurs in human host, and the infection begins with the bite of female anopheles mosquito, which injects sporozoites with saliva. Recently, it was proven that firstly injected sporozoites cross through dermis and only a few of them go into the capillary vessels, while others go into lymph vessels and originate exoerythrocytic forms unknown until then, which may have an important influence on host immunological system (Amino R, Thiberge S, Martin B, Celli S, Shorte S, Frischknecht F & Menard R (2006) Quantitative imaging of *Plasmodium* transmission from mosquito to mammal. Nat Med 12: 220-224). Once in the bloodstream, sporozoites invade hepatocytes and develop themselves in exoerythrocytic forms, which rupture the cells releasing merozoites in the blood (Mota M M, Pradel G, Vanderberg J P, Hafalla J C R, Frevert U, Nussenzweig R S, Nussenzweig V & Rodriguez A (2001) Migration of *Plasmodium* sporozoites through cells before infection). Merozoites invade erythrocytes and develop themselves inside the parasitophorous vacuoles, suffering several biochemical and morphological changes that may basically be identified by three stages known as ring, trophozoite and schizont. Erythrocyte rupture releases merozoites allowing continuity of intraerythrocytic cycle (Bannister L H, Hopkins J M, Fowler R E, Krishna S & Mitchell G H (2000) A brief illustrated guide to the ultrastucture of *Plasmodium falciparum* asexual blood stages. Parasitol Today 16: 427-433).

Some parasites in bloodstream develop into gametocytes, which are the infective form for the vector mosquito, where the sexual cycle occurs. In the mosquito bowel occurs the maturation of gametocytes, a process known as gametogenesis, which is followed by fertilization, with the union of male and female gametes originating a zygote. This zygote migrates and adheres to the bowel epithelium, where it develops into an oocyst. When oocyst ruptures, it releases sporozoites which go to the salivary gland and are released during mosquito feeding (Ghosh A, Edwards M J & Jacobs-Lorena M (2000) The journey of the malaria parasite into the mosquito: Hopes for the new century. Parasitol Today 16: 196-201).

Besides the great variety of parasite forms in the host and vector mosquito, a noticeable feature of the life cycle of several species of *Plasmodium* is its synchronization and periodicity. Such distinguished periodicity in formation of gametocytes, the sexual forms of parasite, have been observed since the beginning of last century, and all research done with several species of *Plasmodium* show the existence of a gametocyte production peak at night, every 24 hours, usually at the same time of mosquito feeding. In this way, the gametocytes circadian rhythm must be an important adaptation for maintenance of parasite sexual cycle in the vector mosquito (Garcia C R S, Markus R P & Madeira L (2001) Tertian and quartan fevers: temporal regulation in malarial infection. J Biol Rhythms 16: 436-443). Until now the signal responsible for inducing gametocytes formation in the vertebrate host bloodstream was not identified.

Regarding asexual forms, the high synchronization of Intraerythrocytic stages results in recurring fever attacks and shivers, always in periods of time multiple of 24 hours, coinciding with a practically simultaneously release of billion of merozoites in bloodstream.

Natural carbazol alkaloids have been used for the treatment of malaria in folklore medicine (Heterocycles, Vol 79, 2009, pages 121-144).

Calothrixins A and B have potential antimalarial effect (Tetrahedron 55 (1999) 13513-13520).

Carbazol derivatives have been synthesized to inhibit the *Plasmodium falciparum* pyrimidine biosynthetic enzyme (J. Med. Chem., 2007, 50, 186-191).

Other carbazole derivatives have been disclosed in WO0129028, WO2010/010027, WO2007/062399, WO2005/074971 and WO02/060867.

It is an object of the present invention to provide N-substituted carbazoles that are useful to treat malaria and other parasitic diseases.

Particularly, the present invention provides compounds of Formula (I)

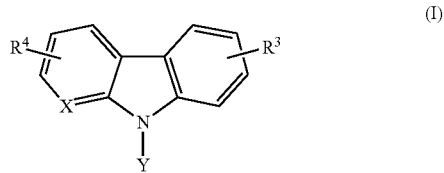

wherein
Y is a group selected from

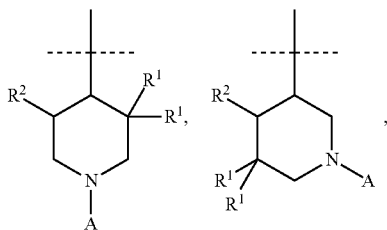

R¹ denotes H or F,
R² denotes OH or F,
X denotes CH or N,
R³ and R⁴ independently of one another denote H, Hal or OA, CHal₃Hal is F, Cl, Br or I,
A denotes H or Alk,
Alk is a branched or linear alkyl group having 1 to 8 carbon atoms or cycloalkyl having 3 to 6 carbon atoms, wherein 1 to 7H-atoms may be independently replaced by Hal, OR, COOR, CN, NR₂, phenyl, linear or branched alkyl having 1, 2 or 3 C atoms, cycloalkyl having 3 to 6 carbon atoms and/or wherein 1 to 3 CH₂-groups may be replaced by O, —NRCO—, —CO—, —COO—, —CONR, —NR— or S, or cycloalkyl having 3 to 6 carbon atoms,
and
R is H or is a branched or linear alkyl group having 1 to 8 carbon atoms,
as well as the pharmaceutically acceptable salts esters and N-oxides thereof, in a racemic form or in an enantiomerically pure form or enriched mixture of the respective enantiomers in all ratios, and/or as a mixture of diastereoisomers in all ratios.

When a group R, R¹, R², R³, R⁴X, Hal, A or Alk is present more than once in a compound of the present invention, each group independently denotes one of the meanings given in its definition.

In preferred embodiments the relative stereoconfiguration of R² and its adjacent ring substituent is trans. However, cis configuration is also possible. In case R² is Hal, and particularly in case R² is F the relative stereoconfiguration of R² and its adjacent ring substituent is preferably cis.

The invention also relates to the preferred compounds IA and its enantiomers:

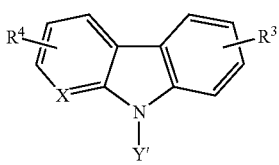

(IA)

wherein
Y' is a group selected from

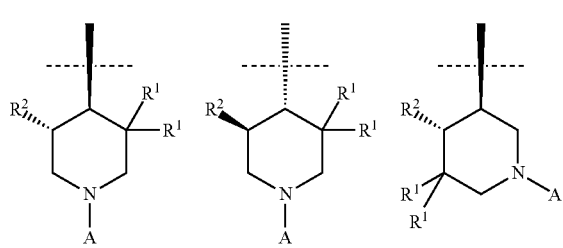

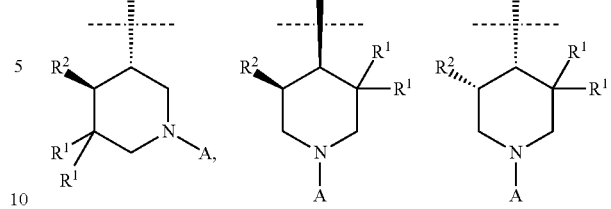

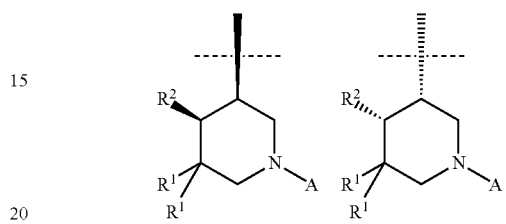

R² is OH or F
And R¹R³, R⁴, X and A are as defined above.
Moreover, compounds of fomula I' are preferred:

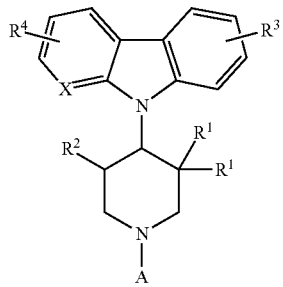

(I')

More preferred are compounds of formula I, IA and I', wherein R² is OH, compounds of formula I and I', wherein R' is H, compounds of formula I, IA and I', wherein A is H, compounds of formula I, IA and I', wherein R³ and R⁴ are both Cl, CF₃ or both F, compounds of formula I, IA and I', wherein R³ is Cl and R⁴ is F or wherein R³ is F and R⁴ is Cl.

Compounds of formula I, IA and I' wherein the group CR¹R¹ denotes CH₂ or CF₂

Most preferred are compounds of formula I, IA and I' wherein X is CH.

Alk is also preferably cycloalkyl having 3 to 6 carbon atoms, such as cyclopentyl or cyclohexyl, COR or COOR, wherein R has the meaning given above.

R² is preferably OH.

Other preferred embodiments are compounds wherein R³ and R⁴ are both Cl or both F or both CF₃ or both CCl₃.

A is preferably a linear or branched alkyl group wherein 1, 2, 3, 4 or 5 H atoms are replaced by Hal, methyl and/or wherein one CH₂-group is replaced by cyclopropyl.

Particular preferred compounds of formula I are compounds 1 to 70 listed below ("ABS" indicates an enantiopure form and "RAC" indicates a racemic mixture):

| Compound no. | Structure |
|---|---|
| 1 | 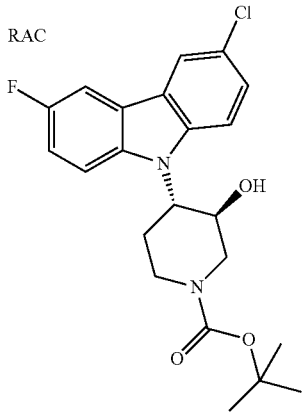 [SMILES: CC(C)(C)OC(=O)N1CC[C@H](n2c3ccc(F)cc3c3cc(Cl)ccc32)[C@@H](O)C1] |
| 2 | 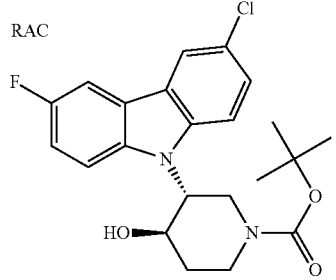 [SMILES: CC(C)(C)OC(=O)N1CC[C@@H](O)[C@H](n2c3ccc(F)cc3c3cc(Cl)ccc32)C1] |
| 3 | 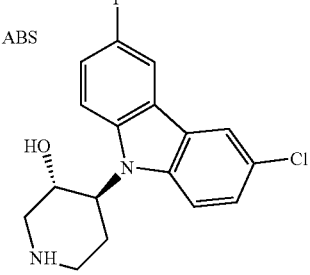 |
| 4 | 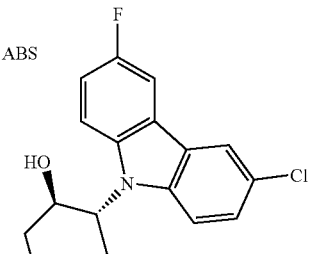 |
| 5 | 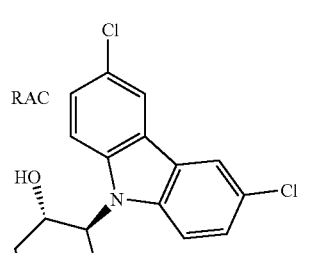 |
-continued
| Compound no. | Structure |
|---|---|
| 6 | 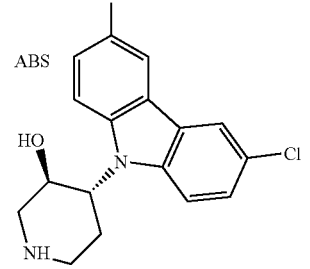 |
| 7 | 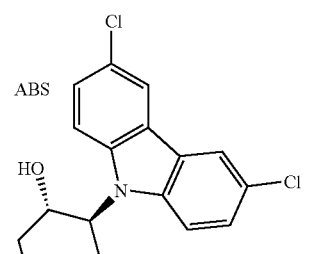 |
| 8 | 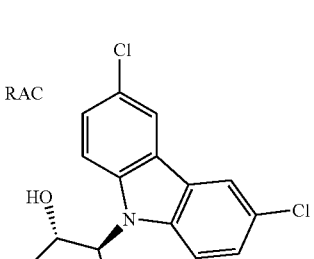 |
| 9 | 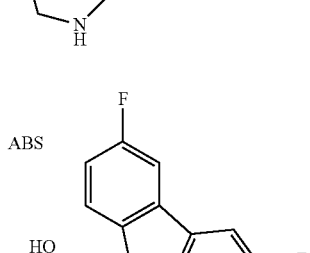 |
| 10 | 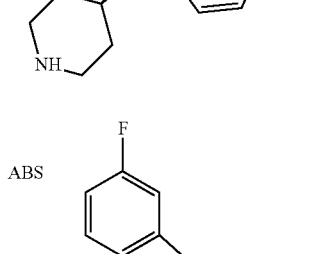 |

TABLE 7-continued
| Compound no. | Structure |
|---|---|
| 11 | 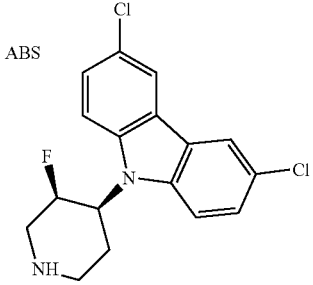 |
| 12 | 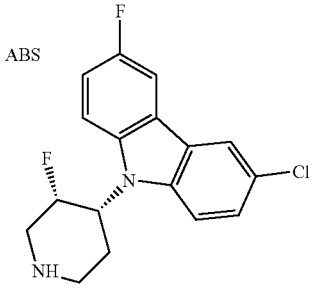 [SMILES: "ABS" ; Fc1ccc2c(c1)c1cc(Cl)ccc1n2[C@@H]1CCNC[C@@H]1F] |
| 13 | 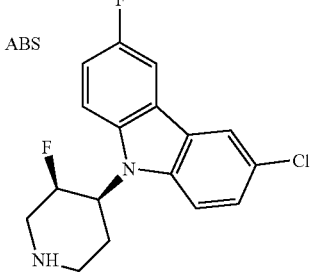 |
| 14 | 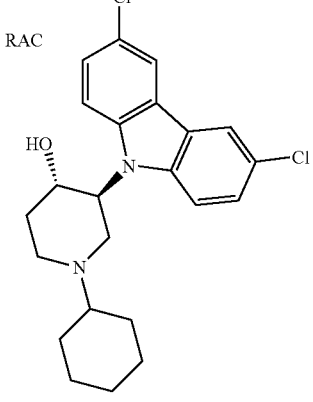 |
| 15 | 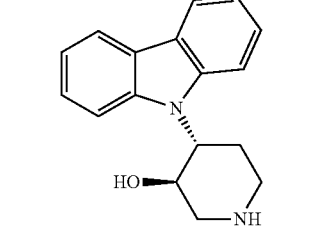 |
TABLE 8-continued
| Compound no. | Structure |
|---|---|
| 16 | 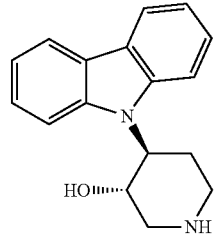 |
| 17 | 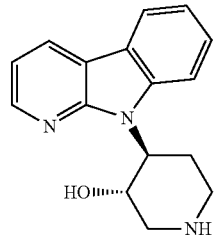 |
| 18 | 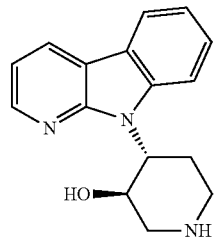 |
| 19 | 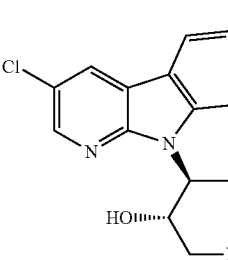 |
| 20 | 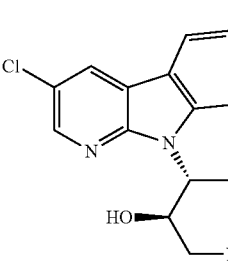 |

-continued
| Compound no. | Structure |
|---|---|
| 21 | 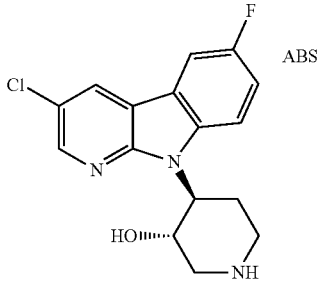 |
| 22 | 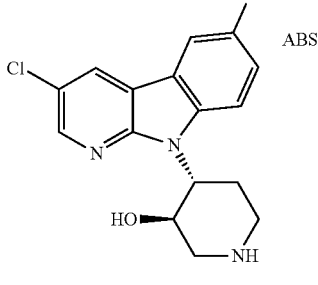 |
| 23 | 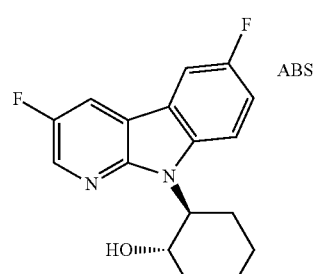 |
| 24 | 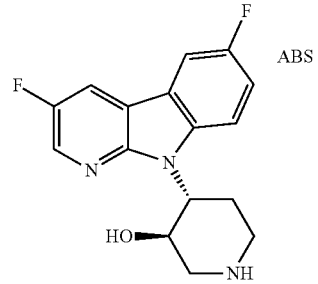 |
| 25 | 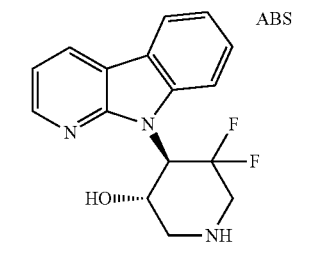 |
-continued
| Compound no. | Structure |
|---|---|
| 26 | 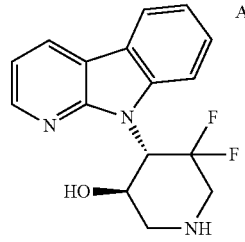 |
| 27 | 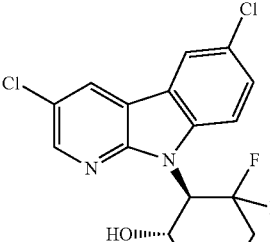 |
| 28 | 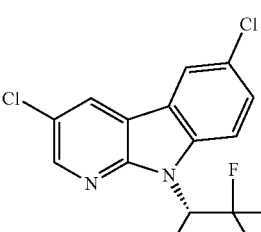 |
| 29 | 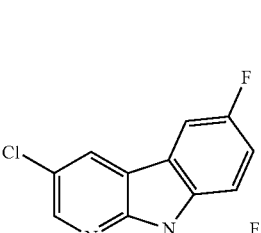 |
| 30 | 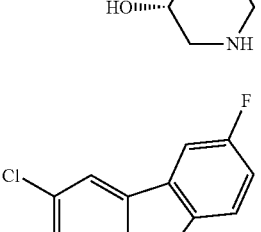 |

-continued
| Compound no. | Structure |
|---|---|
| 31 | 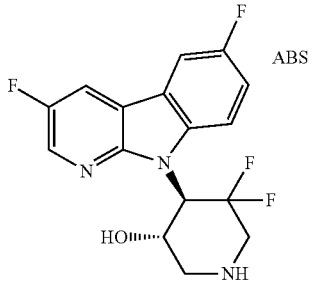 |
| 32 | 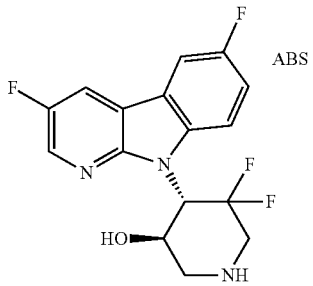 |
| 33 | 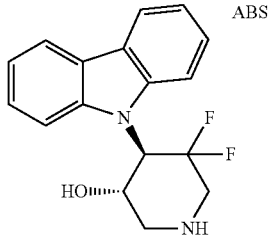 |
| 34 | 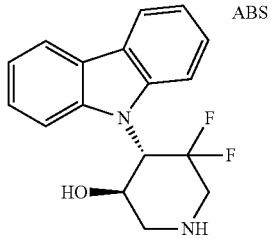 |
| 35 | 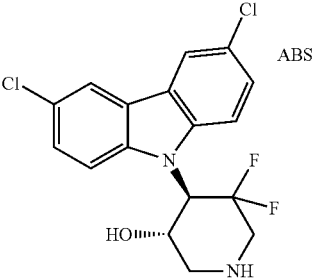 |
-continued
| Compound no. | Structure |
|---|---|
| 36 | 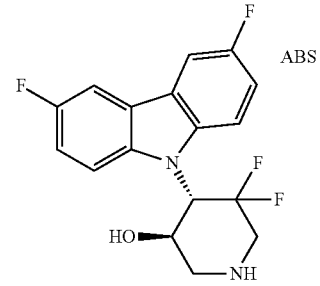 |
| 37 | 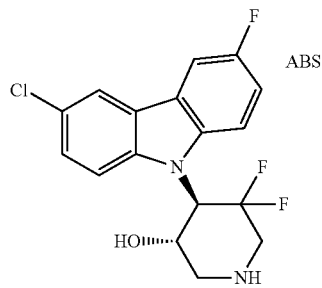 |
| 38 | 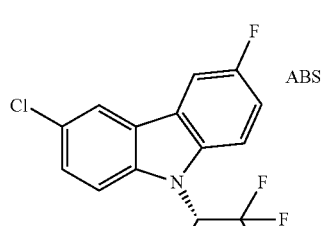 |
| 39 | 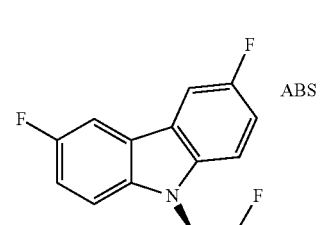 |
| 40 | 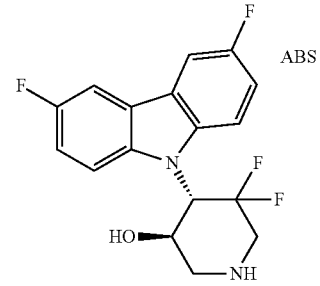 |

-continued

| Compound no. | Structure |
|---|---|
| 41 | RAC; 3,6-difluoro-9-(1-benzylpiperidin-4-yl)-carbazole with OH on piperidine |
| 42 | ABS; 3,6-difluoro-9-(1-benzyl-4-hydroxypiperidin-3-yl)-carbazole |
| 43 | ABS; 3,6-difluoro-9-(1-benzyl-4-hydroxypiperidin-3-yl)-carbazole (enantiomer) |
| 44 | RAC; 3,6-difluoro-9-(1-Boc-4-hydroxypiperidin-3-yl)-carbazole |
| 45 | ABS; 3,6-difluoro-9-[1-(3,3,3-trifluoropropyl)-4-hydroxypiperidin-3-yl]-carbazole |
| 46 | RAC; tert-butyl 4-(3,6-difluorocarbazol-9-yl)-3-hydroxypiperidine-1-carboxylate |
| 47 | ABS; tert-butyl 3-(3,6-difluorocarbazol-9-yl)-4-hydroxypiperidine-1-carboxylate |
| 48 | ABS; tert-butyl 3-(3,6-difluorocarbazol-9-yl)-4-hydroxypiperidine-1-carboxylate (enantiomer) |
| 49 | ABS; 3,6-difluoro-9-[1-(4,4,4-trifluorobutyl)-4-hydroxypiperidin-3-yl]-carbazole |
| 50 | ABS; 3,6-difluoro-9-[1-(cyclopropylmethyl)-4-hydroxypiperidin-3-yl]-carbazole |

-continued

| Compound no. | Structure |
|---|---|
| 51 | ABS (3,6-difluorocarbazole with N-neopentyl-4-hydroxypiperidin-3-yl) |
| 52 | ABS (3,6-difluorocarbazole with N-phenethyl-4-hydroxypiperidin-3-yl) |
| 53 | ABS (3,6-difluorocarbazole with N-(1-(trifluoromethyl)cyclopropyl)methyl-4-hydroxypiperidin-3-yl) |
| 54 | ABS (3,6-dichlorocarbazole with N-(3,3,3-trifluoropropyl)-4-hydroxypiperidin-3-yl) |
| 55 | ABS (3,6-dichloro-α-carboline with 4-hydroxypiperidin-3-yl) |

-continued

| Compound no. | Structure |
|---|---|
| 56 | ABS (3,6-difluoro-α-carboline with 4-hydroxypiperidin-3-yl, NH) |
| 57 | ABS (3,6-dichloro-α-carboline with N-(3,3,3-trifluoropropyl)-4-hydroxypiperidin-3-yl) |
| 58 | ABS (3,6-dichloro-α-carboline with N-(3,3,3-trifluoropropyl)-3-hydroxypiperidin-4-yl) |
| 59 | RAC (3,6-bis(trifluoromethyl)carbazole with 4-hydroxypiperidin-3-yl) |
| 60 | ABS (3,6-bis(trifluoromethyl)carbazole with 3-hydroxypiperidin-4-yl) |

| Compound no. | Structure |
|---|---|
| 61 | ABS, 3,6-bis(trifluoromethyl)carbazole N-substituted with 3-hydroxypiperidin-4-yl |
| 62 | RAC, 3,6-difluorocarbazole N-substituted with 3-hydroxypiperidin-4-yl |
| 63 | RAC, 3,6-difluorocarbazole N-substituted with 1-benzyl-3-hydroxypiperidin-4-yl |
| 64 | RAC, 3,5-dichloro-pyrrolo[2,3-b]pyridine N-substituted with 3-hydroxypiperidin-4-yl |
| 65 | RAC, 3,6-difluorocarbazole N-substituted with 3-hydroxypiperidin-4-yl |
| 66 | ABS, 3,6-dichlorocarbazole N-substituted with 3-hydroxypiperidin-4-yl |
| 67 | ABS, 3,6-dichlorocarbazole N-substituted with 3-hydroxypiperidin-4-yl |
| 68 | RAC, 3,6-bis(trifluoromethyl)carbazole N-substituted with 3-hydroxypiperidin-4-yl |
| 69 | ABS, 3,6-difluorocarbazole N-substituted with 3-hydroxypiperidin-4-yl |
| 70 | ABS, 3,6-difluorocarbazole N-substituted with 3-hydroxypiperidin-4-yl |

The present invention encompasses pure enantiomeres of formula (I) as well mixtures thereof in all ratios.

The present invention encompasses compounds of Formula (I) as well as their use as a medicament (human and veterinary).

Compounds of the present invention can therefore be used in the treatment of disorders associated with apoptosis, including neurodegenerative disorders like Alzheimer's diseases, Parkinson disease, or multiple sclerosis, diseases associated with pyloglutamine tracts, epilepsy, ischemia, infertility, cardiovacular disorders, renal hypoxia, and hepatitis (in humans as well as in other animals).

The present invention also provides the use of compounds of Formula (I) and related Formulae as defined above, in the treatment or prevention of parasitic and infectious diseases (in humans as well as in other animals). Said parasitic and infectious diseases include in particular Malaria, cerebral Malaria, HAT (Human African Trypanosomiasis), tuberculosis, chagas (American Trypanosomiasis), leishmaniasis, onchocerciasis, filariasis, and schistosomiasis.

The parasitic and infectious diseases treated by the compounds of the present invention also embrasses the following: Acanthamoeba Infection, Acanthamoeba Keratitis Infection, Alveolar Echinococcosis (Echinococcosis, Hydatid Disease), Amebiasis (Entamoeba histolytica Infection), Ancylostomiasis (Hookworm, Cutaneous Larva Migrans [CLM]), Angiostrongyliasis (Angiostrongylus Infection), Anisakiasis (Anisakis Infection, Pseudoterranova Infection), Ascariasis (Ascaris Infection, Intestinal tip Roundworms), Babesiosis (Babesia Infection), Balantidiasis (Balantidium Infection), Baylisascariasis (Baylisascaris Infection, Racoon Roundworm), Bilharzia (Schistosomiasis), Blastocystis hominis Infection, Body Lice Infestation (Pediculosis), Capillariasis (Capillaria Infection), Cercarial Dermatitis (Swimmer's Itch), Chilomastix mesnili Infection (Nonpathogenic [Harmless] Intestinal Protozoa), Clonorchiasis (Clonorchis Infection), CLM (Cutaneous Larva Migrans, Ancylostomiasis, Hookworm), "Crabs" (Pubic Lice), Cryptosporidiosis (Cryptosporidium Infection), Cutaneous Larva Migrans (CLM, Ancylostomiasis, Hookworm), Cyclosporiasis (Cyclospora Infection), Cysticercosis (Neurocysticercosis), Cystoisopora Infection (Cystoisosporiasis) formerly Isospora Infection, Diarrhea, Dientamoeba fragilis Infection, Diphyllobothriasis (Diphyllobothrium Infection), Dipylidium caninum Infection (dog or cat tapeworm infection), Dracunculiasis (Guinea Worm Disease), Dog tapeworm (Dipylidium caninum Infection), Echinococcosis (Alveolar Echinococcosis, Hydatid Disease), Elephantiasis (Filariasis, Lymphatic Filariasis), Endolimax nana Infection (Nonpathogenic [Harmless] Intestinal Protozoa), Entamoeba coli Infection (Nonpathogenic [Harmless] Intestinal Protozoa), Entamoeba dispar Infection (Nonpathogenic [Harmless] Intestinal Protozoa), Entamoeba hartmanni Infection (Nonpathogenic [Harmless] Intestinal. Protozoa), Entamoeba histolytica Infection (Amebiasis), Entamoeba polecki, Enterobiasis (Pinworm Infection), Fascioliasis (Fasciola Infection), Fasciolopsiasis (Fasciolopsis Infection), Filariasis (Lymphatic Filariasis, Elephantiasis), Foodborne Diseases, Giardiasis (Giardia Infection), Gnathostomiasis (Gnathostoma Infection), Guinea Worm Disease (Dracunculiasis), Head Lice Infestation (Pediculosis), Heterophyiasis (Heterophyes Infection), Hydatid Disease (Alveolar Echinococcosis), Hymenolepiasis (Hymenolepis Infection), Hookworm Infection (Ancylostomiasis, Cutaneous Larva Migrans [CLM]), Intestinal Roundworms (Ascariasis, Ascaris Infection), Iodamoeba buetschlii Infection (Nonpathogenic [Harmless] Intestinal Protozoa), Isospora Infection (see Cystoisospora Infection), Kala-azar (Leishmaniasis, Leishmania Infection), Keratitis (Acanthamoeba Infection), Leishmaniasis (Kala-azar, Leishmania Infection), Lice Infestation (Body, Head, or Pubic Lice, Pediculosis, Pthiriasis), Loaiasis (Loa loa Infection), Lymphatic filariasis (Filariasis, Elephantiasis), Malaria (Plasmodium Infection), Microsporidiosis (Microsporidia Infection), Mite Infestation (Scabies), Naegleria Infection, Neurocysticercosis (Cysticercosis), Nonpathogenic (Harmless) Intestinal Protozoa, Ocular Larva Migrans (Toxocariasis, Toxocara Infection, Visceral Larva Migrans), Onchocerciasis (River Blindness), Opisthorchiasis (Opisthorchis Infection), Paragonimiasis (Paragonimus Infection), Pediculosis (Head or Body Lice Infestation), Pthiriasis (Pubic Lice Infestation), Pinworm Infection (Enterobiasis), Plasmodium Infection (Malaria), Pneumocystis jirovecii Pneumonia, Pseudoterranova Infection (Anisakiasis, Anisakis Infection), Pubic Lice Infestation ("Crabs," Pthiriasis), Raccoon Roundworm Infection (Baylisascariasis; Baylisascaris Infection), River Blindness (Onchocerciasis), Scabies, Schistosomiasis (Bilharzia), Sleeping Sickness (Trypanosomiasis, African; African Sleeping Sickness), Strongyloidiasis (Strongyloides Infection), Swimmer's Itch (Cercarial Dermatitis), Taeniasis (Taenia Infection, Tapeworm Infection), Tapeworm Infection (Taeniasis, Taenia Infection), Toxocariasis (Toxocara Infection, Ocular Larva Migrans, Visceral Larva Migrans), Toxoplasmosis (Toxoplasma Infection), Travelers' Diarrhea, Trichinellosis (Trichinosis), Trichinosis (Trichinellosis), Trichomoniasis (Trichomonas Infection), Trichuriasis (Whipworm Infection, Trichuris Infection), Trypanosomiasis, African (African Sleeping Sickness, Sleeping Sickness), Visceral Larva Migrans (Toxocariasis, Toxocara Infection, Ocular Larva Migrans), Waterborne Diseases, Whipworm Infection (Trichuriasis, Trichuris Infection), Zoonotic Diseases (Diseases spread from animals to people).

The parasitic and infectious diseases treated by the compounds of the present invention also embrasses particularly: malaria, tuberculosis, African sleeping sickness (HAT), chagas, leishmaniasis, onchocerciasis, filariasis, schistosomiasis, Cryptosporidiosis (Cryptosporidium Infection), Entamoeba coli Infection (Nonpathogenic [Harmless] Intestinal Protozoa), Entamoeba dispar Infection (Nonpathogenic [Harmless] Intestinal Protozoa), Entamoeba hartmanni Infection (Nonpathogenic [Harmless] Intestinal Protozoa), Entamoeba histolytica Infection (Amebiasis), Entamoeba polecki, Toxoplasmosis (Toxoplasma Infection), Zoonotic Diseases (Diseases spread from animals to people).

In another specific embodment, the present invention provides a pharmaceutical composition comprising at least one compound of Formula (I) and related Formulae and/or pharmaceutically usable derivatives, tautomers, salts, solvates and stereoisomers thereof, including mixtures thereof in all ratios, and optionally excipients and/or adjuvants. This pharmaceutical composition might be applied in human medicine as well as in veterinary medicine.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound.

Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinyl-pyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for, extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, solvates and stereoisomers thereof, including mixtures thereof in all ratios, and at least one further medicament active ingredient.

In another specific embodment, the present invention provides a pharmaceutical composition comprising at least one compound of Formula (I) and related Formulae and/or pharmaceutically usable derivatives, tautomers, salts, solvates and stereoisomers thereof, including mixtures thereof in all ratios, and at least one further active ingredient.

In another specific embodiment, the present invention provides a kit consisting of separate packs of (a) an effective amount of a compound of the formula (I) and/or pharmaceutically usable derivatives, solvates and stereoisomers thereof, including mixtures thereof in all ratios, and (b) an effective amount of a further medicament active ingredient.

According to a general process, compounds of formula (I), and any subformulae can be converted to alternative compounds of formula (I) and any subformulae, employing suitable inter-conversion techniques well-known by a person skilled in the art.

In general, the synthesis pathways for any individual compounds of formula (I) and (I') depends on the specific substituents of each molecule, on the availability of intermediates or transformation of commercially available starting materials into key intermediates, such factors being appreciated by the one ordinary skilled in the art. For all the protection and deprotection methods, see Philipp J. Kocienski in "Protecting groups", Georg Thieme Verlag Stuttgart, New York, 1994 and Theodora W. Greene and Peter G. Wuts in "Protective groups in organic synthesis", Wiley Interscience, $3^{rd}$ Edition 1999.

Compounds of general formula (Ia) for which A is Alk, preferentially of trans relative stereochemistry, are obtained by reaction of compounds of general formula (Ic), preferentially of trans relative stereochemistry, with appropriate aldehyde or ketone in reductive amination conditions well known to those skilled in the art, using reducting agent such as but not limited to sodium triacetoxyborohydride, in a solvent such as but not limited to dichloromethane, preferentially at room temperature (scheme 1). In the following schemes 1 to scheme 28 the groups $R^1$, $R^2$, $R^3$, $R^4$, X and A have the meaning given above, whereas PG denotes a protecting group and LG a leaving group.

scheme 1

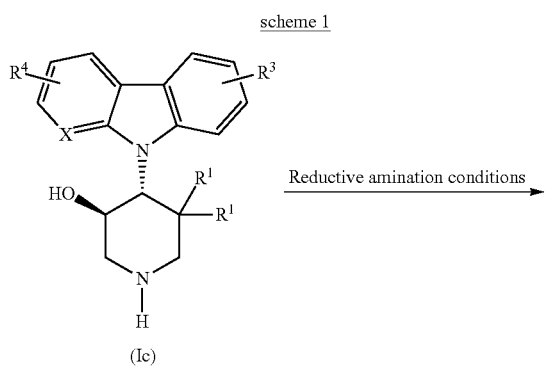

(Ic)

Compounds of general formula (I'a) for which A is Alk, preferentially of relative stereochemistry trans, are obtained by reaction of compounds of general formula (I'c), preferentially of trans relative stereochemistry, with appropriate aldehyde or ketone in reductive amination conditions well known to those skilled in the art, using reducing agent such as but not limited to sodium triacetoxyborohydride, in a solvent such as but not limited to dichloromethane, preferentially at room temperature (scheme 2).

Optically active compounds of formula (Ia) for which A is Alk, preferentially of trans relative stereochemistry, are obtained from reductive amination of optically active compounds of general formula (Ic), preferentially of trans relative stereochemistry, with appropriate aldehyde or ketone in reductive amination conditions well known to those skilled in the art, using reducing agent such as but not limited to sodium triacetoxyborohydride, in a solvent such as but not limited to dichloromethane, preferentially at room temperature (scheme 3).

scheme 3

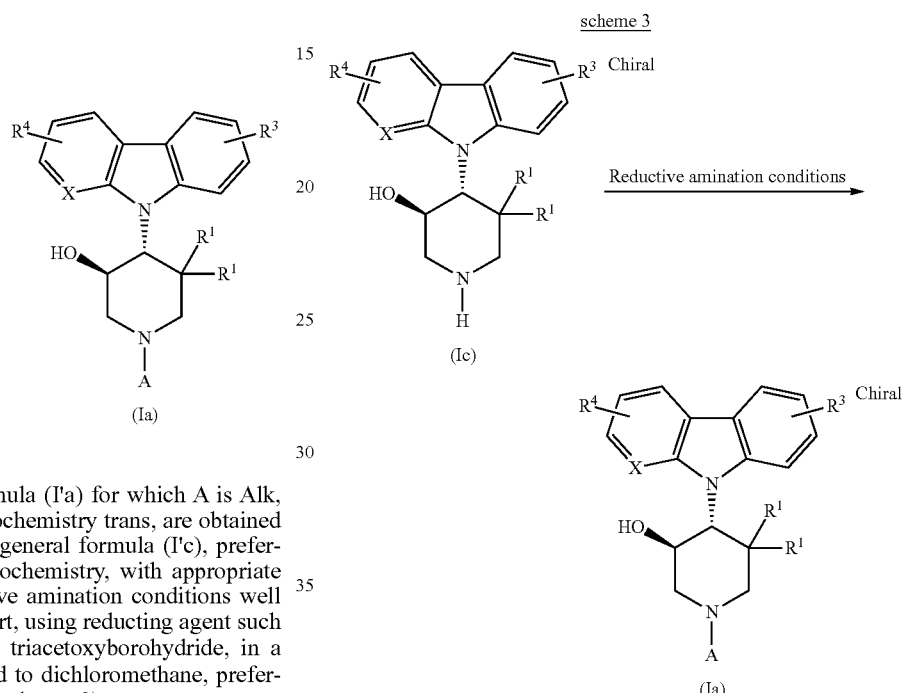

Optically active compounds of formula (I'a) for which A is Alk, preferentially of trans relative stereochemistry, are obtained from reductive amination of optically active compounds of general formula (I'c), preferentially of trans relative stereochemistry, with appropriate aldehyde or ketone in reductive amination conditions well known to those skilled in the art, using reducing agent such as but not limited to sodium triacetoxyborohydride, in a solvent such as but not limited to dichloromethane, preferentially at room temperature (scheme 4).

scheme 2

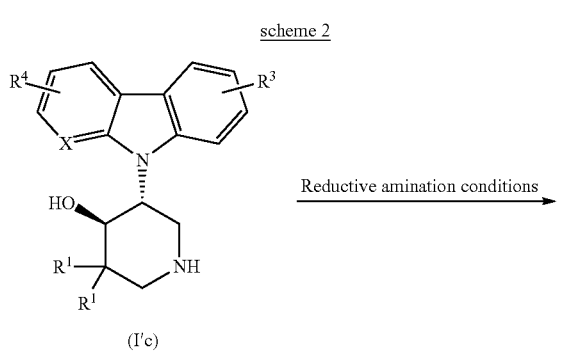

scheme 4

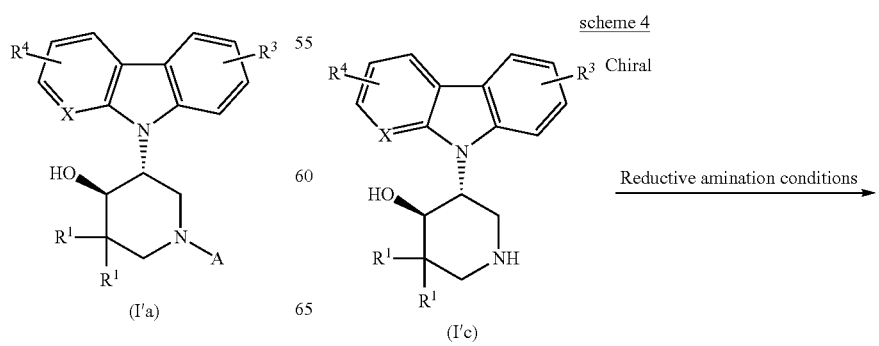

-continued

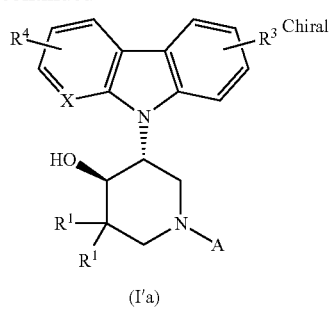

(I'a)

Compounds of general formula (Ib) for which A is Alk, preferentially of cis relative stereochemistry, are obtained by reaction of compounds of general formula (Id), preferentially of cis relative stereochemistry, with appropriate aldehyde or ketone in reductive amination conditions well known to those skilled in the art, using reducing agent such as but not limited to sodium triacetoxyborohydride, in a solvent such as but not limited to dichloromethane, preferentially at room temperature (scheme 5).

scheme 5

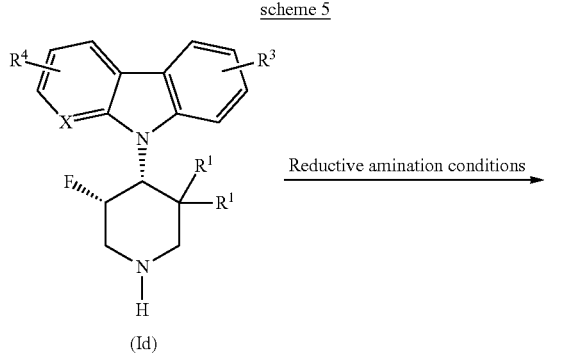

Optically active compounds of formula (Ib) for which A is Alk, preferentially of cis relative stereochemistry, are obtained from reductive amination of optically active compounds of general formula (Id), preferentially of cis relative stereochemistry, with appropriate aldehyde or ketone in reductive amination conditions well known to those skilled in the art, using reducing agent such as but not limited to sodium triacetoxyborohydride, in a solvent such as but not limited to dichloromethane, preferentially at room temperature (scheme 6)

scheme 6

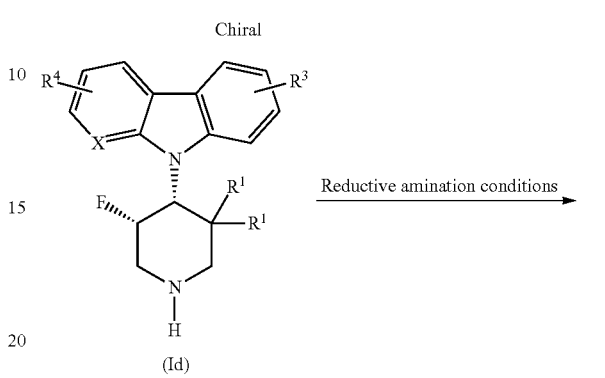

Compounds of general formula (Ic), preferentially of trans relative stereochemistry, are obtained by deprotection of compounds of general formula (IIc), preferentially of trans relative stereochemistry, protected with a protecting group such as but not limited to tert-butylcarbamate, in conditions well known to those skilled in the art (Kocienski P. J., Protecting groups, Georg Thieme Verlag Stuttgart, New York, 1994 and Greene, T. W., Wuts P. G. Protective groups in organic synthesis, Wiley Interscience, 3rd Edition 1999). In a preferred pathway, the protecting group (PG) is cleaved preferentially under acidic conditions, using acid such as but not limited to HCl in a solvent such as but not limited MeOH (scheme 7).

scheme 7

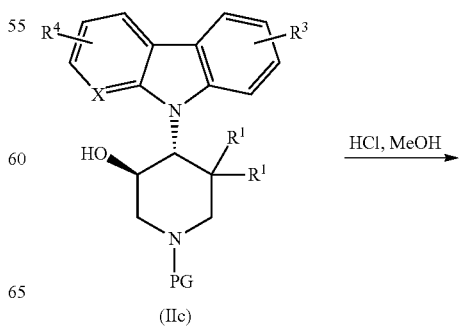

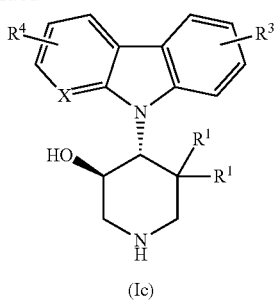

(I'c)

scheme 9

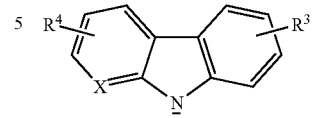

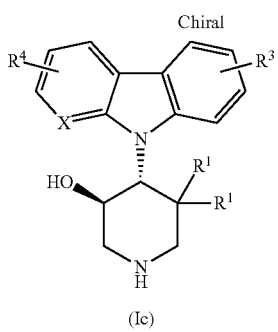

(Ic)

Compounds of general formula (I'c), preferentially of trans relative stereochemistry, are obtained by deprotection of compounds of general formula (II'c), preferentially of trans relative stereochemistry, protected with a protecting group such as but not limited to tert-butylcarbamate, in conditions well known to those skilled in the art (Kocienski P. J., Protecting groups, Georg Thieme Verlag Stuttgart, New York, 1994 and Greene, T. W., Wuts P. G. Protective groups in organic synthesis, Wiley Interscience, $3^{rd}$ Edition 1999). In a preferred pathway, the protecting group (PG) is cleaved preferentially under acidic conditions, using acid such as but not limited to HCl in a solvent such as but not limited MeOH (scheme 8).

Optically active compounds of formula (Ic), preferentially of trans relative stereochemistry, are obtained from deprotection of optically active compounds of formula (II'c), preferentially of trans relative stereochemistry, in conditions adapted to the nature of protecting group used. Typically, if PG is a tert-butoxycarbamate group, the conditions used are preferentially acidic conditions (scheme 10).

scheme 8

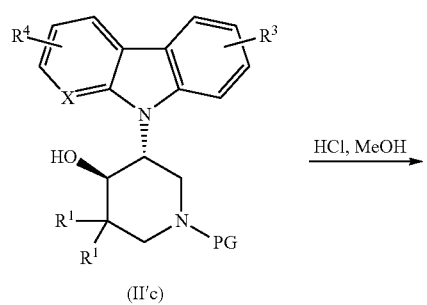

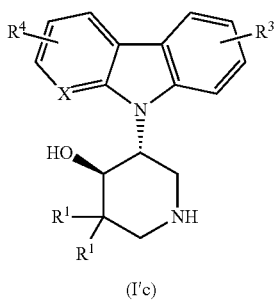

(I'c)

Optically active compounds of formula (Ic), preferentially of trans relative stereochemistry, are obtained from deprotection of optically active compounds of formula (IIe), preferentially of trans relative stereochemistry, in conditions adapted to the nature of protecting group used. Typically, if PG is a tert-butoxycarbamate group, the conditions used are preferentially acidic conditions (scheme 9).

scheme 10

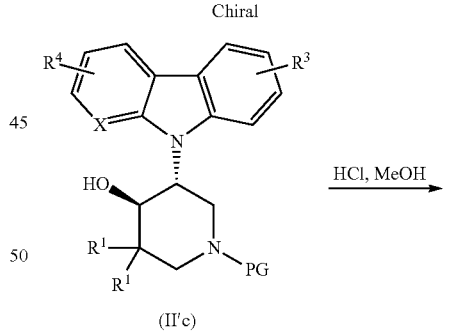

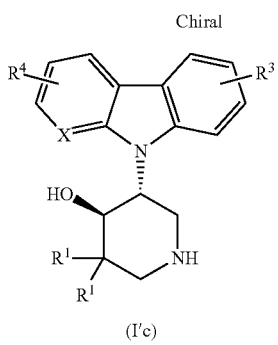

(I'c)

Compounds of general formula (Id), preferentially of cis relative stereochemistry, are obtained by the deprotection of compounds of general formula (IId), preferentially of cis relative stereochemistry, protected with a protecting group such as but not limited to tert-butylcarbamate, in conditions well known to those skilled in the art (Kocienski P. J., Protecting groups, Georg Thieme Verlag Stuttgart, New York, 1994 and Greene, T. W., Wuts P. G. Protective groups in organic synthesis, Wiley Interscience, 3$^{rd}$ Edition 1999). A preferred protecting group (PG) is tert-butoxycarbamate, cleaved preferentially under acidic conditions, using acid such as but not limited to HCl in a solvent such as but not limited MeOH (scheme 11).

scheme 11

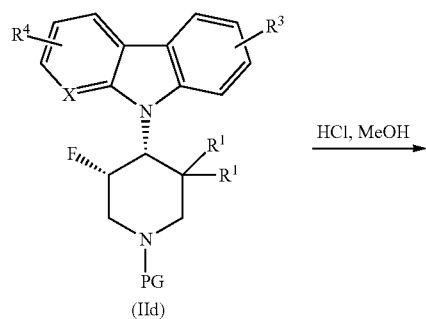

Optically active compounds of general formula (Id) preferentially of cis relative stereochemistry, are obtained by the deprotection of compounds of general formula (IId), preferentially of cis relative stereochemistry, protected with a protecting group such as but not limited to tert-butylcarbamate, in conditions well known to those skilled in the art (Kocienski P. J., Protecting groups, Georg Thieme Verlag Stuttgart, New York, 1994 and Greene, T. W., Wuts P. G. Protective groups in organic synthesis, Wiley Interscience, 3$^{rd}$ Edition 1999). A preferred protecting group (PG) is tert-butoxycarbamate, cleaved preferentially under acidic conditions, using acid such as but not limited to HCl in a solvent such as but not limited MeOH (scheme 12).

scheme 12

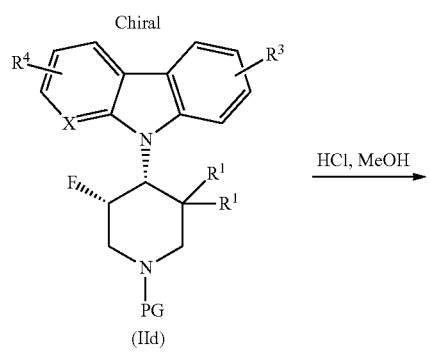

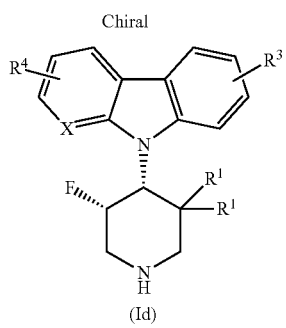

Compounds of general formula (IId) preferentially of cis relative stereochemistry, are obtained by reaction of compounds of general formula (IIc), preferentially of trans relative stereochemistry, in fluorination conditions well known to those ordinary skilled in the art, using a fluorination agent such as but not limited to DAST® in a solvent such as but not limited to THF, preferentially at low temperature (scheme 13).

scheme 13

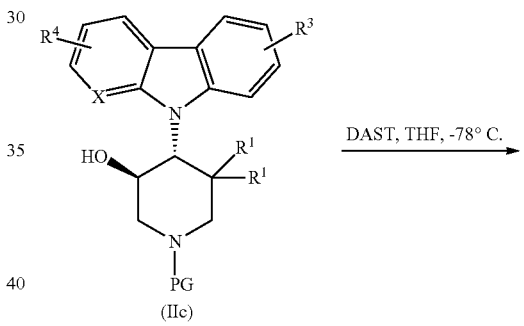

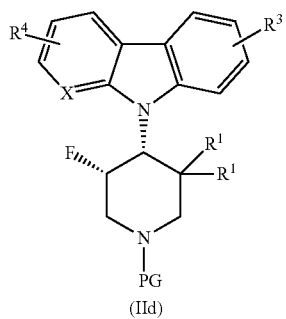

Optically active compounds of general formula (IId) preferentially of cis relative stereochemistry, are obtained by reaction of optically active compounds of general formula (c) preferentially of trans relative stereochemistry, with a fluorination agent well known to those skilled in the art. Typical conditions use a fluorination reagent such as but not limited to DAST® in a solvent such as but not limited to THF, preferentially at low temperature (scheme 14).

scheme 14

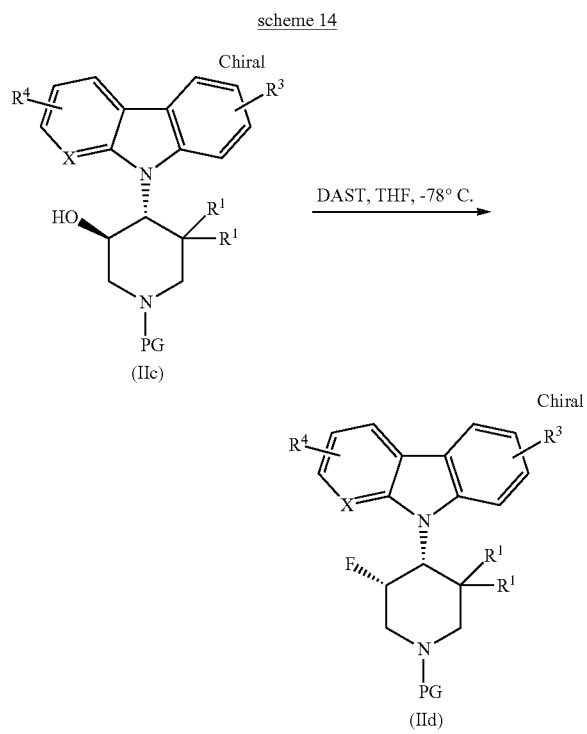

Optically active compounds of general formula (IIc) preferentially of trans relative stereochemistry, are obtained in all proportions by chiral separation of racemate of general formula (IIc), preferentially of trans relative stereochemistry, using separation techniques well known to those skilled in the art, such as but not limited to chiral chromatography (SFC) separation (scheme 15).

scheme 15

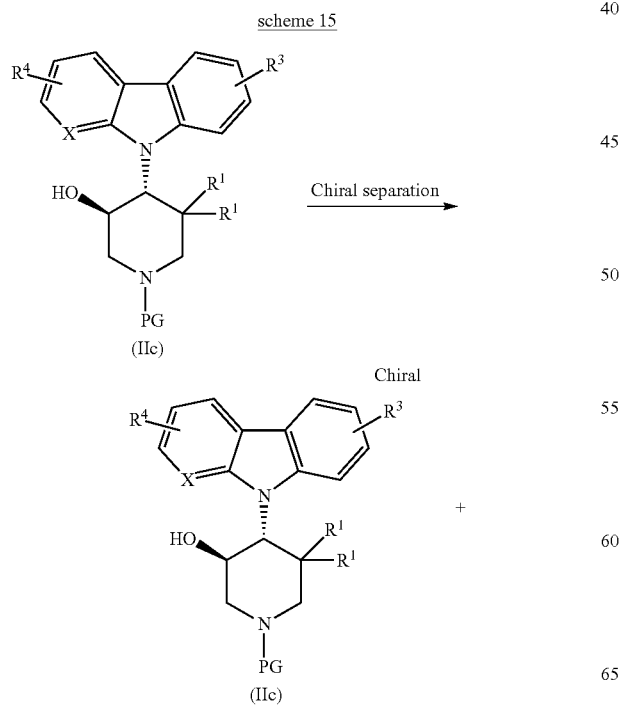

Optically active compounds of general formula (II'c) preferentially of trans relative stereochemistry, are obtained in all proportions by chiral separation of racemate of general formula (II'c), preferentially of trans relative stereochemistry, using separation techniques well known to those skilled in the art, such as but not limited to chiral chromatograpy (SFC) separation (scheme 16).

scheme 16

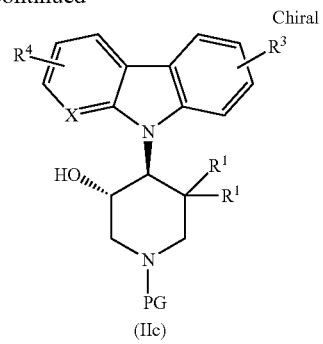
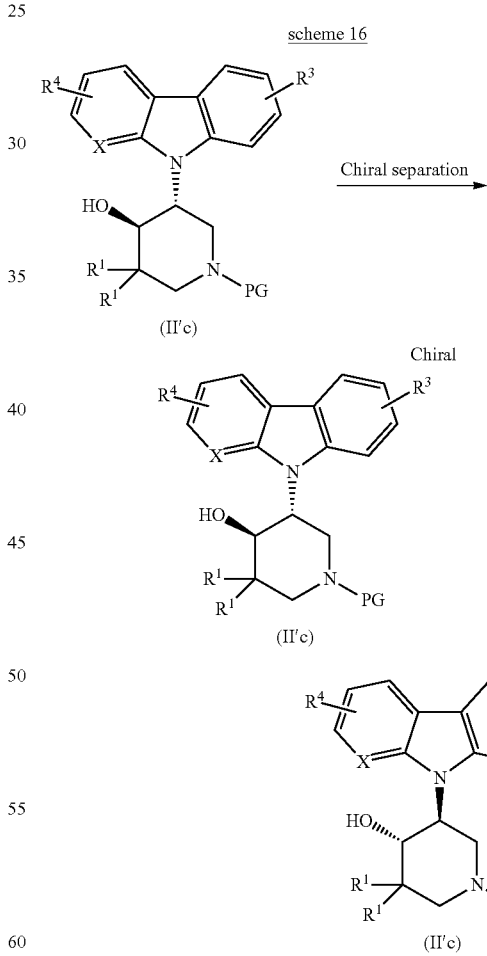

Compounds of general formula (IIc) and (II'c) for which $R^1$ is an hydrogen, preferentially of trans relative stereochemistry, are obtained through the epoxyde opening reaction of racemates of general formula (III), by a nucleophile of general formula (IV). Typical conditions use with a base such as but not limited to Cesium carbonate in a solvent such as but not limited to DMF (scheme 17).

scheme 17

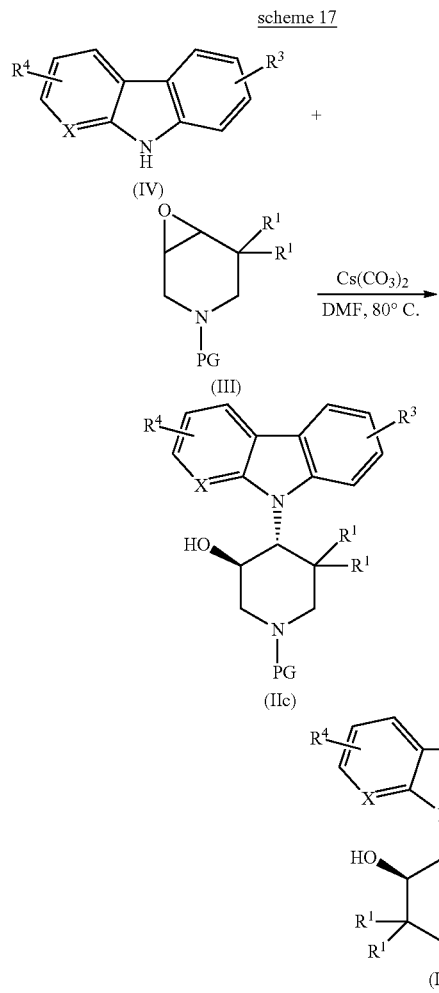

Compounds of general formula (IIe) for which R¹ is a fluorine, preferentially of trans relative stereochemistry, are obtained through the deprotection reaction of compounds of general formula (IIe) by conditions well known to those skilled in the art (Kocienski P. J., Protecting groups, Georg Thieme Verlag Stuttgart, New York, 1994 and Greene, T. W., Wuts P. G. Protective groups in organic synthesis, Wiley Interscience, 3$^{rd}$ Edition 1999) (scheme 18).

scheme 18

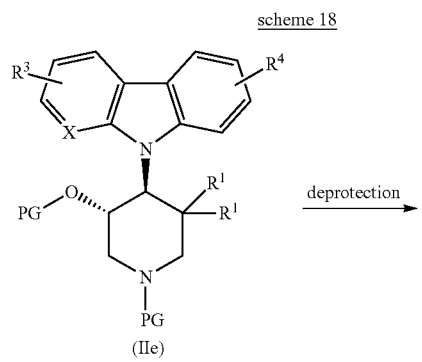

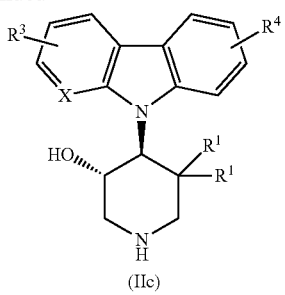

Compounds of general formula (II'e) for which R¹ is a fluorine, preferentially of trans relative stereochemistry, are obtained through the deprotection reaction of compounds of general formula (II'e) by conditions well known to those skilled in the art (Kocienski P. J., Protecting groups, Georg Thieme Verlag Stuttgart, New York, 1994 and Greene, T. W., Wuts P. G. Protective groups in organic synthesis, Wiley Interscience, 3$^{rd}$ Edition 1999) (scheme 19).

scheme 19

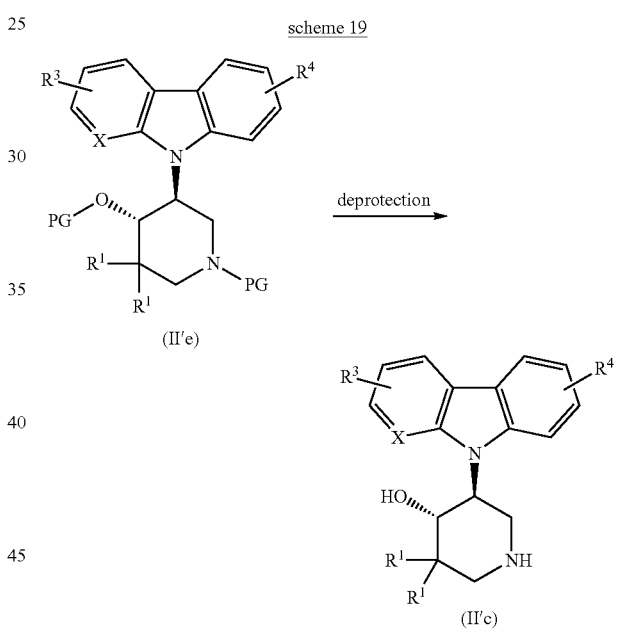

Compounds of general formula (IIe) for which R¹ is a fluorine atom are prepared from compound of general formula (III'), for which R¹ is a fluorine atom and compound of general formula (IV), using nucleophilic substitutions conditions well known to those skilled in the art. Typically, the reagent used is NaH, using a solvent such as but not limited to THF, preferentially at low temperature (scheme 20).

scheme 20

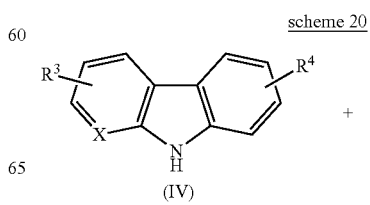

-continued

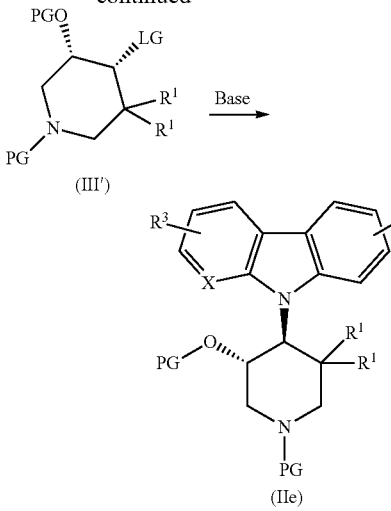
(III')

(IIe)

Compounds of general formula (II'e) for which R¹ is a fluorine atom are prepared from compound of general formula (III'), for which R¹ is a fluorine atom and compound of general formula (IV), using nucleophilic substitutions conditions well known to those skilled in the art. Typically, the reagent used is NaH, using a solvent such as but not limited to THF, preferentially at low temperature (scheme 21).

scheme 21

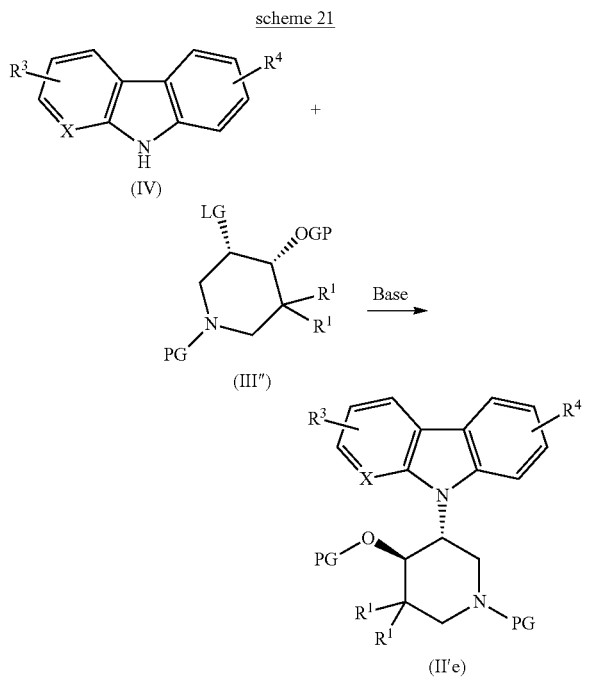
(IV)

(III'')

(II'e)

Optically active compounds of general formula (IIc) for which R¹ is a fluorine, preferentially of trans relative stereochemistry, are obtained through the deprotection reaction of optically active compounds of general formula (IIe) by conditions well known to those skilled in the art (Kocienski P. J., Protecting groups, Georg Thieme Verlag Stuttgart, New York, 1994 and Greene, T. W., Wuts P. G. Protective groups in organic synthesis, Wiley Interscience, 3$^{rd}$ Edition 1999) (scheme 22).

scheme 22

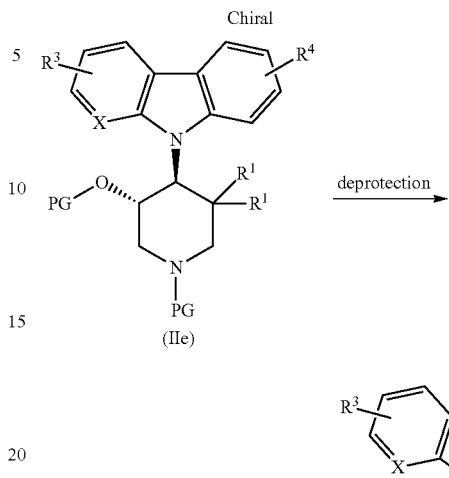
(IIe)

(IIc)

Optically active compounds of general formula (II'c) for which R¹ is a fluorine, preferentially of trans relative stereochemistry, are obtained through the deprotection reaction of optically active compounds of general formula (II'e) by conditions well known to those skilled in the art (Kocienski P. J., Protecting groups, Georg Thieme Verlag Stuttgart, New York, 1994 and Greene, T. W., Wuts P. G. Protective groups in organic synthesis, Wiley Interscience, 3$^{rd}$ Edition 1999) (scheme 23).

scheme 23

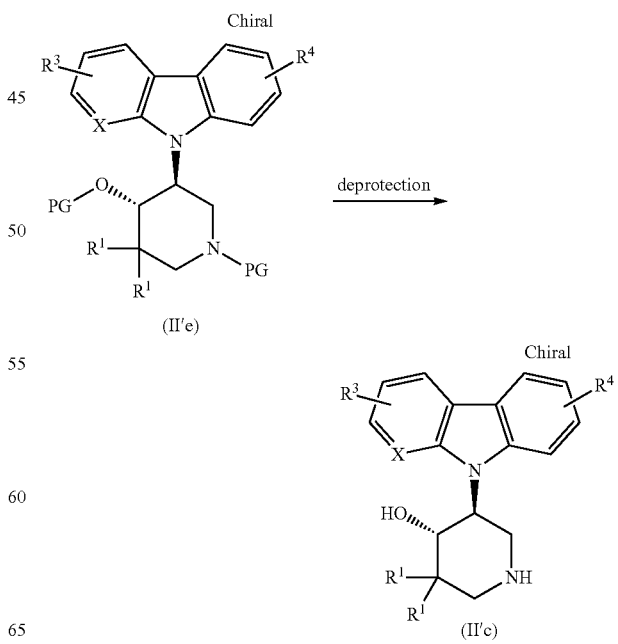
(II'e)

(II'c)

Optically active compounds of general formula (IIe) for which $R^1$ is a fluorine atom are prepared from optically active compound of general formula (III'), for which $R^1$ is a fluorine atom and compound of general formula (IV), using nucleophilic substitutions conditions well known to those skilled in the art. Typically, the reagent used is NaH, using a solvent such as but not limited to THF, preferentially at low temperature (scheme 24).

scheme 24

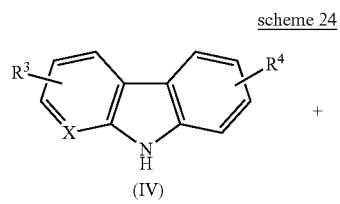

(IV)

+

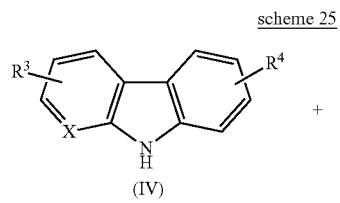

(III')

Base
→

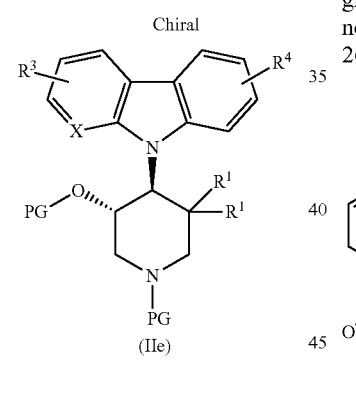

(IIe)

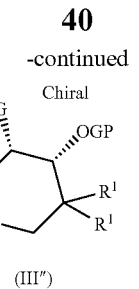

(III'')

Base
→

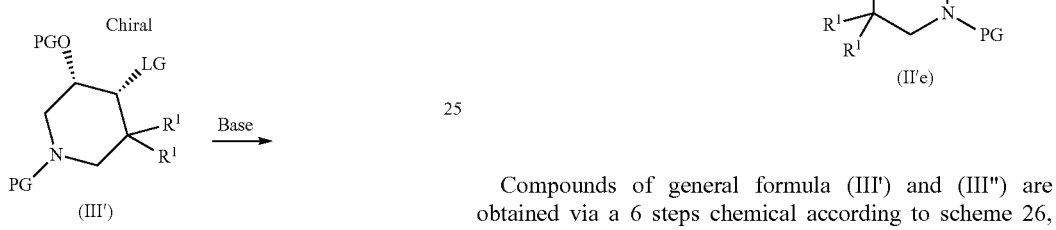

(II'e)

Compounds of general formula (III') and (III'') are obtained via a 6 steps chemical according to scheme 26, using 3-Hydroxy-3,6-dihydro-2H-pyridine-1-carboxylic acid tert-butyl ester as starting material. A preferred leaving group is chosen within sulfonates leaving groups such as but not limited to nosylate, tosylate, triflate mesylate (scheme 26)

scheme 26

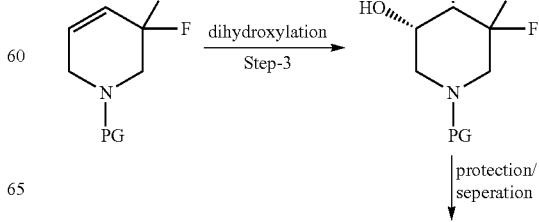

3- Hydroxy-3, 6-dihydro-2H-pyridine-1-carboxylic acid tert-butyl ester

Optically active compounds of general formula (II'e) for which $R^1$ is a fluorine atom are prepared from optically active compound of general formula (III''), for which R' is a fluorine atom and compound of general formula (IV), using nucleophilic substitutions conditions well known to those skilled in the art. Typically, the reagent used is NaH, using a solvent such as but not limited to THF, preferentially at low temperature (scheme 25).

scheme 25

+

(IV)

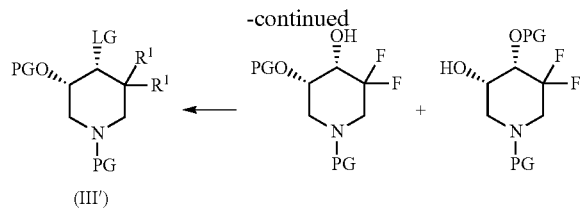

(III')

Optically active compounds of general formula (III') are obtained via a 6 steps chemical scheme 27, using opticall active 3-Hydroxy-3,6-dihydro-2H-pyridine-1-carboxylic acid tert-butyl ester as starting material. A preferred leaving group is chosen within sulfonates leaving groups such as but not limited to nosylate, tosylate, triflate or mesylate (scheme 26)

scheme 27

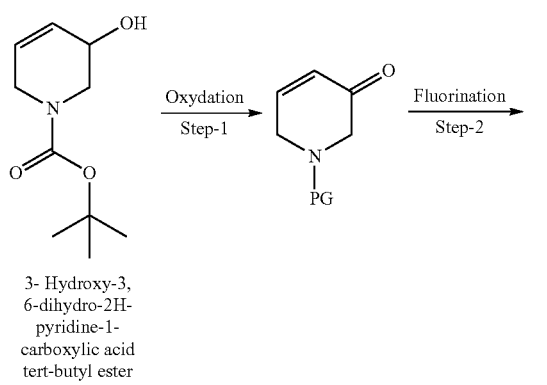

3-Hydroxy-3,6-dihydro-2H-pyridine-1-carboxylic acid tert-butyl ester

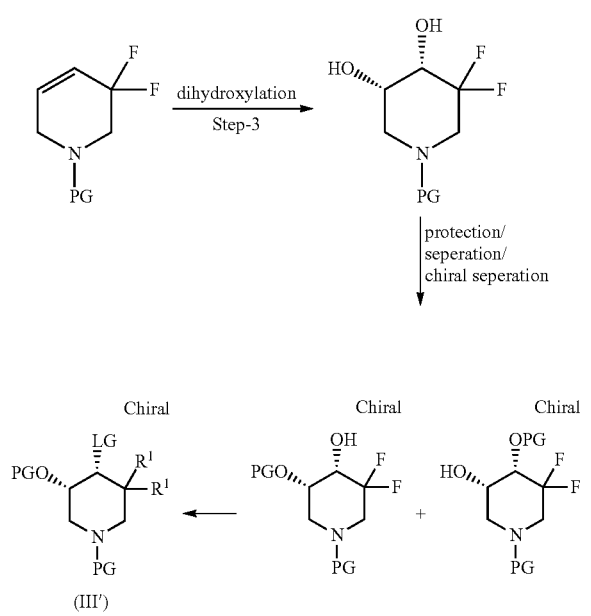

(III')

Compounds of general formula (IV) for which X=N are prepared by catalyzed reaction of compounds of general formula (VI), well known to those skilled in the art. Typically, the reaction is run in a solvent such as but not limited to xylene with a catalyst such as but not limited to palladium diacetate, using conditions reported in the literature (Laha, J. K., Petrou, P. Cuny G. C., *J. Org. Chem.* 2009, 74, 3152-3155) (scheme 28).

scheme 28

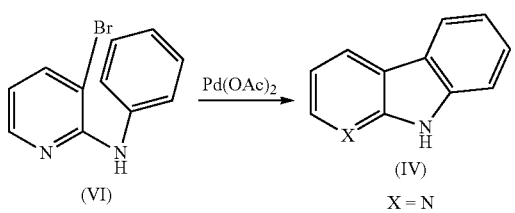

Compounds having the general formula (III) (with $R^1=R^2=H$), (IV) (with X=C), (V) (with $R^3=H$ and $R^4=OH$), and (VI) are commercially available from suppliers such as ABCR, Sigma Aldrich, or prepared using protocols from literature as mentioned in the examples.

The method for preparing compounds of formula (I), (Ia), (Ic), (Id), (Ib), (IIc), (IId), (IV), (III), (IV), (IIc'), (IIc) selected below:

3-Chloro-6-fluoro-9H-carbazole
(3S,4S)-4-(3,6-Dichloro-carbazol-9-yl)-3-hydroxy-piperidine-1-carboxylic acid tert-butyl ester
(3R,4R)-4-(3,6-Dichloro-carbazol-9-yl)-3-hydroxy-piperidine-1-carboxylic acid tert-butyl ester
(3S,4S)-4-(3,6-Difluoro-carbazol-9-yl)-3-hydroxy-piperidine-1-carboxylic acid tert-butyl ester
(3R,4R)-4-(3,6-Difluoro-carbazol-9-yl)-3-hydroxy-piperidine-1-carboxylic acid tert-butyl ester
:(3S,4S)-4-(3-Chloro-6-fluoro-carbazol-9-yl)-3-hydroxy-piperidine-1-carboxylic acid tert-butyl ester
trans-3-(3,6-Dichloro-carbazol-9-yl)-3-hydroxy-piperidine-1-carboxylic acid tert-butyl ester
(3R,4S)-4-(3,6-Dichloro-carbazol-9-yl)-3-fluoro-piperidine-1-carboxylic acid tert-butyl ester
(3S,4R)-4-(3-Chloro-6-fluoro-carbazol-9-yl)-3-fluoro-piperidine-1-carboxylic acid tert-butyl ester
(3R,4S)-4-(3-Chloro-6-fluoro-carbazol-9-yl)-3-fluoro-piperidine-1-carboxylic acid tert-butyl ester
trans-4-(3-Chloro-6-fluoro-carbazol-9-yl)-3-hydroxy-piperidine-1-carboxylic acid tert-butyl ester
trans-3-(3-Chloro-6-fluoro-carbazol-9-yl)-4-hydroxy-piperidine-1-carboxylic acid tert-butyl ester.
(3S,4S)-4-(3-Chloro-6-fluoro-carbazol-9-yl)-piperidin-3-ol hydrochloride salt
(3R,4R)-4-(3-Chloro-6-fluoro-carbazol-9-yl)-piperidin-3-ol hydrochloride salt
Trans-4-(3,6-Dichloro-carbazol-9-yl)-piperidin-3-ol hydrochloride salt
(3S,4S)-4-(3,6-Dichloro-carbazol-9-yl)-piperidin-3-ol hydrochloride salt
(3R,4R)-4-(3,6-Dichloro-carbazol-9-yl)-piperidin-3-ol hydrochloride salt
(3S,4S)-3-(3,6-Dichloro-carbazol-9-yl)-4-hydroxy-piperidine-4-ol hydrochloride salt (3S,4S)-4-(3,6-Difluoro-carbazol-9-yl)-piperidin-3-ol hydrochloride salt
(3R,4R)-4-(3,6-Difluoro-carbazol-9-yl)-piperidin-3-ol hydrochloride salt
3,6-Dichloro-9-((3R,4S)-3-fluoro-piperidin-4-yl)-9-H-carbazole hydrochloride salt
3-Chloro-6-fluoro-9-((3S,4R)-3-fluoro-piperidin-4-yl)-9H-carbazole hydrochloride salt
3-Chloro-6-fluoro-9-((3R,4S)-3-fluoro-piperidin-4-yl)-9H-carbazole hydrochloride salt
(3S,4S)-1-Cyclohexyl-3-(3,6-dichloro-carbazol-9-yl)-piperidin-4-ol
(3R,4R)-4-Carbazol-9-yl-piperidin-3-ol
(3S,4S)-4-Carbazol-9-yl-piperidin-3-ol
trans-tert-butyl 3-(3,6-difluoro-9H-carbazol-9-yl)-4-hydroxypiperidine-1-carboxylate
trans-tert-butyl 4-(3,6-difluoro-9H-carbazol-9-yl)-3-hydroxypiperidine-1-carboxylate
(3R,4R)-tert-butyl 3-(3,6-difluoro-9H-carbazol-9-yl)-4-hydroxypiperidine-1-carboxylate
(3S,4S)-tert-butyl 3-(3,6-difluoro-9H-carbazol-9-yl)-4-hydroxypiperidine-1-carboxylate
(3R,4R)-3-(3,6-difluoro-9H-carbazol-9-yl)piperidin-4-ol
(3R,4R)-3-(3,6-difluoro-9H-carbazol-9-yl)-1-neopentylpiperidin-4-ol
(3R,4R)-1-(cyclopropylmethyl)-3-(3,6-difluoro-9H-carbazol-9-yl)piperidin-4-ol
(3R,4R)-3-(3,6-difluoro-9H-carbazol-9-yl)-1-(4,4,4-trifluorobutyl)piperidin-4-ol
(3R,4R)-3-(3,6-difluoro-9H-carbazol-9-yl)-1-((1-(trifluoromethyl)cyclopropyl)methyl)piperidin-4-ol
(3R,4R)-3-(3,6-difluoro-9H-carbazol-9-yl)-1-(3,3,3-trifluoropropyl)piperidin-4-ol
(3R,4R)-3-(3,6-difluoro-9H-carbazol-9-yl)-1-phenethyl-piperidin-4-ol
trans-1-benzyl-3-(3,6-difluoro-9H-carbazol-9-yl)piperidin-4-ol
trans-1-benzyl-4-(3,6-difluoro-9H-carbazol-9-yl)piperidin-3-ol
(3R,4R)-1-benzyl-3-(3,6-difluoro-9H-carbazol-9-yl)piperidin-4-ol
(3S,4S)-1-benzyl-3-(3,6-difluoro-9H-carbazol-9-yl)piperidin-4-ol
trans-3-(3,6-difluoro-9H-carbazol-9-yl)piperidin-4-ol
(3S,4S)-3-(3,6-difluoro-9H-carbazol-9-yl)piperidin-4-ol
(3R,4R)-3-(3,6-dichloro-9H-carbazol-9-yl)piperidin-4-ol
(3R,4R)-3-(3,6-dichloro-9H-carbazol-9-yl)-1-(3,3,3-trifluoropropyl)piperidin-4-ol -trans-3-(3,6-bis(trifluoromethyl)-9H-carbazol-9-yl)piperidin-4-ol
trans-4-(3,6-bis(trifluoromethyl)-9H-carbazol-9-yl)piperidin-3-01
(3R,4R)-4-(3,6-bis(trifluoromethyl)-9H-carbazol-9-yl)piperidin-3-ol
(3S,4S)-4-(3,6-bis(trifluoromethyl)-9H-carbazol-9-yl)piperidin-3-ol
(3R,4R)-3-(3,6-dichloro-9H-pyrido[2,3-b]indol-9-yl)piperidin-4-ol
(3S,4S)-3-(3,6-dichloro-9H-pyrido[2,3-b]indol-9-yl)piperidin-4-ol
(3R,4R)-4-(3,6-dichloro-9H-pyrido[2,3-b]indol-9-yl)piperidin-3-ol
(3S,4S)-4-(3,6-dichloro-9H-pyrido[2,3-b]indol-9-yl)piperidin-3-ol
(3R,4R)-4-(3,6-dichloro-9H-pyrido[2,3-b]indol-9-yl)piperidin-3-ol
(3R,4R)-4-(3,6-dichloro-9H-pyrido[2,3-b]indol-9-yl)-1-(3,3,3-trifluoropropyl)piperidin-3-ol
(3R,4R)-3-(3,6-dichloro-9H-pyrido[2,3-b]indol-9-yl)piperidin-4-ol
(3R,4R)-3-(3,6-dichloro-9H-pyrido[2,3-b]indol-9-yl)-1-(3,3,3-trifluoropropyl)piperidin-4-ol are more particularly described in the examples.

Ac (acetyl), ABS (enantiopure form), ACN (acetonitrile), brs (broad singlet), Boc (tert-butoxycarbonyl), d (doublet), DCE (dichloroethane), DCM (dichloromethane), DMF (dimethylformamide), DMSO (dimethylsulfoxide), EA (ethyl acetate), equiv. (equivalent), ESI (electro-spray ionization), Et (ethyl), Et$_2$O (diethyl ether), EtOAc (ethyl acetate), h (hour), HPLC (high performance liquid chromatography), L (liter), LC (liquid chromatography), MD Autoprep (mass directed preparative HPLC), MeOH (methanol), MeOD (deuterated methanol), mg (milligram), min (minute), mL (milliliter), μL (microliter), M.P. (melting point), mm (millimeter), μm (micrometer), mmol (millimole), m (multiplet), MS (mass spectrometry), NMR (nuclear magnetic resonance), PE (petroleum ether), q (quadruplet), RAC (racemic mixture) Rt (retention time), rt (room temperature), on (overnight), s (singlet), SFC (supercritical fluid chromatography) SPE (solid phase extraction), TBAF (tetrabutylammonium fluoride), TFA (trifluoroacetic acid), THF (tetrahydrofuran), t (triplet), UPLC (ultra performance liquid chromatography).

The commercially available starting materials used in the following experimental description were purchased from Sigma-Aldrich-Fluka unless otherwise reported. However, specific reagents were purchased from another suppliers: 3,6-dichlorocarbazole (3B Scientific Corporation), 1-Boc-3,4-epoxypiperidine (Advanced ChemBlocks, Inc.).

Unless indicated otherwise NMR, HPLC and MS data provided in the examples described below are registered on:

NMR: Bruker DPX-300 (300 MHz), using residual signal of deuterated solvent as internal reference.

HPLC: Waters Alliance 2695, column Waters XBridge C8 3.5 μm 4.6×50 mm, conditions: solvent A (H$_2$O with 0.1% TFA), solvent B (ACN with 0.05% TFA), gradient 5% B to 100% B over 8 min, UV detection with PDA Water 996 (230-400 nm).

UPLC: Waters Acquity, column Waters Acquity UPLC BEH C18 1.7 μm 2.1×50 mm, conditions: solvent A (10 mM ammonium acetate in water+5% ACN), solvent B (ACN), UV detection (PDA, 230-400 nm) and MS detection (SQ detector, positive and negative ESI modes, cone voltage 30 V). Gradient 5% B to 100% B over 3 min or gradient 40% B to 100% B over 3 min.

MD Autoprep: preparative HPLC purifications are performed with a mass directed autopurification Fractionlynx from Waters equipped with a Sunfire Prep C18 OBD column 19×100 mm or 30×100 mm 5 μm, unless otherwise reported. All HPLC purifications were performed with a gradient of ACN/H$_2$O or ACN/H$_2$O/HCOOH (0.1%).

The microwave chemistry was performed on a single mode microwave reactor (Emrys™ Optimiser or Initiator™ Sixty from Biotage, or Explorer from CEM). LCMS: Method: A-0.1% TFA in H$_2$O, B-0.1% TFA in ACN, Flow-2.0 mL/min Column: XBridge C8 (50×4.6 mm, 3.5u), +ve mode The compounds of invention have been named according to the standards used in the program "ACD/Name Batch"

from Advanced Chemistry Development Inc., ACD/Labs (7.00 Release). Product version: 7.10, build: 15 Sep. 2003

3,6-difluoro-9H-carbazole is prepared according to the protocol of Bedford, Robin B. et al *Tetrahedron* 2008, 64, 6038-6050.

INTERMEDIATE 1

3-Chloro-6-fluoro-9H-carbazole

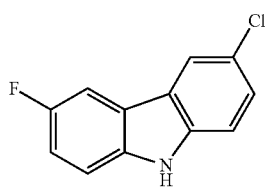 [SMILES: Fc1ccc2[nH]c3ccc(Cl)cc3c2c1]

To a stirred solution of 3-fluoro-9H-carbazole (12 g, 0.07 mol) in dry DMF (25 mL) was added N-chlorosuccinimide (10 g, 0.07 mol) in DMF (15 mL) dropwise at 0° C. The reaction mixture was allowed to stir at 0° C. for 20 min. The reaction mixture was quenched in ice water and extracted with EtOAc. The organic layer was washed with saturated sodium chloride solution, dried over $Na_2SO_4$ and concentrated under vacuum. The solid was recrystallised with 5% of EtOAc in petroleum ether to yield the title compound as a white solid. $^1$H NMR (400 MHz, DMSO-$d_6$) δ 11.46 (s, 1H), 8.24 (d, J=2.1 Hz, 1H), 8.02-7.99 (m, 1H), 7.50-7.47 (m, 2H), 7.28-7.23 (m, 1H). HPLC 5.16 min (Purity >99%). LCMS 6.57 min, 99.8%, 219.0 ([M+H]+).

General Procedure a for Intermediates

INTERMEDIATE 2

(3S,4S)-4-(3,6-Dichloro-carbazol-9-yl)-3-hydroxy-piperidine-1-carboxylic acid tert-butyl ester

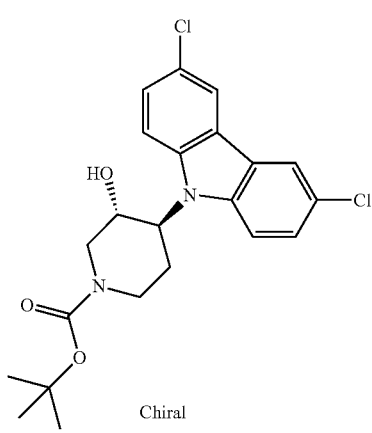 [SMILES: CC(C)(C)OC(=O)N1CC[C@H](n2c3ccc(Cl)cc3c3cc(Cl)ccc32)[C@@H](O)C1]

Chiral

Step 1: Trans-4-(3,6-Dichloro-carbazol-9-yl)-3-hydroxy-piperidine-1-carboxylic acid tert-butyl ester. To a suspension of $Cs(CO_3)_2$ (48.3 g, 148.2 mmol, 5 equiv.) in DMF (350 mL, 50 V) previously stirred during 1 h at 80° C. was added 3,6-dichlorocarbazole (7.0 g, 29.6 mmol, 1 equiv.). The resulting mixture was stirred 1 h at 80° C., then 1-Boc-3,4-epoxypiperidine (7.1 g, 35.6 mmol, 1 equiv.) was added. The mixture was stirred at 80° C. during 12 to 72 h and was then allowed to cool to rt. The mixture was filtrated through a plug of celite, concentrated under reduced pressure and purified by Column chromatography (EtOAC 15 to 50% in n-heptan). The resulting two fractions were concentrated under reduced pressure to afford separated regioisomer, Trans-4-(3,6-Dichloro-carbazol-9-yl)-3-hydroxy-piperidine-1-carboxylic acid tert-butyl ester was obtained as a white powder. $^1$H NMR (DMSO) δ: 8.45-8.21 (m, 2H), 7.82-7.57 (m, 2H), 7.57-7.35 (m, 2H), 5.20 (d, J=4.6 Hz, 1H), 4.74-4.50 (m, 1H), 4.45-3.81 (m, 3H), 3.19-2.91 (m, 1H), 2.85-2.64 (m, 1H), 2.47-2.21 (m, 1H), 1.95-1.77 (m, 1H), 1.47 (s, 9H). HPLC Rt 5.65 min (Purity: 94.25%). UPLC/MS 433.5 ([M−H]−).

Step 2: (3S,4S)-4-(3,6-Dichloro-carbazol-9-yl)-3-hydroxy-piperidine-1-carboxylic acid tert-butyl ester. Trans-4-(3,6-Dichloro-carbazol-9-yl)-3-hydroxy-piperidine-1-carboxylic acid tert-butyl ester (3.17 g, 7.27 mmol) was submitted to chiral separation using SFC conditions (Column Chiralpak IC, Eluant 30% MeOH, flowrate 80 ml min, pressure 120 bars, temperature 40° C., sample concentration 10 mg/ml in DCM/MEOH 6/4, rt 1.64 min). The resulting fraction was concentrated under reduced pressure to afford (3S,4S)-4-(3,6-Dichloro-carbazol-9-yl)-3-hydroxy-piperidine-1-carboxylic acid tert-butyl as a white powder.

INTERMEDIATE 3

(3R,4R)-4-(3,6-Dichloro-carbazol-9-yl)-3-hydroxy-piperidine-1-carboxylic acid tert-butyl ester

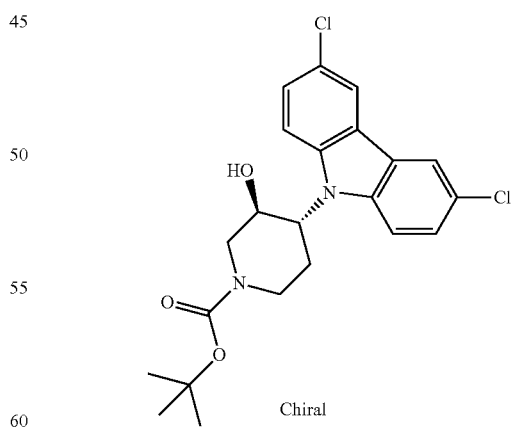

Chiral (3R,4R)-4-(3,6-Dichloro-carbazol-9-yl)-3-hydroxy-piperidine-1-carboxylic acid tert-butyl ester was obtained as a white powder according to general procedure A (SFC separation: rt 3.60 min.)

47

INTERMEDIATE 4

(3S,4S)-4-(3,6-Difluoro-carbazol-9-yl)-3-hydroxy-piperidine-1-carboxylic acid tert-butyl ester

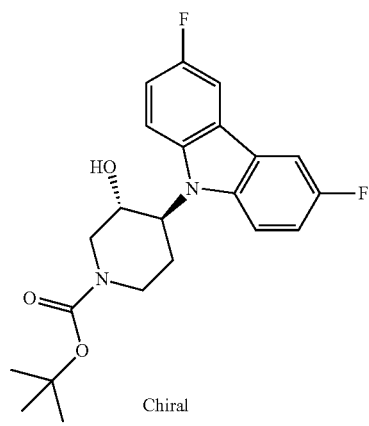 [SMILES: CC(C)(C)OC(=O)N1CC[C@H](n2c3ccc(F)cc3c3cc(F)ccc32)[C@@H](O)C1]

Chiral (3S,4S)-4-(3,6-Difluoro-carbazol-9-yl)-3-hydroxy-piperidine-1-carboxylic acid tert-butyl ester was obtained as a white powder according to general procedure A, using 3,6-difluorocarbazole (900.0 mg, 4.43 mmol, 1 equiv.) and Column Chiralpak IA, (SFC separation, rt 1.49 min)

INTERMEDIATE 5

(3R,4R)-4-(3,6-Difluoro-carbazol-9-yl)-3-hydroxy-piperidine-1-carboxylic acid tert-butyl ester

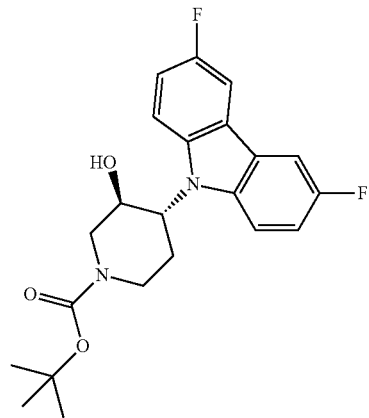

Chiral (3R,4R)-4-(3,6-Difluoro-carbazol-9-yl)-3-hydroxy-piperidine-1-carboxylic acid tert-butyl ester was obtained as a white powder according to general procedure A, using 3,6-difluorocarbazole (900.0 mg, 4.43 mmol, 1 equiv.) Column Chiralpak IA, (SFC separation: rt 2.07 min).

48

INTERMEDIATE 6

(3S,4S)-4-(3-Chloro-6-fluoro-carbazol-9-yl)-3-hydroxy-piperidine-1-carboxylic acid tert-butyl ester

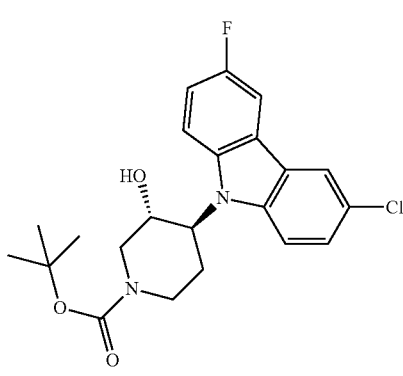

Chiral (3S,4S)-4-(3-Chloro-6-fluoro-carbazol-9-yl)-3-hydroxy-piperidine-1-carboxylic acid tert-butyl ester was obtained as a white powder according to general procedure A, using 3-Chloro-6-fluorocarbazole (1.0 g, 4.55 mmol, 1 equiv.) and Column Chiralpak IA, (SFC separation: rt 1.36 min).

INTERMEDIATE 8

(3R,4R)-4-(3-Chloro-6-fluoro-carbazol-9-yl)-3-hydroxy-piperidine-1-carboxylic acid tert-butyl ester

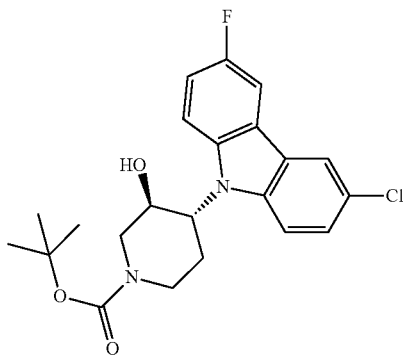

Chiral (3R,4R)-4-(3-Chloro-6-fluoro-carbazol-9-yl)-3-hydroxy-piperidine-1-carboxylic acid tert-butyl ester was obtained as a white powder according to general procedure A, using 3-Chloro-6-fluorocarbazole (1.0 g, 4.55 mmol, 1 equiv.) and Column Chiralpak IA, (SFC separation: rt 2.33 min).

INTERMEDIATE 9 trans-3-(3,6-Dichloro-carbazol-9-yl)-3-hydroxy-piperidine-1-carboxylic acid tert-butyl ester

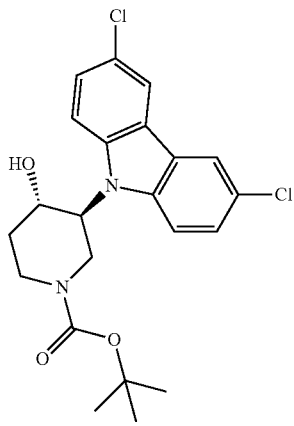 [SMILES: CC(C)(C)OC(=O)N1CC[C@H](O)[C@@H](n2c3ccc(Cl)cc3c3cc(Cl)ccc32)C1]

Trans-4-(3,6-Dichloro-carbazol-9-yl)-3-hydroxy-piperidine-1-carboxylic acid tert-butyl ester was obtained as awhite powder, according to general procedure A, using 3,6-dichlorocarbazole (7.0 g, 29.6 mmol, 1 equiv.).

General Procedure B for Intermediates

INTERMEDIATE 10

(3R,4S)-4-(3,6-Dichloro-carbazol-9-yl)-3-fluoro-piperidine-1-carboxylic acid tert-butyl ester

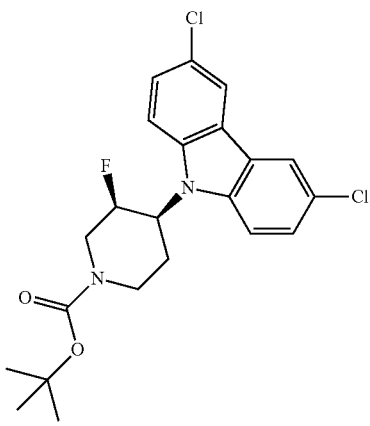

Chiral

To a solution of intermediate 2 (90.0 mg, 0.21 mmol, 1 equiv.) in THF (5 mL) at 0° C., was added Diethylamino-sulfur trifluoride, 95% (43.3 mg, 0.27 mmol, 1.3 equiv.). The mixture was stirred during 15 h and allowed to warm to rt. The reaction was quenched by adding a saturated solution of sodium hydrogenocarbonate and the mixture was diluted with DCM (10 mL). The aqueous layer was separated, washed with DCM (3*10 mL). The combined organic layers were dried on MgSO4, concentrated under reduced pressure to give (3R,4S)-4-(3,6-Dichloro-carbazol-9-yl)-3-fluoro-piperidine-1-carboxylic acid tert-butyl ester as a white powder. that was used without further purification.

INTERMEDIATE 11

(3S,4R)-4-(3-Chloro-6-fluoro-carbazol-9-yl)-3-fluoro-piperidine-1-carboxylic acid tert-butyl ester

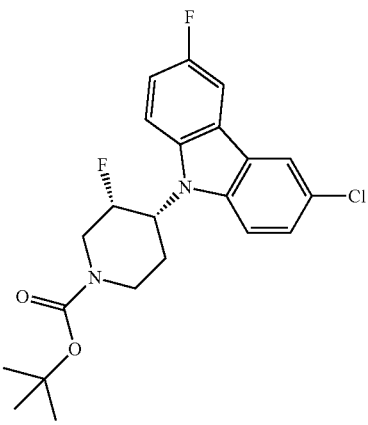

Chiral (3S,4R)-4-(3-Chloro-6-fluoro-carbazol-9-yl)-3-fluoro-piperidine-1-carboxylic acid tert-butyl ester was obtained as a white powder according to general procedure B using intermediate 8 as starting material.

INTERMEDIATE 12

(3R,4S)-4-(3-Chloro-6-fluoro-carbazol-9-yl)-3-fluoro-piperidine-1-carboxylic acid tert-butyl ester

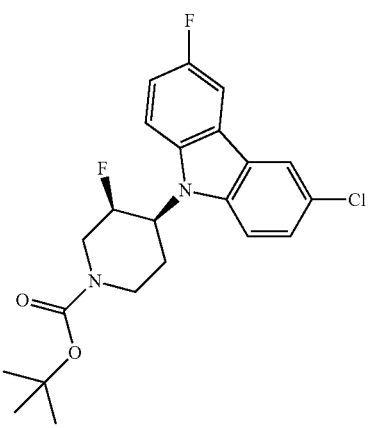

Chiral (3R,4S)-4-(3-Chloro-6-fluoro-carbazol-9-yl)-3-fluoro-piperidine-1-carboxylic acid tert-butyl ester was obtained as a white powder according to general procedure B using intermediate 7 as starting material.

INTERMEDIATE 13

(3S,4S)-4-Carbazol-9-yl-3-hydroxy-piperidine-1-carboxylic acid tert-butyl ester

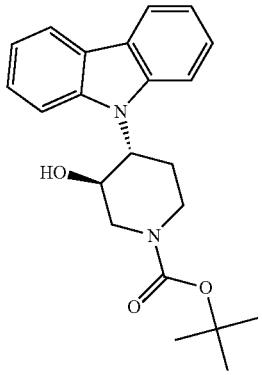

Chiral (3S,4S)-4-Carbazol-9-yl-3-hydroxy-piperidine-1-carboxylic acid tert-butyl ester was obtained as a white powder according to general procedure A using carbazole as starting material.

INTERMEDIATE 14

(3S,4S)-4-Carbazol-9-yl-3-hydroxy-piperidine-1-carboxylic acid tert-butyl ester

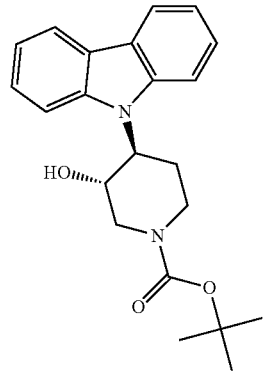

Chiral (3R,4R)-4-Carbazol-9-yl-3-hydroxy-piperidine-1-carboxylic acid tert-butyl ester was obtained as a white powder according to general procedure A using carbazole as starting material.

| Intermediates | | $^1$H NMR | HPLC | UPLC/MS |
|---|---|---|---|---|
| Intermediate 2 | | $^1$H NMR (DMSO-$d_6$) δ 8.50-8.21 (m, 2H), 7.83-7.56 (m, 2H), 7.56-7.34 (m, 2H), 5.20 (d, J = 4.5 Hz, 1H), 4.73-4.47 (m, 1H), 4.31-4.14 (m, 2H), 4.14-3.97 (m, 1H), 3.15-2.89 (m, 1H), 2.88-2.65 (m, 1H), 2.47-2.28 (m, 1H), 1.97-1.71 (m, 1H), 1.48 (s, 9H) | Rt 5.65 min (Purity: 96.5%) | 493.3 ([M + CH$_3$COO]$^-$) |
| Intermediate 3 | | $^1$H NMR (DMSO-$d_6$) δ 8.50-8.21 (m, 2H), 7.83-7.56 (m, 2H), 7.56-7.34 (m, 2H), 5.20 (d, J = 4.5 Hz, 1H), 4.73-4.74 (m, 1H), 4.31-4.14 (m, 2H), 4.14-3.97 (m, 1H), 3.15-2.89 (m, 1H), 2.88-2.65 (m, 1H), 2.47-2.28 (m, 1H), 1.97-1.71 (m, 1H), 1.48 (s, 9H). | Rt 5.65 min (Purity: 96.5%) | 493.3 ([M + CH$_3$COO]$^-$) |

-continued

| Intermediates | ¹H NMR | HPLC | UPLC/MS |
|---|---|---|---|
| Intermediate 4 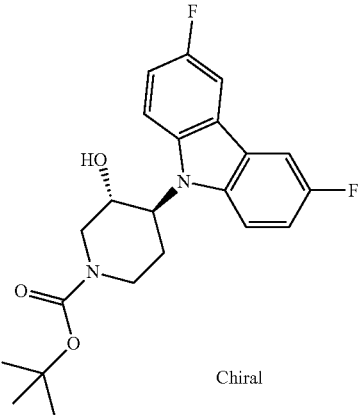 Chiral | ¹H NMR (DMSO-d₆) δ 8.04 (d, J = 8.8 Hz, 2H), 7.66 (br s, 2H), 7.30 (br s, 2H), 5.18 (d, J = 4.7 Hz, 1H), 4.71-4.52 (m, 1H), 4.37-4.14 (m, 2H), 4.14-3.98 (m, 1H), 3.02 (br s, 1H), 2.74 (br s, 1H), 2.48-2.23 (m, 1H), 1.91-1.76 (m, 1H), 1.47 (s, 9H) | Rt 5.12 min (Purity: 99.4%) | 403.2 ([M + H]⁺) |
| Intermediate 5 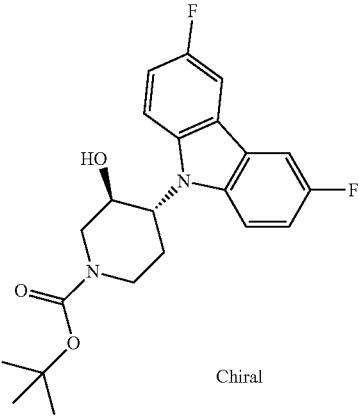 Chiral | ¹H NMR (DMSO-d₆) δ 8.04 (d, J = 8.8 Hz, 2H), 7.66 (br s, 2H), 7.30 (br s, 2H), 5.18 (d, J = 4.7 Hz, 1H), 4.71-4.52 (m, 1H), 4.37-4.14 (m, 2H), 4.14-3.98 (m, 1H), 3.02 (br s, 1H), 2.74 (br s, 1H), 2.48-2.23 (m, 1H), 1.91-1.76 (m, 1H), 1.47 (s, 9H) | Rt 5.08 min (Purity: 99.4%) | 403.1 ([M + H]⁺) |
| Intermediate 7 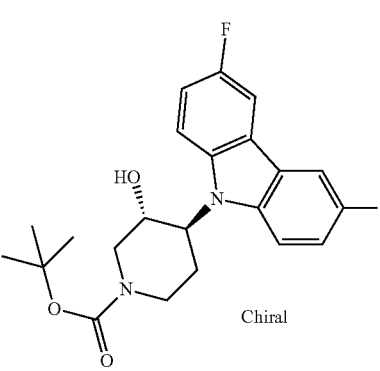 Chiral | ¹H NMR (DMSO-d₆) δ 8.31 (br s, 1H), 8.09 (d, J = 6.7 Hz, 1H), 7.69 (br s, 2H), 7.52-7.37 (m, 1H), 7.37-7.17 (m, 1H), 5.19 (d, J = 4.6 Hz, 1H), 4.73-4.47 (m, 1H), 4.33-4.14 (m, 2H), 4.14-4.01 (m, 1H), 3.02 (br s, 1H), 2.74 (br s, 1H), 2.45-2.21 (m, 1H), 1.98-1.77 (m, 1H), 1.47 (s, 9H) | Rt 5.34 min (Purity: 96.6%) | 477.5 ([M + CH₃COO]⁻) |

| Intermediates | ¹H NMR | HPLC | UPLC/MS |
|---|---|---|---|
| Intermediate 8 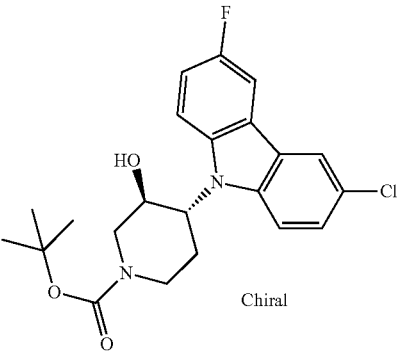 Chiral | ¹H NMR (DMSO-d$_6$) δ 8.31 (br s, 1H), 8.09 (d, J = 7.0 Hz, 1H), 7.69 (br s, 2H), 7.45 (m, 1H), 7.31 (m, 1H), 5.19 (d, J = 4.5 Hz, 1H), 4.72-4.47 (m, 1H), 4.32-4.14 (m, 2H), 4.14-3.96 (m, 1H), 3.03 (br s, 1H), 2.74 (br s, 1H), 2.46-2.22 (m, 1H), 1.85 (d, J = 12.4 Hz, 1H), 1.47 (s, 9H) | Rt 5.33 min (Purity: 97.2%) | 477.5 ([M + CH$_3$COO]⁻) |
| Intermediate 9 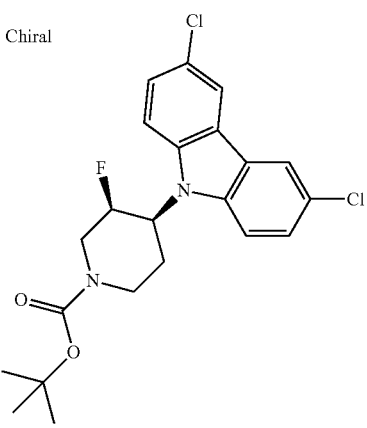 | ¹H NMR (DMSO-d$_6$) δ 8.36 (br s, 2H), 7.94 (s, 1H), 7.66 (br s, 1H), 7.57-7.29 (m, 2H), 4.99 (d, J = 5.7 Hz, 1H), 4.62-4.41 (m, 1H), 4.41-4.24 (m, 1H), 4.15-3.85 (m, 1H), 3.66 (br s, 1H), 3.16 (br s, 1H), 2.12-1.90 (m, 1H), 1.42 (s, 9H) | Rt 5.54 min (Purity: 85.5%) | 433.5 ([M − H]⁻) |
| Intermediate 10 Chiral  | | Rt 6.20 min (Purity: 98.4%) | 438.7 ([M + H⁺]) |

| Intermediates | ¹H NMR | HPLC | UPLC/MS |
|---|---|---|---|
| Intermediate 11<br>Chiral | ¹H NMR (CDCl₃) δ 7.71 (dd, J = 8.5, 3.0 Hz, 1H), 7.50-7.35 (m, 3H), 7.21 (td, J = 8.5, 3.0 Hz, 1H), 5.44-5.24 (m, 0.5H), 5.24-5.04 (m, 0.5H), 4.80-4.48 (m, 2H), 4.37 (s, 1H), 3.09-2.83 (m, 2H), 2.66 (qd, J = 12.9, 4.8 Hz, 1H), 2.13-1.90 (m, 1H), 1.55 (s, 9H) | Rt 5.89 min<br>(Purity: 99.1%) | 479.6<br>([M + CH₃COO]⁻) |
| Intermediate 12<br>Chiral | ¹H NMR (DMSO-d₆) δ 8.34 (s, 1H), 8.12 (d, J = 9.1 Hz, 1H), 7.80 (d, J = 8.9 Hz, 2H), 7.56-7.40 (m, 1H), 7.34 (s, 1H), 5.45-5.29 (m, 1H), 5.29-5.02 (m, 2H), 4.52-4.33 (m, 1H), 4.11 (d, J = 8.0 Hz, 1H), 3.23-2.95 (m, 2H), 1.94 (d, J = 13.0 Hz, 1H), 1.48 (s, 9H) | Rt 5.92 min<br>(Purity: 98.1%) | 479.5<br>([M + CH₃COO]⁻) |
| Intermediate 13<br>Chiral | ¹H NMR (400 MHz, DMSO-d₆) δ 8.21-8.09 (m, 2H), 7.70-7.53 (m, 2H), 7.47-7.34 (m, 2H), 7.17 (t, J = 7.40 Hz, 2H), 5.16 (d, J = 5.16 Hz, 1H), 4.66-4.59 (m, 1H), 4.32-4.26 (m, 1H), 4.21-4.12 (m, 1H), 4.11-4.08 (m, 1H), 3.17-3.02 (m, 1H), 2.75-2.66 (m, 1H), 2.46-2.39 (m, 1H), 1.84-1.81 (m, 1H), 1.48 (s, 9H). | Rt 6.7 min,<br>(Purity: 98.1%) | 367.0<br>[(M + H)]+ |

| Intermediates | ¹H NMR | HPLC | UPLC/MS |
|---|---|---|---|
| Intermediate 14 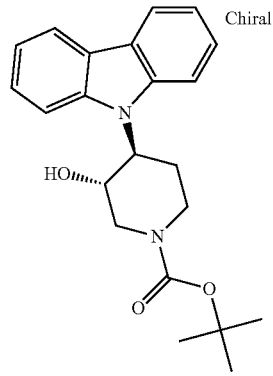 | ¹H NMR (400 MHz, DMSO-d₆): δ 8.22-8.09 (m, 2H), 7.70-7.54 (m, 2H), 7.47-7.35 (m, 2H), 7.17 (t, J = 7.36 Hz, 2H), 5.16 (d, J = 5.16 Hz, 1H), 4.64-4.59 (m, 1H), 4.11-4.08 (m, 1H), 4.32-4.27 (m, 2H), 3.33-3.15 (m, 1H), 2.85-2.65 (m, 1H), 1.95-1.81 (m, 1H), 1.70-1.47 (m, 1H), 1.38 (s, 9H). | Rt. 6.6 min, (Purity: 97.4%) | 367.0 [(M + H)]+ |

General Procedure C for Examples 1 and 2

EXAMPLE 1 trans-4-(3-Chloro-6-fluoro-carbazol-9-yl)-3-hydroxy-piperidine-1-carboxylic acid tert-butyl ester

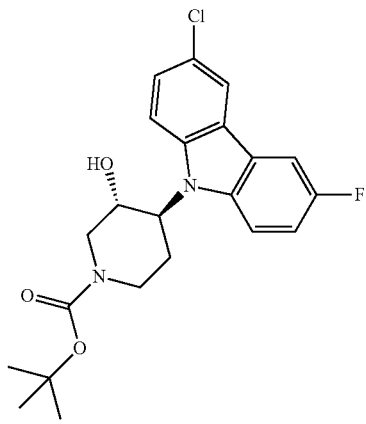 [SMILES: CC(C)(C)OC(=O)N1CC[C@H](n2c3ccc(F)cc3c3cc(Cl)ccc32)[C@@H](O)C1]

To a suspension of Cs(CO₃)₂ (48.3 g, 148.2 mmol, 5 equiv.) in DMF (350 mL, 50 V) previously stirred during 1 h at 80° C. was added 3-chloro-6-fluorocarbazole (1.0 mg, 4.55 mmol, 1 equiv.). The resulting mixture was stirred 1 h at 80° C., then 1-Boc-3,4-epoxypiperidine (906 mg, 4.55 mmol, 1 equiv.) was added. The mixture was stirred at 80° C. during 12 to 72 h and was then allowed to cool to rt. The mixture was filtrated through a plug of celite, concentrated under reduced pressure and purified by Column chromatography (EtOAC 15 to 50% in n-heptan). The resulting two fractions were concentrated under reduced pressure to afford separated regioisomer, Trans-4-(3-Chloro-6-fluoro-carbazol-9-yl)-3-hydroxy-piperidine-1-carboxylic acid tert-butyl ester as a white powder.

EXAMPLE 2 trans-3-(3-Chloro-6-fluoro-carbazol-9-yl)-4-hydroxy-piperidine-1-carboxylic acid tert-butyl ester

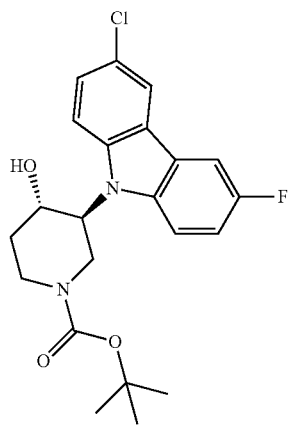 [SMILES: CC(C)(C)OC(=O)N1CC[C@H](O)[C@@H](n2c3ccc(F)cc3c3cc(Cl)ccc32)C1]

Trans-3-(3-Chloro-6-fluoro-carbazol-9-yl)-3-hydroxy-piperidine-1-carboxylic acid tert-butyl ester was obtained as a white powder according to general procedure C, 3-chloro-6-fluorocarbazole.

General Procedure D for Examples 3 to 16

EXAMPLE 3

(3S,4S)-4-(3-Chloro-6-fluoro-carbazol-9-yl)-piperidin-3-ol hydrochloride salt

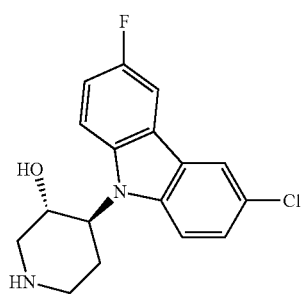

To a solution of Intermediate 7 (150 mg, 0.36 mmol, 1 equiv.) in MeOH (5 mL) was added a solution of HCl (4 M, 1.34 mL, 5.37 mmol, 15 equiv) in dioxane. The reaction was stirred at rt during 5 h then the mixture was concentrated under reduced pressure to afford (3S,4S)-4-(3-Chloro-6-fluoro-carbazol-9-yl)-piperidin-3-ol hydrochloride (120 mg, 0.34 mmol, 94.4%) as a white powder.

EXAMPLE 4

(3R,4R)-4-(3-Chloro-6-fluoro-carbazol-9-yl)-piperidin-3-ol hydrochloride salt

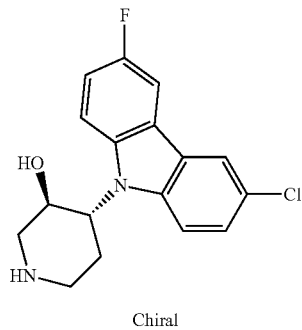 [SMILES: O[C@@H]1CNCC[C@H]1n1c2ccc(F)cc2c2cc(Cl)ccc21]

Chiral (3R,4R)-4-(3-Chloro-6-fluoro-carbazol-9-yl)-piperidin-3-ol hydrochloride (127 mg, 0.34 mmol, 94.3%) was obtained as a white powder following general procedure D.

EXAMPLE 5

Trans-4-(3,6-Dichloro-carbazol-9-yl)-piperidin-3-ol hydrochloride salt

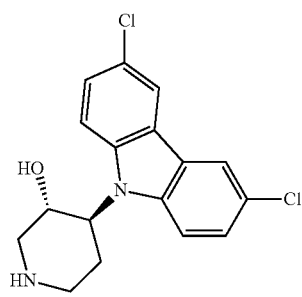

To a suspension of $Cs(CO_3)_2$ (1584.03 mg; 4.86 mmol; 5.74 eq.) in DMF (11.00 ml.) sirred during 1 h at 80° C. was added 36-Dichloro-9H-carbazole (200.00 mg; 0.85 mmol; 1.00 eq.). The mixture was stirred 1 h at 80° C. then 7-Oxa-3-aza-bicyclo[4.1.0]heptane-3-carboxylic acid tert-butyl ester (202.54 mg; 1.02 mmol; 1.20 eq.) was added. The mixture was stirred 15 h at 80° C. then the reaction was cooled to rt and filtrated. The solvent was evaporated and the crude mixture was purified by Chromatography on silica gel (EA 15 to 35% in heptane). The first fraction was then concentrated under reduced pressure and the resulting powder was stirred at rt in a solution of HCl (1.25 N in MeOH, 5 mL) to afford Trans-4-(3,6-Dichloro-carbazol-9-yl)-piperidin-3-ol hydrochloride salt as a white powder.

EXAMPLE 6

(3S,4S)-4-(3,6-Dichloro-carbazol-9-yl)-piperidin-3-ol hydrochloride salt

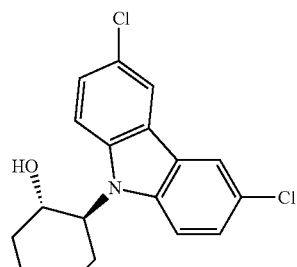

Chiral (3S,4S)-4-(3,6-Dichloro-carbazol-9-yl)-piperidin-3-ol hydrochloride was obtained as a white powder following general procedure D.

EXAMPLE 7

(3R,4R)-4-(3,6-Dichloro-carbazol-9-yl)-piperidin-3-ol hydrochloride salt

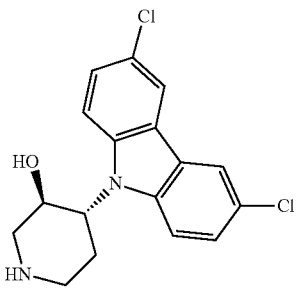

Chiral (3R,4R)-4-(3,6-Dichloro-carbazol-9-yl)-piperidin-3-ol hydrochloride salt (900 mg, 81.1%) was obtained as a white powder following general procedure D.

EXAMPLE 8

Trans-3-(3,6-Dichloro-carbazol-9-yl)-4-hydroxy-piperidine-4-ol hydrochloride salt

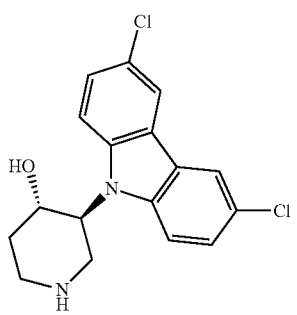 [SMILES: O[C@H]1CCNC[C@@H]1n1c2ccc(Cl)cc2c2cc(Cl)ccc21]

Trans-3-(3,6-Dichloro-carbazol-9-yl)-4-hydroxy-piperidine-4-ol hydrochloride salt was obtained was obtained as a white powder following general procedure D using intermediate 9.

EXAMPLE 9

(3S,4S)-4-(3,6-Difluoro-carbazol-9-yl)-piperidin-3-ol hydrochloride salt

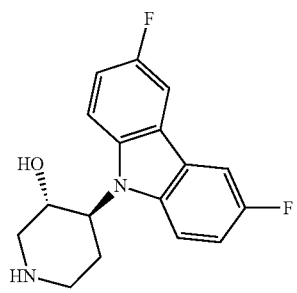

Chiral (3S,4S)-4-(3,6-Difluoro-carbazol-9-yl)-piperidin-3-ol hydrochloride salt (115.00 mg; 91%) was obtained as a white powder according to general procedure D using Intermediate 4.

EXAMPLE 10

(3R,4R)-4-(3,6-Difluoro-carbazol-9-yl)-piperidin-3-ol hydrochloride salt

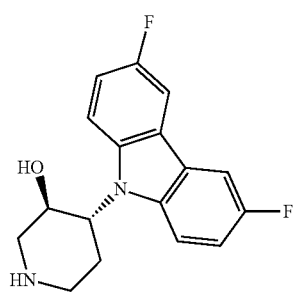

Chiral (3R,4R)-4-(3,6-Difluoro-carbazol-9-yl)-piperidin-3-ol hydrochloride salt (120 mg, 95%) was obtained as a white powder according to general procedure D using intermediate 5.

EXAMPLE 11

3,6-Dichloro-9-((3R,4S)-3-fluoro-piperidin-4-yl)-9H-carbazole hydrochloride salt

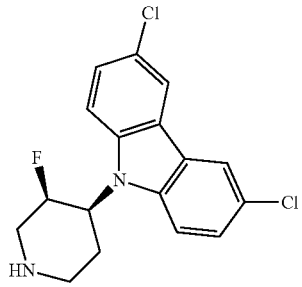

Chiral 3,6-Dichloro-9-((3R,4S)-3-fluoro-piperidin-4-yl)-9H-carbazole hydrochloride salt (12 mg, 70%) was obtained as a white powder according to general procedure D using intermediate 10.

EXAMPLE 12

3-Chloro-6-fluoro-9-((3S,4R)-3-fluoro-piperidin-4-yl)-9H-carbazole hydrochloride call

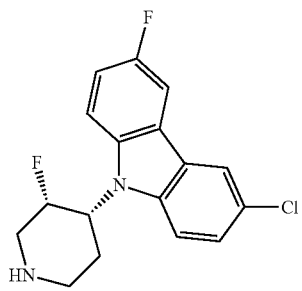

Chiral

3-Chloro-6-fluoro-9-((3S,4R)-3-fluoro-piperidin-4-yl)-9H-carbazole hydrochloride salt was obtained as a white powder according to general procedure D using intermediate 11.

EXAMPLE 13

3-Chloro-6-fluoro-9-((3R,4S)-3-fluoro-piperidin-4-yl)-9H-carbazole hydrochloride salt

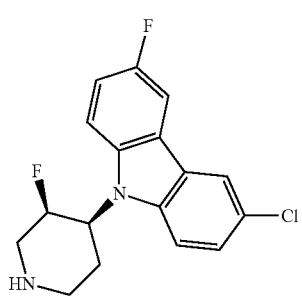

Chiral

3-Chloro-6-fluoro-9-((3R,4S)-3-fluoro-piperidin-4-yl)-9H-carbazole hydrochloride salt (30 mg, 79%) was obtained as a white powder according to general procedure D using intermediate 12.

EXAMPLE 14

(3S,4S)-1-Cyclohexyl-3-(3,6-dichloro-carbazol-9-yb-piperidin-4-ol

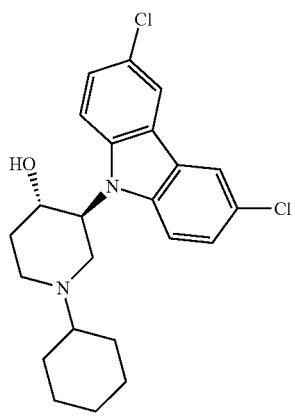 [SMILES: O[C@H]1CCN(C2CCCCC2)C[C@@H]1n1c2ccc(Cl)cc2c2cc(Cl)ccc21]

To a solution of (3S,4S)-3-(3,6-Dichloro-carbazol-9-yl)-piperidin-4-ol (example 9)(20.00 mg; 0.06 mmol; 1.00 eq in DCM (1.00 ml; 15.66 mmol; 262.48 eq.) was added cyclohexanone (0.01 ml; 0.06 mmol; 1.00 eq.) and sodium triacetoxyborohydride (18.97 mg; 0.09 mmol; 1.50 eq.). The reaction was stirred at rt during 15 h. After completion of the reaction, the mixture was filtrated and purified by flash chromatography (EA 0 to 100% in heptane) to give the title compound as a white powder (20 mg 80%).

EXAMPLE 15

(3R,4R)-4-Carbazol-9-yl-piperidin-3-ol hydrochloride salt

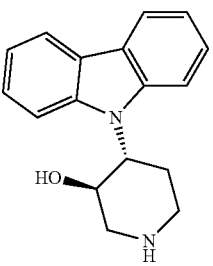

Chiral (3R,4R)-4-Carbazol-9-yl-piperidin-3-ol hydrochloride salt was obtained as a white powder according to general procedure D using intermediate 13.

EXAMPLE 16

(3S,4S)-4-Carbazol-9-yl-piperidin-3-ol hydrochloride salt

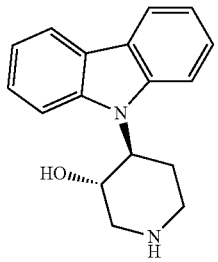

Chiral (3S,4S)-4-Carbazol-9-yl-piperidin-3-ol hydrochloride salt (261 mg, 70%) was obtained as a white powder according to general procedure D using intermediate 14.

| compounds | Yield | $^1$H NMR | HPLC | UPLC/MS |
|---|---|---|---|---|
| Example 1 | | $^1$H NMR (DMSO-d$_6$) δ 8.31 (br s, 1H), 8.09 (br s, 1H), 7.84-7.59 (m, 2H), 7.54-7.19 (m, 2H), 5.19 (d, J = 4.2 Hz, 1H), 4.76-4.51 (m, 1H), 4.32-4.15 (m, 2H), 4.14-4.01 (m, 1H), 3.02 (br s, 1H), 2.74 (br s, 1H), 2.39-2.21 (m, 1H), 1.92-1.76 (m, 1H), 1.47 (s, 9H). | Rt 5.38 min (Purity: 99.6%) | 477.0 ([M + (CH3CO2)]$^-$) |

-continued

| compounds | Yield | ¹H NMR | HPLC | UPLC/MS |
|---|---|---|---|---|
| Example 2 | | ¹H NMR (DMSO-d₆) δ 8.32 (br s, 1H), 8.10 (d, J = 8.9 Hz, 1H), 7.93 (br s, 1H), 7.65 (br s, 1H), 7.54-7.22 (m, 2H), 4.97 (d, J = 5.5 Hz, 1H), 4.64-4.42 (m, 1H), 4.42-4.20 (m, 1H), 4.15-3.79 (m, 2H), 3.65 (br s, 1H), 3.16 (br s, 1H), 2.19-1.94 (m, 1H), 1.68-1.51 (m, 1H), 1.41 (s, 9H). | Rt 5.29 min (Purity: 98.8%) | 477.0 ([M + (CH3CO2)]⁻) |
| Example 3 Chiral | 94.4% | ¹H NMR (DMSO-d₆) δ 9.08 (br s, 2H), 8.33 (s, 1H), 8.19-7.89 (m, 1H), 7.86-7.61 (m, 1H), 7.61-7.18 (m, 1H), 5.50 (d, J = 5.4 Hz, 1H), 4.99-4.43 (m, 2H), 3.68-3.41 (m, 2H), 3.24-3.03 (m, 1H), 2.99-2.62 (m, 2H), 2.00 (d, J = 13.5 Hz, 1H) | Rt 3.24 min (Purity: 99.7%) | 319.3 ([M + H]⁺) |
| Example 4 Chiral | 94.3% | ¹H NMR (DMSO-d₆) δ 9.17 (br s, 2H), 8.33 (s, 1H), 8.16-7.86 (m, 1H), 7.71 (br s, 1H), 7.49 (d, J = 8.4 Hz, 1H), 7.42-7.23 (m, 1H), 5.51 (d, J = 5.4 Hz, 1H), 5.12-4.46 (m, 2H), 3.58-3.39 (m, 2H), 3.26-3.04 (m, 1H), 3.02-2.66 (m, 2H), 2.11-1.83 (m, 1H) | Rt 3.23 min (Purity: 99.8%) | 319.4 ([M + H]⁺) |
| Example 5 | | ¹H NMR (DMSO-d₆) δ 8.35 (br s, 2H), 7.70 (br s, 2H), 7.46 (br s, 2H), 5.20 (d, J = 4.6 Hz, 1H), 4.70-4.60 (m, 1H), 4.38-3.95 (m, 3H), 3.34 (s, 1H), 3.27-2.86 (m, 1H), 2.74 (br s, 1H), 2.46-2.27 (m, 1H), 1.90-1.80 (m, 1H), 1.47 (s, 9H) | Rt 3.42 min (Purity: 96.4%) | 335.2 ([M + H]⁺) |

| compounds | Yield | ¹H NMR | HPLC | UPLC/MS |
|---|---|---|---|---|
| Example 6 (Chiral, structure) | | ¹H NMR (DMSO-d₆) δ 9.88 (br s, 1H), 9.34 (br s, 1H), 8.54-8.25 (m, 2H), 8.25-8.02 (m, 1H), 7.82-7.61 (m, 1H), 7.61-7.33 (m, 2H), 5.53 (d, J = 4.8 Hz, 1H), 4.96-4.61 (m, 2H), 3.60-3.28 (m, 2H), 3.21 (s, 1H), 3.05-2.71 (m, 2H), 2.15-1.75 (m, 1H) | Rt 3.42 min (Purity: 96.4%) | 335.2 ([M + H]⁺) |
| Example 7 (Chiral, structure) | 81.1% | ¹H NMR (DMSO-d₆) δ 9.85 (brs, 1H), 9.31 (br s, 1H), 8.54-8.20 (m, 2H), 8.20-7.97 (m, 1H), 7.88-7.59 (m, 1H), 7.57-7.28 (m, 2H), 5.53 (d, J = 4.8 Hz, 1H), 4.97-4.54 (m, 2H), 3.63-3.31 (m, 2H), 3.31-3.17 (m, 1H), 3.05-2.71 (m, 2H), 2.13-1.82 (m, 1H) | Rt 3.43 min (Purity: 99.1%) | 335.2 ([M + H]⁺) |
| Example 8 (structure) | | ¹H NMR (DMSO-d₆) δ 8.34 (d, J = 2.4 Hz, 2H), 7.75 (d, J = 52.2 Hz, 2H), 7.45 (d, J = 9.1 Hz, 2H), 4.83 (s, 1H), 4.61-4.23 (m, 2H), 3.35 (s, 1H), 3.07-2.83 (m, 2H), 2.83-2.60 (m, 1H), 2.31-2.12 (m, 1H), 2.08-1.89 (m, 1H), 1.64-1.37 (m, 1H) UPLC MS: (max plot) 96%; Rt (min) Area % BPM 1.44 95.95 376.2, 393.3. | Rt 3.06 min (Purity: 89.1%) | 335.2 ([M + H]⁺) |
| Example 9 (Chiral, structure) | 91% | ¹H NMR (DMSO-d₆) δ 9.18 (br s, 1H), 8.35-7.87 (m, 4H), 7.69 (br s, 1H), 7.35 (td, J = 9.0, 3.0 Hz, 2H), 5.49 (d, J = 5.3 Hz, 1H), 4.95-4.40 (m, 2H), 3.55-3.38 (m, 2H), 3.27-3.07 (m, 1H), 2.97-2.70 (m, 2H), 2.08-1.92 (m, 1H) | Rt 2.98 min (Purity: 99.8%) | 303.2 ([M + H]⁺) |

-continued

| compounds | Yield | ¹H NMR | HPLC | UPLC/MS |
|---|---|---|---|---|
| Example 10 (Chiral) | 95% | ¹H NMR (DMSO-d₆) δ 9.18 (br s, 1H), 8.35-7.87 (m, 4H), 7.69 (br s, 1H), 7.35 (td, J = 9.0, 3.0 Hz, 2H), 5.49 (d, J = 5.3 Hz, 1H), 4.95-4.40 (m, 2H), 3.55- 3.38 (m, 2H), 3.27-3.07 (m, 1H), 2.97-2.70 (m, 2H), 2.08- 1.92 (m, 1H) | Rt 2.98 min (Purity: 99.7%) | 303.2 ([M + H]⁺) |
| Example 11 (Chiral) | 70% | | Rt 3.88 min (Purity: 97.5%) | 337.3 ([M + H]⁺) |
| Example 12 (Chiral) | | ¹H NMR (DMSO-d₆) δ 9.76 (br s, 2H), 8.36 (s, 1H), 8.14 (d, J = 10.0 Hz, 2H), 7.82 (br s, 2H), 7.62-7.46 (m, 1H), 7.39 (td, J = 8.7, 1.5 Hz, 1H), 5.97-5.76 (m, 0.5 H), 5.76-5.57 (m, 0.5 H), 5.48-5.21 (m, 1H), 3.96-3.73 (m, 1H), 3.51 (d, J = 12.4 Hz, 1H), 3.26 (d, J = 11.4 Hz, 2H), 3.08-2.80 (m, 1H), 2.25-1.95 (m, 1H) | Rt 3.61 min (Purity: 98.3%) | 321.3 ([M + H]⁺) |
| Example 13 (Chiral) | 79% | ¹HNMR v 9.46 (br s, 2H), 8.36 (s, 1H), 8.14 (d, J = 8.8 Hz, 1H), 8.06-7.63 (m, 2H), 7.54 (dd, J = 8.7, 2.1 Hz, 1H), 7.41 (td, J = 8.7, 2.1 Hz, 1H), 5.91-5.70 (m, 0.5 H), 5.70-5.51 (m, 0.5 H), 5.46-5.16 (m, 1H), 3.97-3.74 (m, 1H), 3.56 -3.40 (m, 1H), 3.29-3.11 (m, 1H), 3.01-2.74 (m, 1H), 2.15 (d, J = 11.7 Hz, 1H) | Rt 3.63 min (Purity: 93.5%) | 321.3 ([M + CH3CO2]⁻) |

-continued

| compounds | Yield | ¹H NMR | HPLC | UPLC/MS |
|---|---|---|---|---|
| Example 14 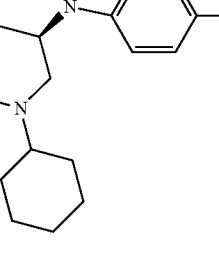 | 80% | ¹H NMR (CDCl₃) δ 8.00 (d, J = 8.5 Hz, 2H), 7.61-7.29 (m, 3H), 4.78-4.37 (m, 2H), 3.29-2.93 (m, 3H), 2.69-2.34 (m, 2H), 2.32-2.12 (m, 1H), 1.95-1.70 (m, 8H), 1.62 (d, J = 12.0 Hz, 1H), 1.46-0.94 (m, 5H) | Rt 3.93 min (Purity: 94.9%) | 417.2 ([M + H]⁺) |
| Example 15 Chiral 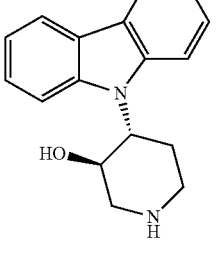 | | ¹H NMR (400 MHz, DMSO-d6): δ 9.59 (br s, 1H), 9.14 (br s, 1H), 8.21-8.10 (m, 2H), 8.08-7.92 (m, 1H), 7.75-7.60 (m, 1H), 7.42 (t, J = 7.16 Hz, 2H), 7.19 (t, J = 7.16 Hz, 2H), 5.47 (d, J = 5.16 Hz, 1H), 4.82-4.79 (m, 2H), 3.47-3.44 (m, 2H), 3.23-3.17 (m, 1H), 2.92-2.89 (m, 2H), 1.98-1.94 (m, 1H). | RT 4.9 min (Purity: 98.5%) | 267.0 [(M + H)]+ |
| Example 16 Chiral 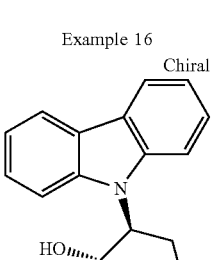 | 70% | ¹HNMR (400 MHz, DMSO-d6): δ 9.53 (br s, 1H), 9.11 (br s, 1H), 8.21-8.15 (m, 2H), 8.09-7.94 (m, 1H), 7.74-7.60 (m, 1H), 7.42 (t, J = 7.16 Hz, 2H), 7.19 (t, J = 7.20 Hz, 2H), 5.47 (d, J = 5.04 Hz, 1H), 4.82-4.79 (m, 2H), 3.47-3.44 (m, 2H), 3.25-3.15 (m, 1H), 2.89-2.88 (m, 2H), 1.96 (d, J = 12.56 Hz, 1H). | RT 4.9 min (Purity: 94.2%) | 267.0 [(M + H)]+ |

As further examples compounds no. 41 to 70 were synthesized and analysed using following methods and procedures:

LCMS-Analysis:

Method A:

Method: A-10mM Ammonium acetate in water; B-ACN; Flow: 1.2 mL/min.

Column-ZOXBAX XDB C18 (50×4.6 mm-5 μm) positive& negative mode.

Method B:

Method: A-0.1% HCOOH; B-CAN; Flow: 1.2 mL/min.

Column Atlantis dC18 (50×4.6 mm-5 μm) positive& negative mode.

Method C:

Method: A-0.1% HCOOH; B-MEOH; Flow: 1.2 mL/min.

Column-Atlantis dC18 (50×4.6 mm-5 μm) dual MODE

GCMS-Analysis:

Method A:

AcqMethod DB5MS SPLITTER 1.M

Method B:

AcqMethod HP-1 MS

HPLC Analysis:

Method A:

Method: A: 0.1% TFA in water; B: ACN; Flow: 1.0 mL/min

Column: WELCHROM C18 (250×4.6 mm-5 μm)

Method B:
  Method: A: 0.1% TFA in water; B:ACN; Flow:1.0 mL/min
  Column: Atlantis dC18 (250×4.6 mm-5 µm)
Method C:
  Method: A:0.1% TFA in water B:Methanol; Flow: 1.0 mL/min
  Column: XDB-C18 (50×4.6 mm-1.8 µm)
CHIRALHPLC:
Method A:
  Method: A: HEXANE:IPA (80:20); Flow: 1.0 mL/min
  Column: CHIRAL PAK IA (250×4.6 mm-5µ)
Method B:
  Method: A: HEXANE: ETHANOL (90:10); Flow: 1.0 mL/min
  Column: CHIRAL PAK AD-H (250×4.6 mm-0.5µ)
Method C:
  Method: A: HEXANE: ETHANOL (90:10); Flow: 1.0 mL/min.
  Column: PHENOMENEX LUX CELL ULOSE-4 (250×4.6 mm-5µ)
Method D:
  Method:Mobile Phase A: 0.1% DEA in HEXANE:IPA (90: 10)
  Column: CHIRAL PAK IC (250×4.6 mm-5µ)
Method E:
  Method: Mobile Phase A: HEXANE:ETHANOL (95:05)
  Column: CHIRAL PAK IC (250×4.6 mm-5µ)

Int A1
Synthesis of tert-Butyl 7-oxa-3-azabicyclo[4.1.0]heptane-3-carboxylate

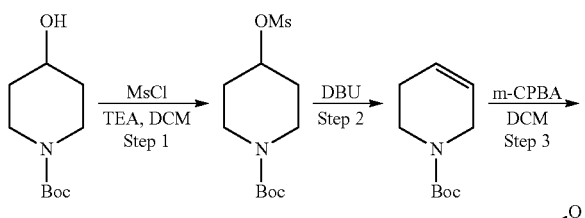

Step 1: To a solution containing tert-butyl 4-hydroxypiperidine-1-carboxylate (25.0 g, 124 mmol) and triethylamine (18.86 g, 186 mmol) in dichloromethane (250 mL) at 0° C., was added methanesulfonylchloride (15.6 g, 136 mmol) dropwise. After complete addition, reaction mixture warmed to room temperature and stirred for 16 h. The reaction mixture was diluted with dichloromethane, washed with saturated sodium bicarbonate solution and water. The organic layer was dried over anhydrous sodium sulfate, filtered, and concentrated to obtain the mesylatedcompound (33.0 g, 96.2%) as a brown solid.

$^1$H NMR (400 MHz, CDCl$_3$): δ, 4.85-4.90 (m 1H), 3.68-3.71 (m, 2H), 3.26-3.32 (m, 2H), 3.03 (s, 3H), 1.93-1.98 (m, 2H), 1.78-1.85 (m, 2H), 1.45 (s, 9H).

Step 2: 4-Methanesulfonyloxy-piperidine-1-carboxylic acid tert-butyl ester (25.0 g, 89 mmol) in DBU (50 mL) was heated at 80° C. for 16 h. The reaction mixture was diluted with water, extracted with diethyl ether, and washed the organic layer with 1 N hydrochloric acid and saturated sodium bicarbonate solution. The organic layer was dried over anhydrous sodium sulfate, filtered, and concentrated to obtain the reduced compound (15.0 g, 92%) as a brown oil.

$^1$H NMR (400 MHz, CDCl$_3$): δ 5.81 (brs, 1H), 5.65 (br s, 1H), 3.87 (s, 2H), 3.47 (t, J=7.84 Hz, 2H), 2.12 (br s, 2H), 1.46 (s, 9H).

Step 3: A solution of 3-chloroperoxybenzoic acid (21.18 g, 122.7 mmol) in dichloromethane (150 mL) was added to a solution of N-boc-1,2,3,6-tetrahydropyridine (15.0 g, 81.8 mmol) in dichloromethane (150 mL) at 0° C. The mixture was stirred at room temperature overnight and washed with saturated solution of Na$_2$CO$_3$. The organic layer was separated, dried (Na$_2$SO$_4$), filtered and the solvent evaporated in vacuoand purified by column chromatography using silicagel 60-120 mesh to yield the title compound IntA1 (13.0 g, 80%).

$^1$H NMR (400 MHz, CDCl$_3$): 3.93 (s, 1H), 3.83 (s, 1H), 3.70 (s, 1H), 3.44 (s, 1H), 3.30 (d, J=2.00 Hz, 1H), 3.14 (s, 1H), 1.88-1.89 (m, 1H), 1.46 (s, 9H).

3,6-difluoro-9H-carbazole Int B1 is prepared according to the protocol of Bedford, Robin B. et al. *Tetrahedron* 2008, 64, 6038-6050.

Synthesis of Compound No. 44, Compound No. 46, Compound No. 47, Compound No. 48, Compound No. 69

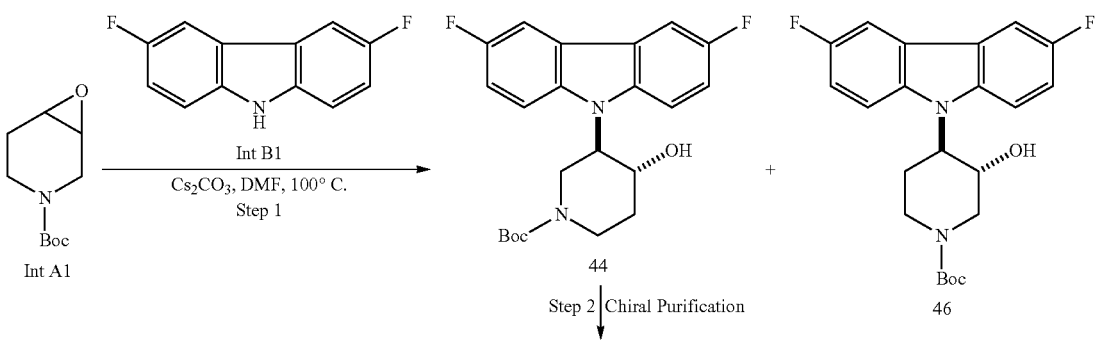

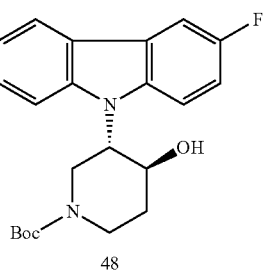
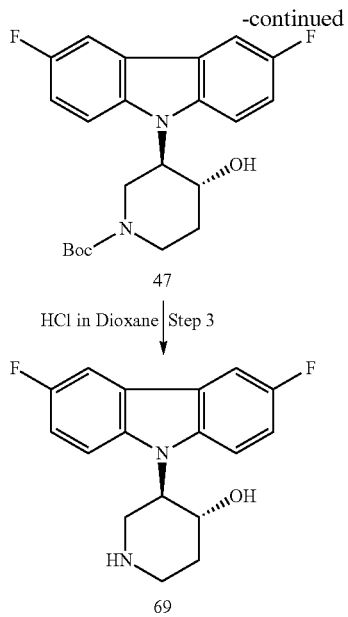

COMPOUND NO. 44: trans-tert-butyl 3-(3,6-difluoro-9H-carbazol-9-yl)-4-hydroxypiperidine-1-carboxylate COMPOUND NO. 46: trans-tert-butyl 4-(3,6-difluoro-9H-carbazol-9-yl)-3-hydroxypiperidine-1-carboxylate COMPOUND NO. 47: (3R,4R)-tert-butyl 3-(3,6-difluoro-9H-carbazol-9-yl)-4-hydroxypiperidine-1-carboxylate COMPOUND NO. 48: (3S,4S)-tert-butyl 3-(3,6-difluoro-9H-carbazol-9-yl)-4-hydroxypiperidine-1-carboxylate COMPOUND NO. 69: (3R,4R)-3-(3,6-difluoro-9H-carbazol-9-yl)piperidin-4-ol Step 1: To a stirred solution of 3,6-difluoro-9H-carbazole Int B1 (1.0 g, 4.1 mmol) in dry N, N-dimethylformamide (10 mL) was added cesium carbonate (2.49 g, 7.6 mmol) under $N_2$ atmosphere and the reaction mixture was stirred at 100° C. for 1 h. After 1 h, Int A1 (0.82 g, 4.1 mmol) was added to the reaction mixture and the stirring continued at 100° C. for 18 h. After completion, the reaction mass was diluted with water, extracted over ethyl acetate, washed with water, brine solution and dried over anhydrous $Na_2SO_4$. The organicphase was concentrated and the regioisomers were purified by the flash column chromatography (230-400 size mesh) as elution 1 (non polar) (compound No. 46) was regioisomer 1 (0.65 g, 32.8%) and elution 2 (compound No. 44) was the regio-isomer 2 (0.58 g, 29.2%).

Compound No. 46:
LCMS: (Method B) 344.0 (M+H), RT. 6.6 min, 99.19% (Max)
HPLC: (Method C) RT 7.0 min, 99.50% (Max)
$^1$HNMR (300 MHz, DMSO-d6): δ 8.00-8.02 (m, 2H), 7.65 (s, 2H), 7.27 (s, 2H), 5.15 (d, J=4.77 Hz, 1H), 4.01-4.20 (m, 3H), 2.71 (br s, 2H), 1.83-1.85 (m, 1H), 1.45 (s, 9H).

Compound No. 44:
LCMS: (Method B) 344.0 (M+H), RT. 6.6 min, 99.80% (Max)
HPLC: (Method C) RT 6.99 min, 99.58% (Max)
$^1$HNMR (300 MHz, DMSO-d6): δ 8.02 (d, J=7.86 Hz, 2H), 7.89 (s, 2H), 7.61 (s, 1H), 7.28 (br s, 2H), 4.93 (d, J=5.8 Hz, 1H), 4.47-4.51 (m, 1H), 4.30-4.33 (m, 1H), 3.96 (br s, 2H), 3.64 (s, 1H), 3.15 (br s, 2H), 1.97-2.03 (m, 1H), 1.24 (s, 9H).

Compound No. 47 & Compound No. 48:
The regioisomer 2 compound No. 44 was submitted for chiral preparative purification using Method A and obtained 0.25 g of isomer 1 (compound No. 47) and 0.25 g of isomer 2 (compound No. 48).

Compound No. 47 (Isomer 1):
LCMS: (Method C) 403 (M+H), RT. 3.57 min, 99.02% (Max)
HPLC: (Method B) RT 15.81 min, 98.37% (Max)
CHIRAL HPLC: (Method B)—RT 10.83 min, 99.86% (Max)
$^1$HNMR (400 MHz, DMSO-d6): δ 8.03 (d, J=8.12 Hz, 2H), 7.90 (s, 1H), 7.61 (s, 1H), 7.28 (br s, 1H), 4.94 (d, J=5.8 Hz, 1H), 4.46-4.55 (m, 1H), 4.28-4.35 (m, 1H), 3.98 (br s, 2H), 3.64 (br s, 1H), 3.15 (br s, 1H), 2.00-2.05 (m, 1H), 1.51-1.57 (m, 1H), 1.40 (s, 9H).

Compound No. 48 (Isomer 2):
LCMS: (Method C) 403 (M+H), RT. 3.57 min, 99.12% (Max)
HPLC: (Method B) RT 15.82 min, 99.86% (Max)
CHIRAL HPLC: (Method B)—RT 13.96 min, 88.63% (Max)
$^1$HNMR (400 MHz, DMSO-d6): δ 8.03 (d, J=8.52 Hz, 2H), 7.89 (s, 1H), 7.61 (s, 1H), 7.28 (brs, 1H), 4.93-4.95 (m, 1H), 4.46-4.54 (m, 1H), 4.28-4.35 (m, 1H), 3.99-4.04 (m, 2H), 3.63 (br s, 1H), 3.12 (br s, 1H), 1.98-2.05 (m, 1H), 1.51-1.58 (m, 1H), 1.40 (s, 9H).

Compound No. 69:
To a stirred solution of compound No. 47 (Isomer 1) (0.09 g) in dioxane, was added HCl in dioxane after cooling to 0° C. and stirred at room temperature overnight. After completion, the reaction mixture was concentrated to remove dioxane and given diethyl ether wash to get compound No. 69 as HCl salt (0.073 g, 93%).
LCMS: (Method B) 303 (M+H), RT. 2.18 min, 99.54% (Max)
HPLC: (Method B) RT 8.73 min, 99.34% (Max)
$^1$HNMR (400 MHz, DMSO-d6): δ 9.29 (s, 2H), 8.01-8.06 (m, 3H), (m, 1H), 7.58 (br s, 1H), 7.34-7.37 (m, 2H), 5.24 (s, 1H), 4.87-4.94 (m, 1H), 4.58-4.61 (m, 1H), 3.73-3.79 (m, 1H), 3.39-3.43 (m, 3H), 2.17-2.19 (m, 1H), 1.87-1.92 (m, 1H).

Same protocol was followed for all compounds which involved de-protection of the boc group.

Synthesis of Compound No. 49, Compound No. 50, Compound No. 51, Compound No. 52, Compound No. 53, Compound No. 45

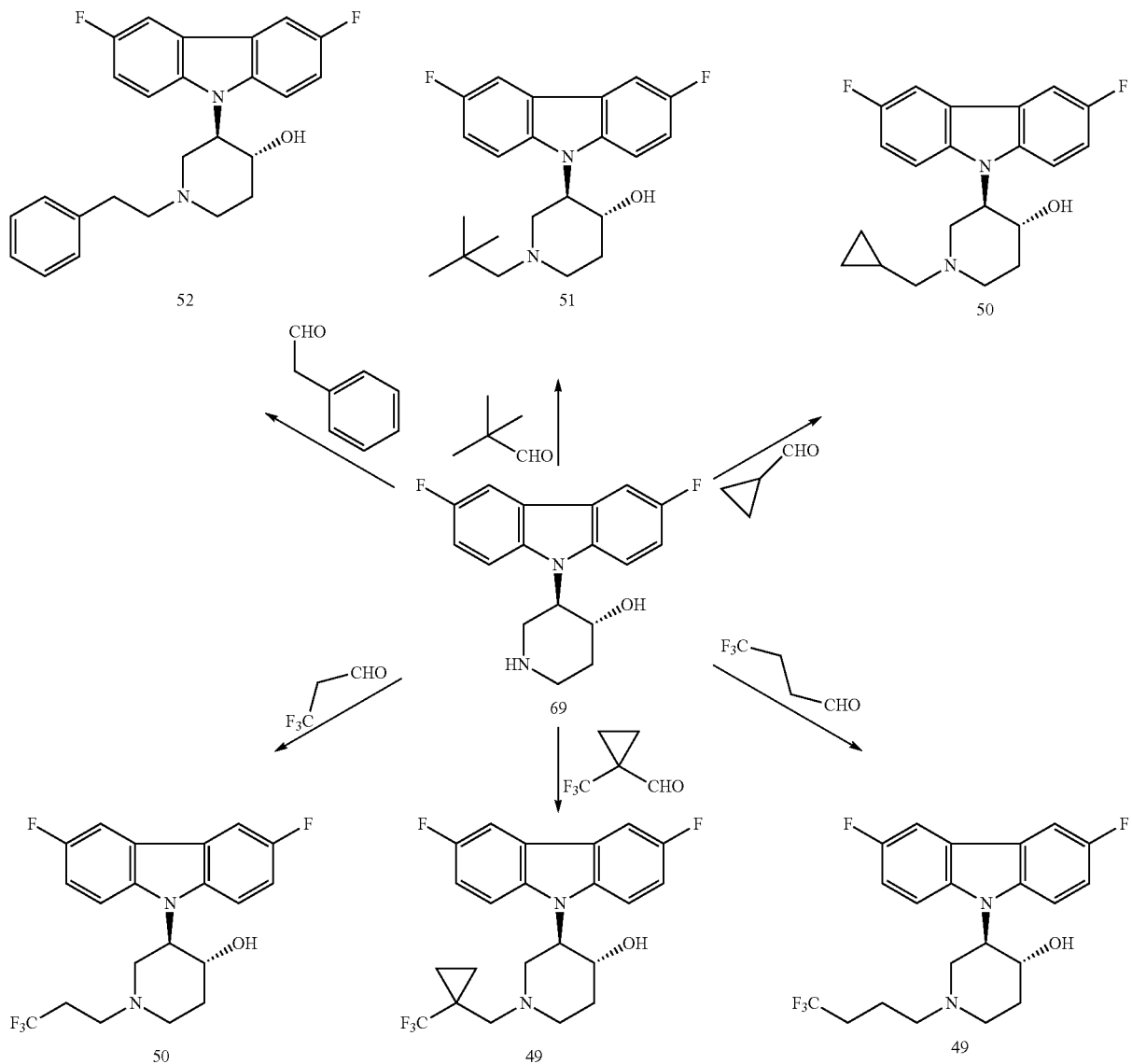

COMPOUND NO. 51: (3R,4R)-3-(3,6-difluoro-9H-carbazol-9-yl)-1-neopentylpiperidin-4-ol COMPOUND NO. 50: (3R,4R)-1-(cyclopropylmethyl)-3-(3,6-difluoro-9H-carbazol-9-yl)piperidin-4-ol COMPOUND NO. 49: (3R,4R)-3-(3,6-difluoro-9H-carbazol-9-yl)-1-(4,4,4-trifluorobutyl)piperidin-4-ol COMPOUND NO. 53: (3R,4R)-3-(3,6-difluoro-9H-carbazol-9-yl)-1-((1-(trifluoromethyl)cyclopropyl)methyl)piperidin-4-ol COMPOUND NO. 45: (3R,4R)-3-(3,6-difluoro-9H-carbazol-9-yl)-1-(3,3,3-trifluoropropyl)piperidin-4-ol COMPOUND NO. 52: (3R,4R)-3-(3,6-difluoro-9H-carbazol-9-yl)-1-phenethylpiperidin-4-ol Compound No. 49:

To the stirred solution of compound No. 69 (0.04 g, 0.13 mmol), and 4,4,4,-trifluorobutyraldehyde (20.02 mg, 0.16 mmol) in methanol (1 mL), was added one drop of acetic acid and sodium cyanoborohydride resin (loading capacity: 2.4 mmol/g, 0.082 g, 0.199 mmol) and stirred at room temperature for overnight. After the completion of the reaction, reaction mixture was filtered through syringe pad, washed with methanol, concentrated and purified by column chromatography using silica gel 230-400 mesh to get compound No. 49 (0.03 g, 55%).

LCMS: (Method B) 413 (M+H), RT. 2.64 min, 99.67% (Max)

HPLC: (Method A) RT 11.29 min, 99.78% (Max)

$^1$HNMR (400 MHz, DMSO-d6): δ 8.02 (d, J=8.71 Hz, 1H), 7.62 (br s, 1H), 7.82 (br s, 1H), 7.27 (br s, 2H), 4.83 (d, J=5.63 Hz, 1H), 4.43-4.49 (m, 1H), 4.30-4.38 (m, 1H), 2.88 (d, J=8.19 Hz, 3H), 2.34-2.66 (m, 2H), 2.20-2.31 (m, 3H), 1.99-2.05 (m, 1H), 1.58-1.71 (m, 3H).

Same protocol was followed for all compounds which involved reductive amination.

Compound No. 50: (0.03 g, 63.8%).

LCMS: (Method B) 357 (M+H), RT. 2.49 min, 97.57% (Max)

HPLC: (Method A) RT 10.70 min, 99.67% (Max)

¹HNMR (400 MHz, DMSO-d6): δ 7.94-8.09 (m, 2H), 7.77-7.85 (m, 1H), 7.57-7.70 (m, 1H), 7.18-7.37 (m, 2H), 4.82 (d, J=5.6 Hz, 1H), 4.46-4.49 (m, 1H), 4.32-4.36 (m, 1H), 3.01-3.04 (m, 2H), 2.88-2.91 (m, 1H), 2.26-2.48 (m, 3H), 1.99-2.03 (m, 1H), 1.67-1.70 (m, 1H), 0.83-0.88 (m, 1H), 0.38-0.43 (m, 2H), 0.01-0.05 (m, 2H).

Compound No. 51: (0.02 g, 40.5%).

LCMS: (Method B) 373 (M+H), RT. 2.59 min, 98.95% (Max)

HPLC: (Method A) RT 11.17 min, 98.56% (Max)

¹HNMR (400 MHz, DMSO-d6): δ7.99-8.03 (m, 2H), 7.81-7.82 (m, 1H), 7.56-7.58 (m, 1H), 7.24-7.32 (m, 2H), 4.79 (d, J=5.8 Hz, 1H), 4.42-4.48 (m, 1H), 4.30-4.36 (m, 1H), 3.16-3.22 (m, 1H), 2.74-2.80 (m, 2H), 2.60-2.66 (m, 1H), 2.07-2.16 (m, 2H), 1.94-1.97 (m, 1H), 1.65-1.75 (m, 1H), 0.84 (s, 9H).

Compound No. 52: (0.04 g, 75%).

LCMS: (Method B) 407 (M+H), RT. 2.73 min, 94.07% (Max)

HPLC: (Method A) RT 11.65 min, 96.00% (Max)

¹HNMR (400 MHz, DMSO-d6): δ 7.61 (br s, 1H), 7.82 (br s, 1H), 8.03 (br s, 2H) 7.13-7.26 (m, 6H), 4.83 (d, J=5.6 Hz, 1H), 4.44-4.50 (m, 1H), 4.33-4.39 (m, 1H), 2.91-3.00 (m, 3H), 2.73-2.88 (m, 2H), 2.57-2.71 (m, 1H), 2.32-2.41 (m, 1H), 1.98-2.03 (m, 1H), 1.67-1.70 (m, 1H).

Compound No. 45: (0.03 g, 60%).

LCMS: (Method B) 399 (M+H), RT. 2.64 min, 95.45% (Max)

HPLC: (Method B) RT 11.05 min, 97.33% (Max)

¹HNMR (400 MHz, DMSO-d6): δ 8.94 (br s, 1H), 8.03 (br s, 1H), 7.89-7.91 (m, 1H), 7.57 (br s, 1H), 7.28 (br s, 1H), 4.85-4.86 (m, 1H), 4.37-4.56 (m, 2H), 3.01-3.07 (m, 3H), 2.90-2.96 (m, 2H), 1.97-2.05 (m, 1H), 1.70-1.78 (m, 1H).

Compound No. 53: (0.04 g, 56.9%).

LCMS: (Method B) 423.0 (M+H), RT. 2.80 min, 98.8545% (Max)

HPLC: (Method B) RT 11.86 min, 99.12% (Max)

¹HNMR (400 MHz, DMSO-d6): δ 8.01-8.03 (m, 2H), 7.80 (br s, 1H), 7.55 (br s, 1H), 7.29 (br s, 1H), 4.82 5.63 Hz, 1H), 4.33-4.81 (m, 2H), 2.73-2.98 (m, 3H), 2.66-2.87 (m, 1H), 2.32-2.38 (m, 1H), 1.98-2.02 (m, 1H), 1.65-1.68 (m, 1H), 1.23-1.25 (m, 2H), 0.83-0.98 (m, 2H).

Synthesis of Compound No. 41, Compound No. 42, Compound No. 43, Compound No. 63, Compound No. 69, Compound No. 70

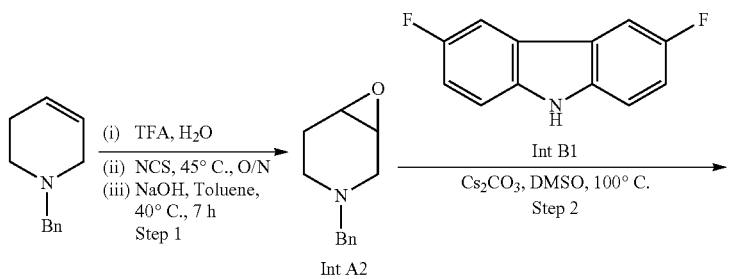

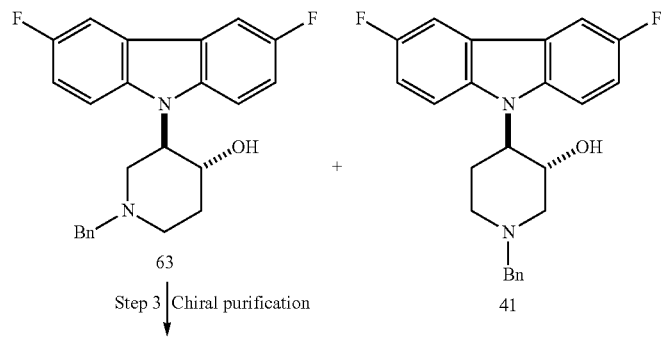

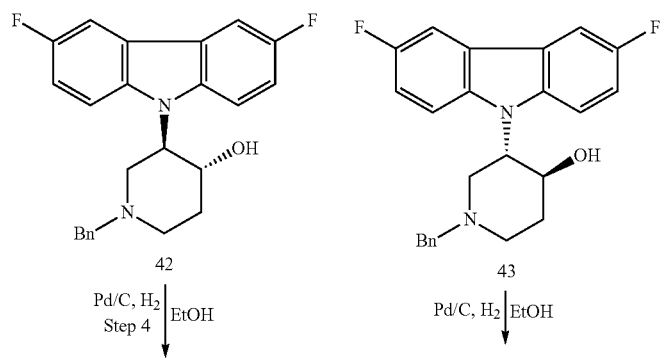

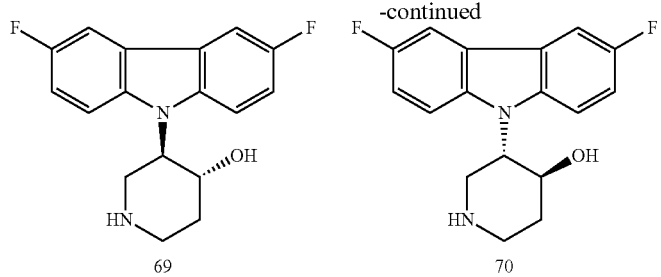

69    70

COMPOUND NO. 63: trans-1-benzyl-3-(3,6-difluoro-9H-carbazol-9-yl)piperidin-4-ol
COMPOUND NO. 41: trans-1-benzyl-4-(3,6-difluoro-9H-carbazol-9-yl)piperidin-3-ol
COMPOUND NO. 42: (3R,4R)-1-benzyl-3-(3,6-difluoro-9H-carbazol-9-yl)piperidin-4-ol
COMPOUND NO. 43: (3S,4S)-1-benzyl-3-(3,6-difluoro-9H-carbazol-9-yl)piperidin-4-ol
COMPOUND NO. 69: (3R,4R)-3-(3,6-difluoro-9H-carbazol-9-yl)piperidin-4-ol
COMPOUND NO. 70: (3S,4S)-3-(3,6-difluoro-9H-carbazol-9-yl)piperidin-4-ol
Int A2 (1-(trifluoromethyl)cyclopropane-1-carbaldehyde) is commercially available.
Step 1:
To a solution of 1-benzyl-1,2,3,6-tetrahydropyridine (0.75 g, 4.3 mmol) in 5 mL water, trifluoroacetic acid (0.33 mL, 4.32 mmol) was added drop wise and stirred. To this reaction mixture, N-chlorosuccinimide (0.69 g, 5.1 mmol) was added little by little over the period of 30 minutes and stirred at 45° C. overnight. After completion of the reaction, the reaction mixture was cooled to 12° C. and added toluene followed by 2.7 g of 48% NaOH solution, stirred at 40° C. for 7 h. After the completion of reaction, toluene layer was separated and aqueous layer was extracted with ethyl acetate and washed with brine. The organic layer was separated, dried over $Na_2SO_4$, concentrated to get 3-benzyl-7-oxa-3-azabicyclo[4.1.0]heptanesInt A2 (0.7 g, 85.4%).
LCMS: (Method. B) 190.0 (M+H), RT. 1.36 min, 96.4% (Max)
$^1$HNMR (400 MHz, CDCl$_3$): δ 7.23-7.31 (m, 5H), 3.49 (s, 2H), 3.23-3.24 (m, 2H), 3.08 (t, J=10.40 Hz, 1H), 2.71 (d, J=12.00 Hz, 1H), 2.26 (d, J=4.00 Hz, 1H), 2.15-2.18 (m, 1H), 2.06 (d, J=3.60 Hz, 2H).
Step 2: To a solution of 3,6-difluoro-9H-carbazole Int B1 (0.35 g, 1.72 mmol) in drydimethyl sulphoxide (5 mL) was added cesium carbonate (0.73 g, 2.24 mmol) under $N_2$ atmosphere and the reaction mixture stirred at 100° C. for 1 h. After 1 h, 3-benzyl-7-oxa-3-azabicyclo[4.1.0]heptanes (0.413 g, 1.72 mmol) was added to the reaction mixture and stirred at 100° C. for 18 h. After completion, the reaction mass was diluted with water, extracted using ethyl acetate, washed with water, brine solution and dried over anhydrous $Na_2SO_4$. Organic phase was concentrated and the regio-isomers were purified by the flash column chromatography (230-400 size mesh) as elution 1 (non polar) was regio-isomer 1 (compound No. 41) (0.3 g, 44.3%) and elution 2 was the regio-isomer 2 (compound No. 63) (0.35 g, 51.7%).

Compound No. 41:
LCMS: (Method B) 393.0 (M+H), RT. 2.6 min, 97.30% (Max)
HPLC: (Method B) RT 12.05 min, 99.11% (Max)
$^1$HNMR (400 MHz, DMSO-d6): δ 7.69 (dd, J=1.60, 8.00 Hz, 2H), 7.54 (s, 2H), 7.32-7.40 (m, 6H), 7.19-7.19 (m, 2H), 4.60 (s, 1H), 4.24-4.26 (m, 1H), 3.69 (s, 2H), 3.36 (s, 1H), 3.09 (d, J=4.12 Hz, 1H), 2.72 (s, 1H), 2.28 (s, 1H), 2.18 (s, 1H), 1.87-1.89 (m, 1H), 1.75 (s, 1H).
Compound No. 63:
LCMS: (Method B) 393.0 (M+H), RT. 2.62 min, 98.99% (Max)
HPLC: (Method B) RT 11.73 min, 99.22% (Max)
$^1$HNMR (300 MHz, DMSO-d6): δ 8.00 (d, J=9.00 Hz, 2H), 7.79 (s, 1H), 7.58 (s, 1H), 7.19-7.29 (m, 7H), 4.85 (dd, J=3.00, Hz, 1H), 4.36 (dd, J=6.00, 12.00 Hz, 2H), 3.51-3.55 (m, 2H), 2.71-2.87 (m, 3H), 2.25-2.29 (m, 2H), 1.98-2.01 (m, 1H), 1.67-1.71 (m, 1H).
Compound No. 42 & Compound No. 43:
The regio-isomer-2 compound No. 68 (0.35 g) was submitted for chiral preparative purification using Method C and obtained 0.12 g of isomer 1 (compound No. 42) and 0.11 g of isomer 2 compound No. 43).
Compound No. 42:
LCMS: (Method B) 393.0 (M+H), RT. 2.61 min, 98.03% (Max)
HPLC: (Method B) RT 11.70 min, 99.78% (Max)
CHIRAL HPLC: (Method C) RT 7.77 min, 100% (Max)
$^1$HNMR (400 MHz, DMSO-d6): δ 8.00 (s, 2H), 7.79 (s, 1H), 7.18-7.19 (m, 7H), 4.85 (s, 1H), 4.38-4.40 (m, 1H), 4.35-4.36 (m, 1H), 3.52-3.56 (m, 2H), 2.81-2.82 (m, 3H), 2.32 (t, J=4.00 Hz, 1H), 1.98-2.00 (m, 1H), 1.65-1.67 (m, 1H).
Compound No. 43:
LCMS: (Method B) 393.0 (M+H), RT. 2.60 min, 99.45% (Max)
HPLC: (Method B) RT 11.68 min, 93.60% (Max)
CHIRAL HPLC: (Method C) RT 15.79 min, 99.91% (Max)
$^1$HNMR (400 MHz, DMSO-d6): δ 8.00 (s, 1H), 7.80 (s, 1H), 7.59 (s, 1H), 7.18-7.19 (m, 7H), 4.84 (s, 1H), 4.51-4.62 (m, 1H), 4.33-4.34 (m, 1H), 3.53-3.56 (m, 2H), 2.81-2.82 (m, 3H), 2.33 (t, J=4.00 Hz, 1H), 2.00 (dd, J=4.40, 10.20 Hz, 1H), 1.65-1.67 (m, 1H).
Compound No. 69:
To the solution of compound No. 42 (0.012 g, 0.31 mmol) in dry methanol (3 mL) was added Pd/C 10% (0.02 g) and kept at $H_2$ atmosphere (bladder) overnight. After the completion of the reaction, reaction mixture was filtered through Celite® and washed with methanol, concentrated to get compound No. 69 (0.05 g, 54.3%).

LCMS: (Method B) 303 (M+H), RT. 2.26 min, 96.85% (Max)
HPLC: (Method A) RT 11.68 min, 95.52% (Max)
SOR: [α] D-15.789° (c-0.095, MeOH, T-23.4° C.)
¹HNMR (400 MHz, DMSO-d6): δ 8.02 (d, J=7.6 Hz, 2H), 7.82 (br s, 1H), 7.61 (br s, 1H), 7.28 (br s, 2H), 3.32-3.34 (m, 4H), 2.95-3.01 (m, 2H), 2.74-2.80 (m, 1H), 2.01-2.04 (m, 1H), 1.52-1.56 (m, 1H).
Compound No. 48: 0.04 g, 47.2%
LCMS: (Method B) 303 (M+H), RT. 2.20 min, 96.09% (Max)
HPLC: (Method A) RT 9.93 min, 98.67% (Max)
SOR: [α]D+15.152° (c-0.099, MeOH, T-23.4° C.)
¹HNMR (400 MHz, DMSO-d6): δ 9.12 (s, 1H), 8.63-8.66 (m, 1H), 7.95-8.07 (m, 3H), 7.52 (br s, 1H), 7.36 (br s, 2H)

Following the addition, the cooling bath was removed and the reaction mixture was stirred for another 4 h at room temperature. The solid precipitated was filtered off, washed with dichloromethane and dried to give 4.4 g of raw 3,6-dichlorocarbazole contaminated with traces of 3-chlorocarbazole. The residue was suspended in 0.1 L of hexane and boiled for 0.5 h to remove the traces of 3-chlorocarbazole. The suspension was filtered, giving pure product (3.0 g, 42.9%).
¹HNMR (400 MHz, DMSO-d6): δ 11.58 (s, 1H), 8.28 (d, J=2.0 Hz, 2H) 7.52 (d, J=8.6 Hz, 2H), 7.42 (dd, J=8.6 Hz, J=2.0 Hz, 2H).

Synthesis of Compound No. 8, Compound No. 66 & Compound No. 67

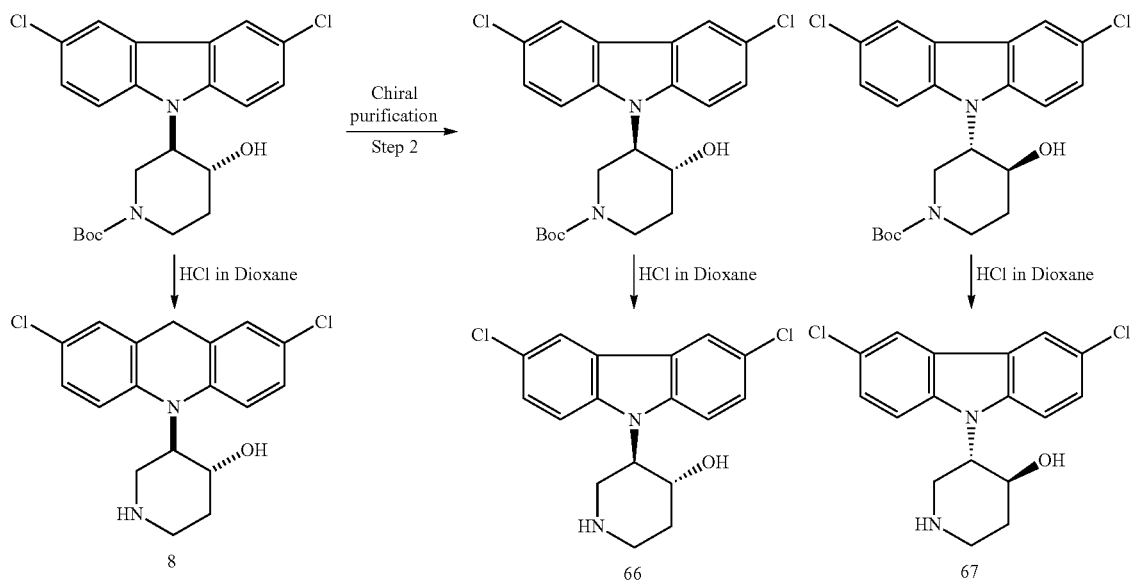

5.18-5.25 (d, J=5.68 Hz, 1H), 4.70-4.77 (m, 1H), 4.56-4.60 (m, 1H), 3.72-3.79 (m, 1H), 3.42-3.48 (m, 3H), 2.18-2.21 (m, 1H), 1.76-1.79 (m, 1H).

Synthesis of 3,6-dichloro-9H-carbazole Int B2

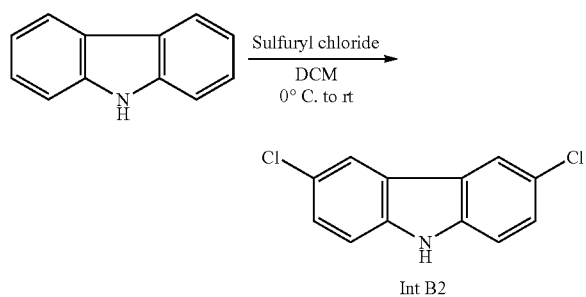

To a 3-neck, 100 mL round-bottomed flask equipped with septum, a mechanical stirrer and a thermometer, was added carbazole (5.0 g, 2.9 mmol) and dichloromethane (50 mL) The suspension was cooled to 0° C. With vigorous stirring, sulfuryl chloride (4.8 mL, 5.9 mmol) was added drop wise at such rate, that the temperature did not exceed 2° C.

COMPOUND NO. 8: trans-3-(3,6-dichloro-9H-carbazol-9-yl)piperidin-4-ol
COMPOUND NO. 66: (3R,4R)-3-(3,6-dichloro-9H-carbazol-9-yl)piperidin-4-ol
COMPOUND NO. 67: (3S,4S)-3-(3,6-dichloro-9H-carbazol-9-yl)piperidin-4-ol Compound No. 8:
Regio-isomer-2 (Racemic) was de-protected using standard protocol and obtained compound No. 8 as HCl salt (0.04 g, 94%).
LCMS: (Method B) 336 (M+H), RT. 2.50 min, 92.90% (max)
HPLC: (Method A) RT 10.71 min, 96.01% (max)

Compound No. 66 & Compound No. 67:
The regio-isomer-2 (0.35 g) was submitted for chiral SFC purification using Method D and obtained 0.13 g of isomer 1 and 0.13 g of isomer 2. After de-protection of the respective individual isomers, compound No. 66 and compound No. 67 were obtained.

Compound No. 66 (Isomer 1): 0.01 g, 91%
LCMS: (Method B) 336 (M+H), RT. 2.54 min, 98.24% (max)
HPLC: (Method B) RT 11.12 min, 98.57% (max)
¹HNMR (400 MHz, DMSO-d6): δ 9.37 (s, 2H), 8.38 (s, 1H), 8.04 (s, 1H), 7.48-7.57 (m, 3H), 5.26 (s, 1H), 4.93-4.96 (m, 1H), 4.59 (t, J=4.44 Hz, 1H), 3.75 (d, J=6.80 Hz, 1H), 3.60 (s, 1H), 3.12 (t, J=4.00 Hz, 3H), 2.18-2.20 (m, 1H), 1.89-1.92 (m, 1H).
Compound No. 67 (Isomer 2): 0.01 g, 91%
LCMS: (Method B) 336 (M+H), RT. 2.54 min, 94.73% (max)
HPLC: (Method B) RT 11.12 min, 94.98% (max)
¹HNMR (400 MHz, DMSO-d6): δ 9.40 (s, 1H), 8.38 (s, 2H), 8.05 (d, J=6.40 Hz, 1H), 7.48-7.56 (m, 3H), 5.28 (s, 1H), 4.95-4.97 (m, 1H), 4.56-4.58 (m, 1H), 3.74-3.77 (m, 1H), 3.57-3.58 (m, 1H), 3.37-3.39 (m, 3H), 2.16-2.18 (m, 1H), 1.91-1.94 (m, 1H).

Synthesis of Compound No. 54

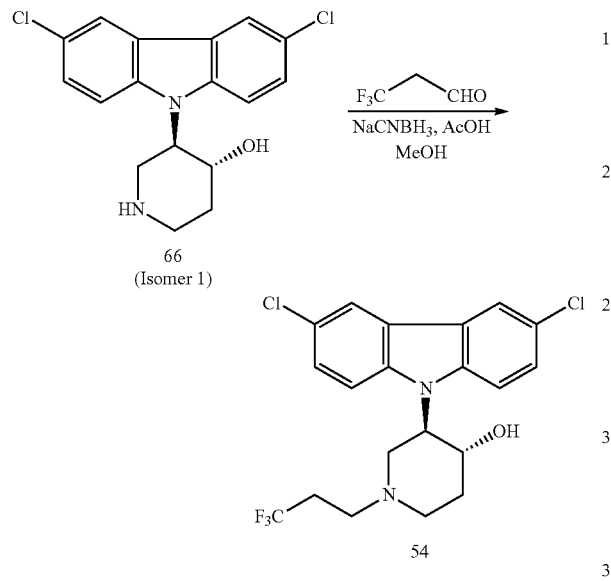

COMPOUND NO. 66: (3R,4R)-3-(3,6-dichloro-9H-carbazol-9-yl)piperidin-4-ol
COMPOUND NO. 54: (3R,4R)-3-(3,6-dichloro-9H-carbazol-9-yl)-1-(3,3,3-trifluoropropyl)piperidin-4-ol
Please refer protocol for compound No. 46 for all reductive amination procedures.
Compound No. 54: 0.04 g, 62.1%
LCMS: (Method B) 432 (M+H), RT. 2.89 min, 99.68% (max)
HPLC: (Method A) RT 12.33 min, 99.61% (max)
¹HNMR (400 MHz, DMSO-d6): δ 8.33 (s, 2H), 7.86 (m, 1H), 7.61-7.62 (m, 1H), 7.43 (br s, 2H), 4.86 (d, J=5.7 Hz), 4.41-4.44 (m, 1H), 4.31-4.35 (m, 1H), 2.89-2.97 (m, 3H), 2.59-2.66 (m, 2H), 2.31-2.38 (m, 2H), 1.91-2.16 (m, 1H), 1.64-1.68 (m, 1H).

Synthesis of 3,6-bis(trifluoromethyl)-9H-carbazole Int B3

U.S. Pat Appl. Publ., 20130040977, 14 Feb. 2013

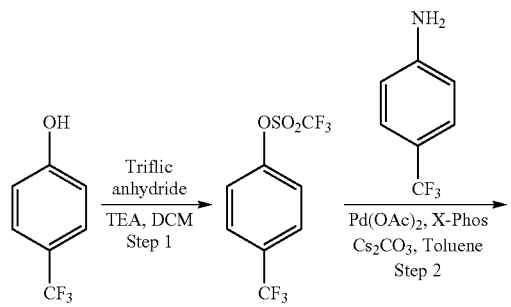

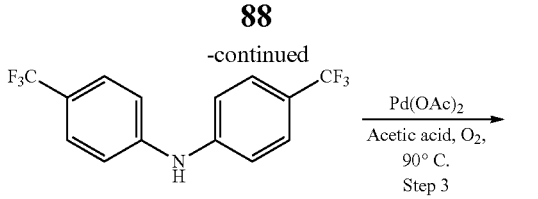

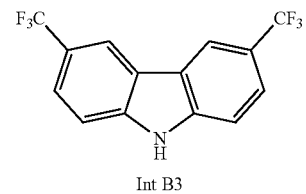

Int B3

Step 1: To a solution of 4-trifluoromethylphenol (25.0 g, 154 mmol) in dichloromethane (100 mL) was added pyridine (14.6 mL, 185 mmol) and stirred. To this stirred solution was added solution of triflic anhydride (27.9 mL, 169 mmol) in dichloromethane (100 mL) at 0° C. The mixture was stirred at 0° C. for 1 h, and then room temperature for 2.5 h. The reaction was quenched with 25 mL of water and the organic phase saturated with NaHCO₃, 1M HCl and brine, then dried with MgSO₄ and concentrated to give crude product. The crude product was further purified by silica gel chromatography using 5% ethyl acetate/petroleum ether to afford 27.4 g of colorless oil as product (Yield 60.4%).

¹H NMR (400 MHz, CDCl₃): δ 7.74-7.76 (m 2H), 7.27-7.29 (m, 2H).

Step 2: The product of step 1 (5.0 g, 16.9 mmol), 4-(trifluoromethyl)aniline (3.01 g, 18.6 mmol), Pd(OAc)₂ (0.38 g, 1.69 mmol), XPhos (1.2 g, 2.5 mmol) and Cs₂CO₃ (6.6 g, 20.2 mmol), was added toluene (100 mL) and stirred at 100° C. for 3 h in a sealed tube under nitrogen. After cooling, the crude mixture was diluted with ethyl acetate and washed with brine. The organic layer was dried with MgSO₄ and concentrated. The crude product was further purified by silica gel chromatography using 0-5% of EtOAc/Hex to afford 5.0 g of the diaryl amine as a colorless oil (Yield: 96%).

LCMS: (Method B) 304 (M+H), RT. 3.59 min, 99.266% (215)

1H NMR (400 MHz, CDCl₃): δ9.10 (s, 1H), 7.58-7.59 (m, 4H), 7.25-7.27 (m, 4H).

Step 3: To bis(4-(trifluoromethyl)phenyl)amine (5.4 g, 17.6 mmol), was added acetic acid (54 mL) and Pd(OAc)₂ (0.397 g, 1.76 mmol) and heated to 90° C. for 12 h under an oxygen balloon. Solid NaHCO₃ was added to quench the reaction and the mixture was diluted with ethyl acetate. The organic layer was dried with MgSO₄ and concentrated to give crude product. It was further purified by silica gel chromatography using 25% ethyl acetate/petroleum ether to afford 2.8 g of white solid (Yield: 56%).

LCMS: (Method B) 303 (M+H), RT. 2.83 min, 99.88% (max)

¹H NMR (400 MHz, CDCl₃): δ 12.12 (s, 1H), 8.81 (s, 2H), 7.75-7.77 (m, 2H), 7.73 (d, J=8.00 Hz, 2H).

Synthesis of Compound No. 68, Compound No. 59, Compound No. 60 & Compound No. 61
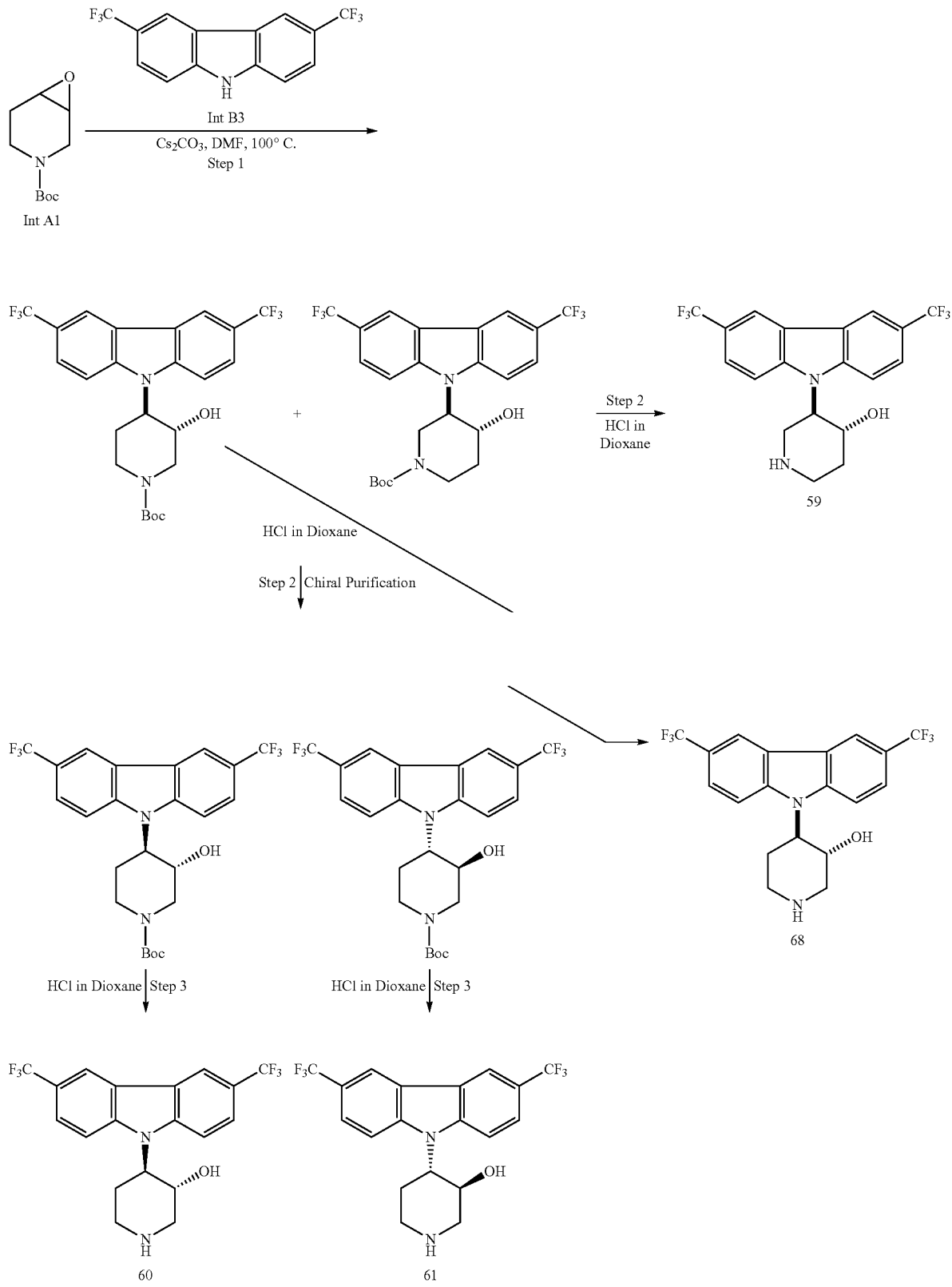

COMPOUND NO. 59: trans-3-(3,6-bis(trifluoromethyl)-9H-carbazol-9-yl)piperidin-4-ol COMPOUND NO. 68: trans-4-(3,6-bis(trifluoromethyl)-9H-carbazol-9-yl)piperidin-3-ol COMPOUND NO. 60: (3R,4R)-4-(3,6-bis(trifluoromethyl)-9H-carbazol-9-yl)piperidin-3-ol COMPOUND NO. 61: (3S,4S)-4-(3,6-bis(trifluoromethyl)-9H-carbazol-9-yl)piperidin-3-ol Step 1: To a stirred solution of Int B3 (1.82 g, 6.0 mmol) in dry N, N-dimethyl formamide (20 mL) was added cesium carbonate (2.93 g, 9.0 mmol) under $N_2$ atmosphere and the reaction mixture stirred at 80° C. for 1 h. After 1 h, Int A1 (1.07 g, 5.4 mmol) was added to the reaction mixture and stirred at 80° C. for 18 h. After completion of the reaction, the reaction mixture was diluted with ethyl acetate (100 mL), washed with water, brine solution and dried over anhydrous $Na_2SO_4$. The regioisomers were purified by the flash column chromatography (230-400 size mesh) as elution 1 (non polar) was the regioisomer 1 (0.6 g, 19.9%) and elution 2 was the regio-isomer 2 (0.5 g, 16.6%) as white solid.

Step 2:

To a stirred solution of regio-isomer-2 (0.1 g) in dioxane, HCl in dioxane was added after cooling to 0° C. and stirred at room temperature overnight. After completion, the reaction mixture was concentrated and given diethylether wash to get compound No. 59 (0.085 g, 97%).

LCMS: (Method B) 403 (M+H), RT. 2.6 min, 96.41% (max)

HPLC: (Method A) RT 11.49 min, 96.87% (210-400 nm)

$^1$HNMR (400 MHz, DMSO-d6): δ 9.40 (br s, 1H), 9.33 (br s, 1H), 8.90-8.92 (m, 2H), 8.28-8.30 (m, 1H), 7.91-7.93 (m, 1H), 7.78-7.84 (m, 2H), 5.33 (s, 1H), 5.05-5.11 (m, 1H), 4.65 (s, 1H), 3.81-3.84 (m, 1H), 3.39-3.61 (m, 3H), 2.19-2.22 (m, 1H), 1.93-1.98 (m, 1H).

Same protocol was followed for all compounds which involved de-protection of the boc group.

Compound No. 68:

LCMS: (Method B) 403 (M+H), RT. 2.72 min, 97.66% (max)

HPLC: (Method A) RT 11.91 min, 96.74% (210-400 nm)

$^1$HNMR (400 MHz, DMSO-d6): δ 9.62 (s, 1H), 9.14 (d, J=8.00 Hz, 1H), 8.92 (s, 1H), 8.88 (s, 1H), 8.60-8.61 (m, 1H), 7.97 (d, J=8.00 Hz, 1H), 7.81-7.82 (m, 2H), 5.57 (s, 1H), 4.97-4.98 (m, 1H), 4.81 (s, 1H), 3.57-3.58 (m, 2H), 3.13-3.14 (m, 2H), 2.81-2.84 (m, 2H), 2.07-2.10 (m, 1H).

Compound No. 60 & Compound No. 61:

The regioisomer-1 (0.6 g) was submitted for chiral preparative purification using Method B and obtained 0.26 g of isomer 1 and 0.25 g of isomer 2. After de-protection of the respective individual isomers, compound No. 60 and compound No. 61 were obtained.

Compound No. 60: 0.21 g, 95%

LCMS: (Method B) 403 (M+H), RT. 2.74 min, 99.65% (max)

HPLC: (Method B) RT 12.21 min, 98.91% (max)

$^1$HNMR (400 MHz, DMSO-d6): δ 9.60 (br s, 1H), 9.13 (br s, 1H), 8.88-8.92 (m, 2H), 8.29-8.31 (m, 1H), 7.94-7.98 (m, 1H), 7.83-7.88 (m, 2H), 5.58 (d, 1H, J=5.5 Hz), 4.97-5.04 (m, 1H), 4.78-4.85 (m, 1H), 3.48-3.51 (m, 2H), 3.22-3.25 (m, 1H), 2.89-2.95 (m, 2H), 2.06-2.10 (m, 1H)

Compound No. 61: 0.21 g, 96.3%

LCMS: (Method B) 403 (M+H), RT. 2.72 min, 99.77% (max)

HPLC: (Method B) RT 12.22 min, 99.85% (max)

$^1$HNMR (400 MHz, DMSO-d6): δ $^1$HNMR (400 MHz, DMSO-d$_6$) δ 9.27 (br s, 2H), 8.88-8.92 (m, 2H), 8.26-8.27 (m, 1H), 7.96 (br s, 1H) 7.85-7.88 (m, 2H), 5.57 (d, J=4.89 Hz, 1H), 5.02-5.03 (m, 1H), 4.96-4.99 (m, 1H), 3.48-3.52 (m, 2H), 3.19-3.25 (m, 1H), 2.92 (t, J=10.76 Hz, 2H), 2.08 (d, J=10.76 Hz, 1H).

Synthesis of 3,6-dichloro-9H-pyrido[2,3-b]indole Int B4

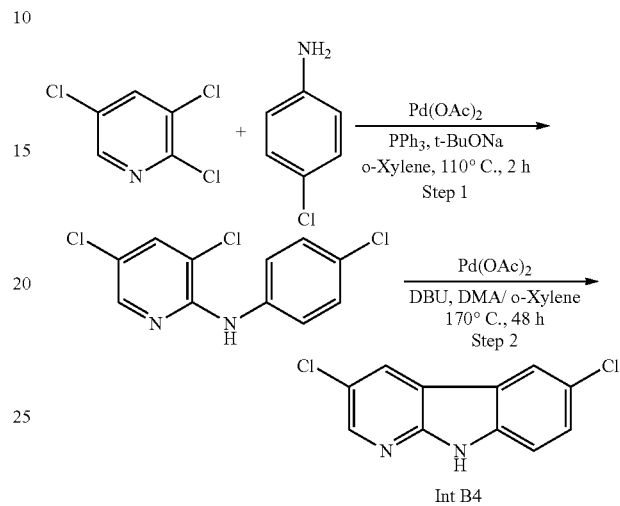

Int B4

Step 1:

In a sealed tube, 2,3,5-trichloro pyridine (8.0 g, 44 mmol), 4-chloro aniline (6.17 g, 49 mmol), triphenyl phosphine (1.16 g, 44 mmol) and sodium-tert-butoxide (5.09 g, 53 mmol) were mixed in o-xylene (80 mL). The resulting mixture was purged with argon, added Pd(OAc)$_2$ (0.49 g, 2.2 mmol) and heated at 110° C. for 12 h. After completion of the reaction, the reaction mixture was filtered through Celite® bed and concentrated under vacuum. The residue obtained was diluted with ethyl acetate (200 mL), washed with water, brine solution and dried over anhydrous $Na_2SO_4$. The organic phase was concentrated and purified by the column chromatography (60-120 size mesh) to get the yellow solid 3,5-dichloro-N-(4-chlorophenyl)pyridin-2-amine (7.0 g, 58.23%).

LCMS: (Method B) 275 (M+H), RT. 3.69 min, 81.18% (max)

$^1$H NMR (400 MHz, DMSO-d6): δ 8.68 (s, 1H), 8.14 (d, J=2.28 Hz, 1H), 8.04 (d, J=2.32 Hz, 1H), 7.68-7.66 (m, 2H), 7.34-7.32 (m, 2H).

Step 2:

In a sealed tube, 3,5-dichloro-N-(4-chlorophenyl)pyridin-2-amine (4.0 g, 14.7 mmol), DBU (4.4 g, 29.5 mmol) and tricyclohexyl phosphine tetrafluoro borate (0.54 g, 1.47 mmol) were mixed in DMA/o-xylene (1:2) (50 mL) The resulting mixture was purged with argon, added Pd(OAc)$_2$ (0.16 g, 0.73 mmol) and heated at 170° C. for 48 h. After completion of the reaction, the solvent was concentrated under vacuum. The residue obtained was diluted with ethyl acetate (150 mL), washed with water, brine solution and dried over anhydrous $Na_2SO_4$. The organic phase was concentrated and purified by column chromatography (60-120 size mesh) to afford 3,6-dichloro-9H-pyrido[2,3-b]indole Int B4 (1.2 g, 34.6%) as yellow solid.

LCMS: (Method B) 235 (M+H), RT. 3.34 min, 99.57% (max)(negative mode)

$^1$H NMR (400 MHz, DMSO-d6):δ 12.17 (s, 1H), 8.74 (s, 1H), 8.46 (s, 1H), 8.33 (s, 1H), 7.52-7.51 (m, 2H).

Synthesis of Compound No. 19, Compound No. 20, Compound No. 55 & Compound No. 56 reaction, reaction mixture was diluted with ethyl acetate (100 mL), washed with water, brine solution and dried over anhydrous $Na_2SO_4$. Organic phase was concentrated and purified by column chromatography to get both regioisomer

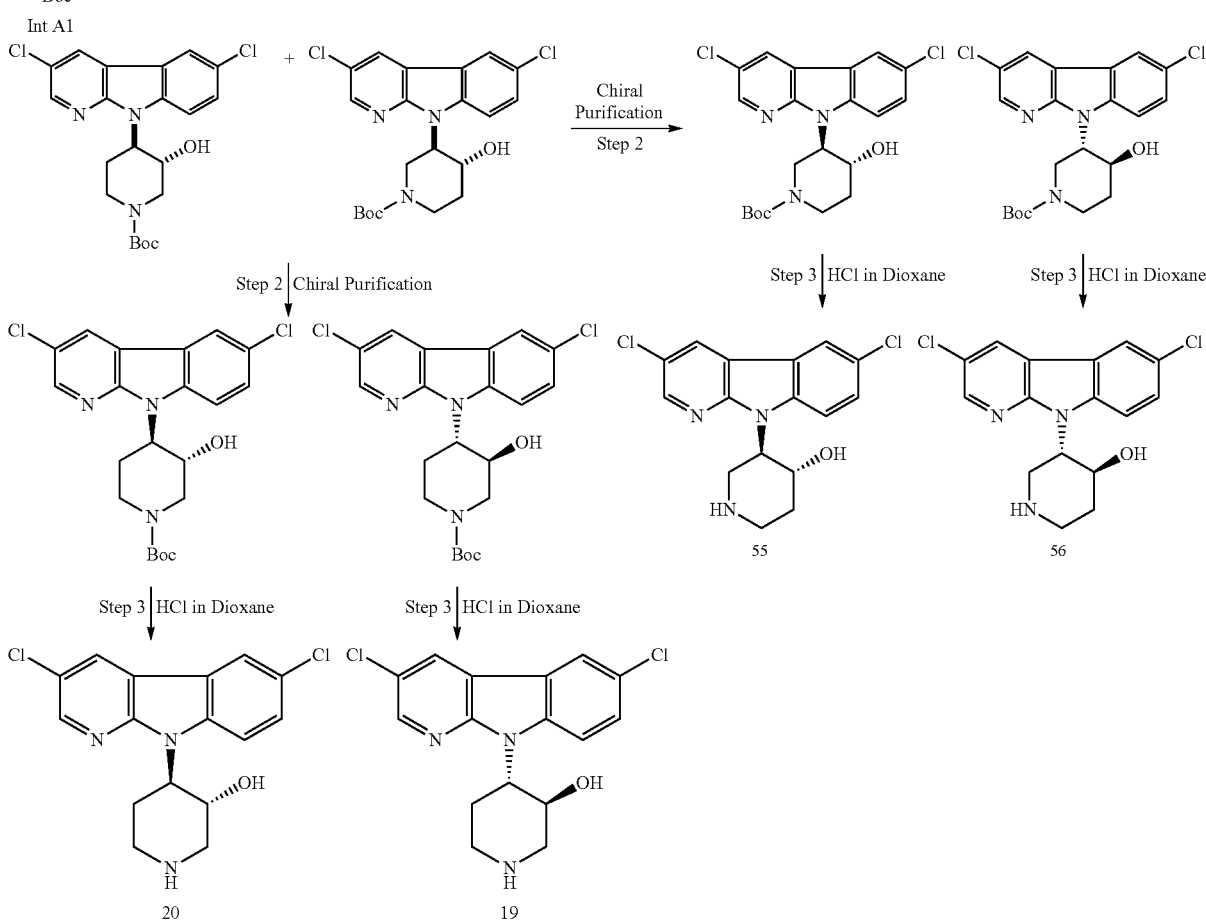

COMPOUND NO. 55: (3R,4R)-3-(3,6-dichloro-9H-pyrido[2,3-b]indol-9-yl)piperidin-4-ol
COMPOUND NO. 56: (3S,4S)-3-(3,6-dichloro-9H-pyrido[2,3-b]indol-9-yl)piperidin-4-ol
COMPOUND NO. 20: (3R,4R)-4-(3,6-dichloro-9H-pyrido[2,3-b]-indol-9-yl)piperidin-3-ol
COMPOUND NO. 19: (3S,4S)-4-(3,6-dichloro-9H-pyrido[2,3-b]indol-9-yl)piperidin-3-ol Step 1: To a solution of 3,6-dichloro-9H-pyrido[2,3-b]indole Int B4 (3.0 g, 12.6 mmol) in dry N,N-dimethyl formamide (20 mL), was added cesium carbonate (6.18 g, 18.9 mmol) under $N_2$ atmosphere and the reaction mixture stirred at 100° C. for 1 h. After 1 h, Int A1 (2.52 g, 12.6 mmol) was added to the reaction mixture and stirred at 100° C. for 18 h. After completion of together, which was then separated by reverse phase preparative chromatography to get the product as yellow solid.

Yield: Regio-isomer 1 (Elution 1) 0.6 g, 11%
Yield: Regio-isomer 2 (Elution 2) 0.80 g, 14.5%
Compound No. 20 & Compound No. 19:
The regio-isomer-1 (0.6 g) was submitted for chiral preparative purification using MethodE and obtained 0.15 g of isomer 1 and 0.15 g of isomer 2. After deprotection of the respective individual isomers, compound No. 78 and compound No. 79 were obtained.
Compound No. 20 (Isomer 1):0.125 g, 92%
LCMS: (Method B) 337 (M+H), RT. 2.44 min, 97.72% (max)
HPLC: (Method A) RT 10.78 min, 98.42% (max)

¹HNMR (400 MHz, DMSO-d6): δ 9.44 (s, 1H), 9.20 (s, 1H), 8.67 (s, 1H), 8.43 (s, 1H), 7.60-7.63 (m, 1H), 4.86 (s, 1H), 3.48-3.57 (m, 2H), 3.10-3.12 (m, 1H), 2.90-2.92 (m, 2H), 2.01-2.03 (m, 1H), 1.26-1.27 (m, 2H).
Compound No. 19 (ISOMER 2): 0.125 g, 92%
LCMS: (Method B) 337 (M+H), RT. 2.46 min, 98.22% (max)
HPLC: (Method A) RT 10.79 min, 97.44% (max)
¹HNMR (400 MHz, DMSO-d6): δ 9.45 (s, 1H), 8.83 (d, J=2.40 Hz, 2H), 8.51 (d, J=2.00 Hz, 1H), 8.42 (s, 1H), 7.59 (d, J=4.80 Hz, 1H), 4.86 (s, 1H), 3.51-3.57 (m, 2H), 3.39-3.41 (m, 2H), 3.15-3.17 (m, 2H), 3.08-3.10 (m, 2H), 2.86-2.88 (m, 2H), 2.02 (s, 1H), 1.26-1.28 (m, 2H).
Compound No. 55 & Compound No. 56:
The regio-isomer-2 (0.6 g) was submitted for chiral preparative purification using Method E and obtained 0.25 g of isomer 1 and 0.26 g of isomer 2. After deprotection of the respective individual isomers, compound No. 55 and compound No. 56 were obtained.
Compound No. 55 (Isomer 1):0.21 g, 90%
LCMS: (Method B) 337 (M+H), RT. 2.39 min, 98.52% (max)
HPLC: (Method A) RT 10.45 min, 99.65% (max)
¹HNMR (400 MHz, DMSO-d6): δ 9.46 (br s, 2H), 8.83 (s, 1H), 8.68 (s, 1H), 8.52 (s, 1H), 8.41 (s, 1H), 7.60-7.62 (m, 1H), 3.91-4.01 (m, 1H), 3.38-3.58 (m, 3H), 3.09-3.14 (m, 1H), 2.84-2.91 (m, 2H), 2.14-2.17 (m, 2H), 1.87-1.90 (m, 1H).
Compound No. 56 (Isomer 2):0.21 g, 90%
LCMS: (Method B) 337 (M+H), RT. 2.39 min, 99.54% (max)
HPLC: (Method A) RT 10.45 min, 99.09% (max)
¹HNMR (400 MHz, DMSO-d6): δ 9.57 (s, 2H), 8.84 (d, J=2.24 Hz, 1H), 8.52 (d, J=2 Hz, 1H), 8.42 (s, 1H), 7.80 (br s, 1H), 7.61-7.63 (m, 1H), 5.10 (br s, 1H), 4.53-4.68 (m, 4H), 4.02 (br s, 1H), 3.56-3.61 (m, 1H), 2.09-2.24 (m, 2H), 2.14-2.17 (m, 1H), 1.90-1.93 (m, 1H).
Compound No. 57 & Compound No. 58:

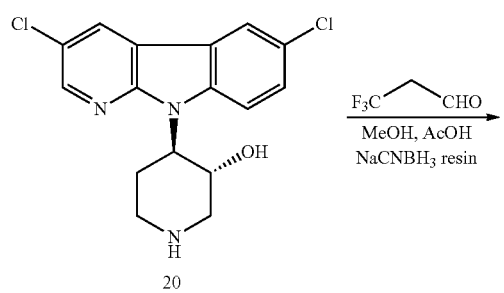

20

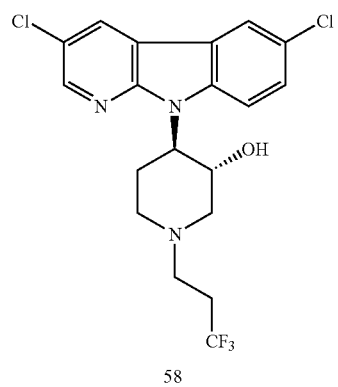

58

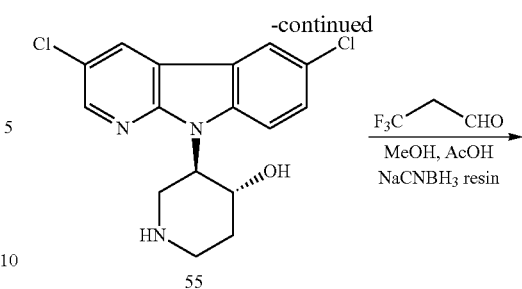

55

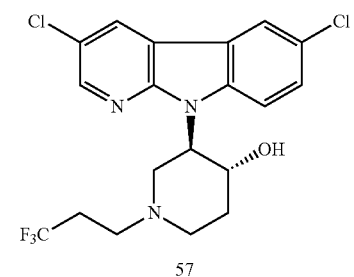

57

COMPOUND NO. 20: (3R,4R)-4-(3,6-dichloro-9H-pyrido[2,3-b]indol-9-yl)piperidin-3-ol
COMPOUND NO. 58: (3R,4R)-4-(3,6-dichloro-9H-pyrido[2,3-b]indol-9-yl)-1-(3,3,3-trifluoropropyl)piperidin-3-ol
COMPOUND NO. 55: (3R,4R)-3-(3,6-dichloro-9H-pyrido[2,3-b]indol-9-yl)piperidin-4-ol
COMPOUND NO. 57: (3R,4R)-3-(3,6-dichloro-9H-pyrido[2,3-b]-indol-9-yl)-1-(3,3,3-trifluoropropyl)piperidin-4-ol
Please refer protocol for compound No. 46 for all reductive amination procedures.
Compound No. 58:0.03 g, 37.6%
LCMS: (Method B) 433 (M+H), RT. 2.74 min, 99.67% (max)
HPLC: (Method B) RT 11.70 min, 99.02% (max)
¹HNMR (400 MHz, DMSO-d6): δ 8.80 (d, J=2.4 Hz, 1H), 8.52 (d, J=2.4 Hz, 1H), 8.39 (s, 1H), 7.76 (d, J=8.8 Hz, 1H), 7.56 (dd, J=2.2 Hz, 8.8 Hz, 1H), 4.89 (s, 1H), 4.69 (br s, 1H), 4.37 (m, 1H), 3.11-3.14 (m, 1H), 2.99-3.01 (m, 2H), 2.51-2.67 (m, 4H), 2.17-2.27 (m, 1H), 1.93-2.07 (m, 1H), 1.75-1.81 (m, 1H).
Compound No. 57:0.02 g, 26%
LCMS: (Method B) 433 (M+H), RT. 2.73 min, 95.48% (max)
HPLC: (Method B) RT 14.06 min, 98.94% (max)
¹HNMR (400 MHz, DMSO-d6): δ 8.79 (d, J=2.4 Hz, 1H), 8.52 (d, J=2.4 Hz, 1H), 8.40 (m, 1H), 7.68-7.80 (m, 1H), 7.54 (dd, J=1.8 Hz, 8.8 Hz, 1H), 4.81-4.82 (m, 1H), 4.6 (br s, 1H), 2.95-2.98 (m, 2H), 2.57-2.67 (m, 3H), 2.46-2.50 (m, 1H), 1.61-1.68 (m, 1H), 1.99-2.01 (m, 1H), 1.62-1.68 (m, 1H).
Biological Test 1: In Vitro Sensitivity Assays: *Plasmodium falciparum* by ³H-Hypoxanthine Incorporation.
The strain used for this assay is the Chloroquine/Pyrimethamine resistant *Plasmodium falciparum* K1 and drugs such as Chloroquine (10 mg/mL stock; start concentration 1000 ng/mL) and Artemisinine (Qinghaosu) (5 mg/mL stock; start concentration 10 ng/mL) were used as standards.
Human red blood cells were used as host cells and the activity was measured using a ³H-hypoxanthine incorporation assay.

Into a Costar™ 96-well microtitre plates, 100 µL of medium (RPMI 1640 without hypoxanthine 10.44 g/L, HEPES 5.94 g/L, Albumax® 5 g/L, Neomycin 10 mL/L, NaHCO$_3$ 2.1 g/L) were added to the wells of row containing drugs available from stock solutions of 10 mg/mL in DMSO (compounds were kept at −20° C. Since DMSO is toxic, care had to be taken not to exceed a final concentration of 0.5% DMSO). Then 100 µL of medium were added at rt to all wells of the plate. By means of a 12-well multi-pipette serial drug dilutions were prepared. A serial dilution factor of 1:2 is thus obtained. One row of wells without drugs served as controls. Next 100 µL of medium+washed human red blood cells A+(RBC) was added to the last 4 wells of the first row; these columns serve as background controls (that may be caused by 3H-hypoxanthine incorporation into RBC without the parasite). Into the remaining wells, 100 µL of medium+RBC+P. falciparum mix was added. The plates were placed for 48 h into a chamber at 37° C. gassed with a 4% CO$_2$, 3% O$_2$, 93% N$_2$ mix. Finally 50 µL of medium+3H-hypoxanthine [(500 µL $^3$H-hypoxanthine stock+500 µL EtOH+49 mL medium (0.5 µCi)] was added to each well and the plates were put back at 37° C. for 24 h into the chamber and gassed with a 4% CO$_2$, 3% O$_2$, 93% N$_2$ mix. The plates were then read using the Cell Harvester and the data were transferred into a graphic program (Excel) and are evaluated to determine the IC$_{50}$ by linear interpolation.

Biological Test 2: *Plasmodium berghei* Acute In Vivo Model.

For this study *Plasmodium berghei*, (GFP ANKA strain) was used as parasite strain and drugs such as Chloroquine (Sigma C6628) Artemisinin (Sigma 36, 159-3) were used as positive controls.

For the assay a donor mouse with approximately 30% parasitaemia, heparinised blood (containing 50 µL of 200 µ/mL Heparin) was taken and diluted in physiological saline to $10^8$ parasitized erythrocytes per mL. An aliquot (0.2 mL) of this suspension was injected intravenously (i.v.) into experimental groups of 3 mice (NMRI mice, females, 20-22 g), and a control group of 3 mice. The mice were studied in a standard macrolon cages type II at 22° C. and 60-70% relative humidity, and were fed with special pellets (PAB45—NAFAG 9009, Provimi Kliba A G, CH-4303 Kaiseraugst, Switzerland), water ad libitum. 4 hours post-infection—the experimental groups were treated with a single dose i.p of the tested drug. The dosage was 50 mg/kg/day and the drug concentration (DMSO 10%) was adjusted so that 0.1 mL/10 g was injected. In a similar manner after 24, 48 and 72 hours post-infection—the experimental groups were treated with a single daily dose i.p. Finally 24 hours after the last drug treatment, 1 µL tail blood was taken and dissolved in 1 mL PBS buffer. Parasitaemia was determined with a FACScan (Becton Dickinson) by counting 100'000 red blood cells. The difference between the mean value of the control group and those of the experimental groups was then calculated and expressed as a percent relative to the control group (=activity). The survival of the animals was monitored up to 30 days and mice surviving for 30 days were checked for parasitaemia and subsequently euthanised. A compound is considered curative if the animal survives to day 30 post-infection with no detectable parasites. The result is expressed as 1) reduction of parasitaemia on day 4 in % as compared to the untreated control group, and 2) mean survival of the group.

B. Franke-Fayard et al., Mol. Biochem. Parasitol., 137 (1),23-33, 2004

Compounds of formula (I) were tested in the above in vivo mouse model and showed a decrease of parasitemia above 99.9% with 30 mean survival days of the mice. Typically examples 6 and 7 have been tested in the in vivo mouse model, and show a decrease of parasitemia of respectively 99.8% (with Mean Survival Days=30), 100% (Mean Survival Days=30).

In vitro activities against K1 strain of *Plasmodium Falciparum* are given in the table below:

TABLE 1 list of in vitro activities against *P. falciparum* K1 strain

| Compound No. | IC$_{50}$ K1 in vitro (nM) |
|---|---|
| 1 | 315 |
| 2 | 127 |
| 3 | 3 |
| 4 | 3 |
| 5 | 9 |
| 6 | 10 |
| 7 | 9 |
| 8 | 781 |
| 9 | 16 |
| 10 | 33 |
| 11 | 1147 |
| 12 | 3671 |
| 13 | 886 |
| 14 | 13 |
| 15 | 383 |
| 16 | 364 |

Cultivation of *P. falciparum*:

*P. falciparum* strain NF54 was obtained from the Research and Reference Reagent Resource Center (MR4) (Manassas, Va.). The two strains were maintained in vitro by a modification of the method of Trager and Jensen. Cultures were maintained in A positive (A+) human erythrocytes suspended at 5% hematocrit in complete medium. 5 g albumax II (Gibco-Invitrogen, Cat No#11021037), 2.5 mg gentamicin (Sigma Aldrich), 25 mM HEPES (Invitrogen), 5 mg hypoxanthine (Sigma), and 1 L of RPMI 1640 (Invitrogen, Cat No#11875085). Cultures were grown in 100 mm petri-dishes (BD Falcon) at a volume of 15 mL and were kept in a standard gas environment of 4% CO2 and 3% 02 at temperature 37° C. in a tri-gas incubator (Cat#3131, Thermo Scientific Forma Series II Water Jacketed). Parasite growth and morphology were observed daily using thin smears at 100× (oil immersion) magnification following staining with Geimsa stain.

*P. falciparum* growth assay:

The protocol assesses the compound efficacy against the growth of *P. falciparum* in-vitro.

Parasite growth was detected in assay by the traditional [3H] hypoxanthine incorporation assay as previously described by Desjardins and colleagues (Antimicrob. Agents Chemother., 16(6), 710, 1979). To perform the [3H] hypoxanthine incorporation assay, the new antimalarial agents were serially diluted 1:1 into hypoxanthine-free complete medium to a final volume of 100 µL (final antimalarial agent concentration range, 10,000 nM to 4.8 nM may change in special case) in 96 well sterile cell culture plates. 100 µL of *P. falciparum* culture (0.3% p and 1.25% h-synchronized ring stage) is added per well, by addition, anti-malarial agents are diluted in such a way that the final DMSO concentration in the well does not exceed 0.1%. All cultures used in the study are albumax II adopted. The microtiter plates were incubated in chamber in a standard gas environment at 37° C. for 72 h. After 48 h of incubation and prior to addition of 50 μL (0.5 μCi/well) 3H-Hypoxanthine (specific activity, 20 Ci/mmol, Conc. 1.0 mCi/ml; American Radiolabeled Chemicals, Inc., St. Louis, Mo.), culture growth was assessed by making the smears that ensures the culture has grown in % p and assay plate is further incubated for 24 h. Following the incubation period, the plates were harvested with a FilterMate cell harvester (Perkin Elmer) onto unifilter-96 GF/B plates, washed with distilled water to remove excess radiochemical and plates were kept for drying 37° C. overnight or 60° C. for 1 h. 50 μL of Microscint scintillation cocktail (Microscint-High Efficiency LSC-Cocktail; Perkin Elmer) added in the unifilter-96 GF/B plates and kept for 15-20 min. The plates were counted in a Top Count NXT microplate scintillation and luminescence counter (Perkin Elmer). The mean values for [3H]hypoxanthine incorporation in parasitized control and non-parasitized control erythrocytes were calculated.

Assay data were analyzed using Graph pad prism ver.5 software. A variable sigmoid dose response curve is plotted keeping log concentrations at X-axis and % inhibition at Y-axis.

TABLE 2 list of in vitro activites against *P. falciparum* NF54 strain

| Compound No. | $IC_{50}$ NF54 (nM) |
| --- | --- |
| 5 | 108.6 |
| 6 | 40.16 |
| 7 | 41.17 |
| 9 | 307 |
| 19 | 93.35 |
| 20 | 123.8 |
| 41 | 279.8 |
| 42 | 79.84 |
| 43 | 910.3 |
| 44 | 792 |
| 45 | 96 |
| 46 | 1330 |
| 47 | 576 |
| 48 | 1255 |
| 49 | 33.59 |
| 50 | 290.1 |
| 51 | 555 |
| 52 | 168.9 |
| 53 | 73.63 |
| 54 | 28.16 |
| 55 | 3595 |
| 56 | 3406 |
| 57 | 2235 |
| 58 | 724.1 |
| 59 | 1304 |
| 60 | 20.47 |
| 61 | 20.52 |
| 62 | 263 |
| 63 | 232.9 |
| 66 | 1690 |
| 68 | 22.21 |

Biological Experiment 5: In Vivo Efficacy Against *P falciparum* PF3D/$^{0087/N9}$ for the compound No. 6 Described in Example 6

In vivo activity in a murine model of *falciparum*-Malaria
Angulo-Barturen I, Jimenez-Diaz M B, Mulet T, Rullas J, Herreros E, et al. (2008) A Murine Model of *falciparum*-Malaria by In Vivo Selection of Competent Strains in Non-Myelodepleted Mice Engrafted with Human Erythrocytes. PLoS ONE 3(5): e2252. doi: 10.1371/journal.pone.0002252.

This study measures the therapeutic efficacy of compound no. 6 against *Plasmodium falciparum* growing in peripheral blood of NODscidIL2Rynull mice engrafted with human erythrocytes. The antimalarial efficacy of compound no. 6 is assessed using a "4-day test".

The parameters of efficacy estimated in the study are a) the dose of compound no. 6 in mg·kg-1 that reduces parasitemia at day 7 after infection by 90% with respect to vehicle-treated mice (parameter denoted as ED90) and b) the estimated average daily exposure in whole blood of compound no. 6 necessary to reduce *P. falciparum* parasitemia in peripheral blood at day 7 after infection by 90% with respect to vehicle-treated mice (parameter used to measure the potency of the compound and denoted as $AUC_{ED90}$).

| Compound No. | $ED_{90}$ (mg · $kg^{-1}$) | $AUC_{ED90}$ (μg · h · $ml^{-1}$ · $day^{-1}$) |
| --- | --- | --- |
| 6 | 22.5 | 28.5 |

If a compound of the formula (I) contains more than one group which is capable of forming pharmaceutically acceptable salts of this type, the formula I also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula (I) can be chiral and can accordingly occur in various enantiomeric forms. They can therefore exist in racemic or in optically active form. The formula (I) also encompasses the diastereoisomers and mixtures of diastereoisomers, in all ratios, of these compounds.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the (R) and (S) forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units, which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be for-mulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I) and salts, solvates and physiologically functional derivatives thereof and the other active ingredients can also be administered in the form of liposome delivery systems, such as, for exam-pie, small unilamellar vesicles, large unilamellar vesicles and multilamellar vesicles. Liposomes can be formed from various phospholipids, such as, for example, cholesterol, stearylamine or phosphatidylcholines.

The compounds of the formula (I) and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se. The present invention furthermore relates to a method for treating a subject suffering from a parasitic disease, comprising administering to said subject an effective amount of a compounds of formula (I) and related Formulae. The present invention preferably relates to a method, wherein the parasitic disease is malaria or HAT.

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:
1. A compound of formula I:

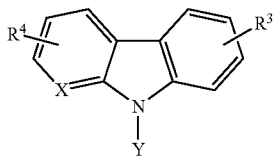

(I)

wherein
Y is a group selected from

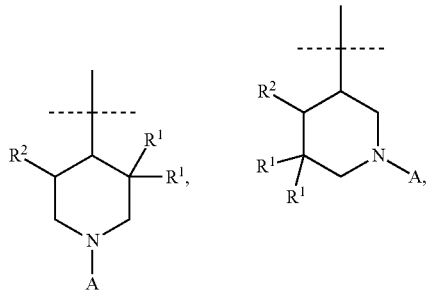

$R^1$ denotes H or F,
$R^2$ denotes OH,
X denotes CH or N,
$R^3$ and $R^4$ independently of one another denote H, Hal or OA, CHal$_3$
Hal is F, Cl, Br or I,
A denotes H or Alk,
Alk is a branched or linear alkyl group having 1 to 8 carbon atoms or cycloalkyl having 3 to 6 carbon atoms, wherein 1 to 7 H-atoms may be independently replaced by Hal, OR, COOR, CN, NR$_2$, phenyl, linear or branched alkyl having 1, 2 or 3 C atoms, cycloalkyl having 3 to 6 carbon atoms and/or wherein 1 to 3 CH$_2$-groups may be replaced by O, —NRCO—, —CO—, —COO—, —CONR, —NR—or S, or cycloalkyl having 3 to 6 carbon atoms,
R is H or is a branched or linear alkyl group having 1 to 8 carbon atoms and pharmaceutically acceptable salts, esters and N-oxides thereof.

2. The compound according to claim 1, having formula IA or its enantiomer:

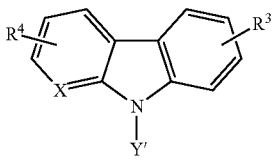

(IA)

wherein
Y' is a group selected from

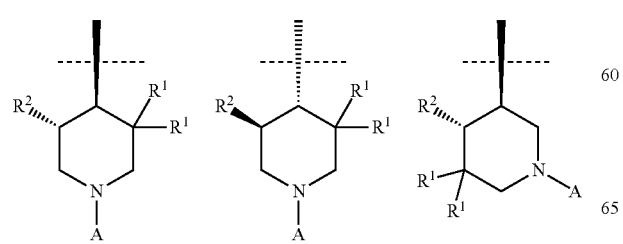

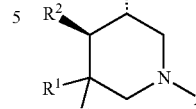 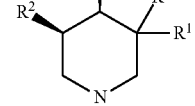

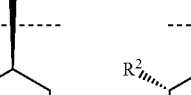

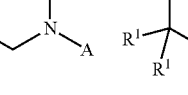

$R^2$ is OH,
$R^1 R^3$, $R^4$, X and A are as defined in claim 1, and pharmaceutically acceptable salts, esters and N-oxides thereof.

3. The compound of claim 1, wherein $R^1$ is H.

4. The compound of claim 1, wherein $R^3$ and $R^4$ are both Cl, F, CF$_3$ or CCl$_3$.

5. The compound of claim 1, wherein $R^3$ is Cl and $R^4$ is F or wherein $R^3$ is F and $R^4$ is Cl.

6. The compound of claim 1, wherein A is a linear or branched alkyl group wherein 1, 2, 3, 4 or 5 H atoms are independently replaced by Hal, methyl and/or wherein one CH$_2$-group is replaced by cyclopropyl.

7. A pharmaceutical composition comprising the compound of claim 1.

8. A method of treating malaria by administering an effective amount of a compound of claim 1.

9. A pharmaceutical composition comprising at least one compound of claim 1 and/or pharmaceutically usable tautomers, salts, solvates and stereoisomers thereof, including mixtures thereof in all ratios, and pharmaceutically acceptable excipients and/or adjuvants.

10. A pharmaceutical composition comprising at least one compound of claim 1 and/or pharmaceutically acceptable tautomers, salts, solvates and stereoisomers thereof, including mixtures thereof in all ratios, and at least one further active ingredient.

11. A kit consisting of separate packs of:
(a) an effective amount of a compound of claim 1, and
(b) an effective amount of a further medicament active ingredient.

12. A process for preparing a compound of claim 1, comprising:
reacting a compound of formula (IV) wherein $R^3$ and $R^4$ are as defined in claim 1,

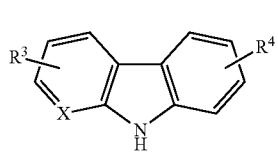

(IV)

with a compound of formula (III), (III') or (III")

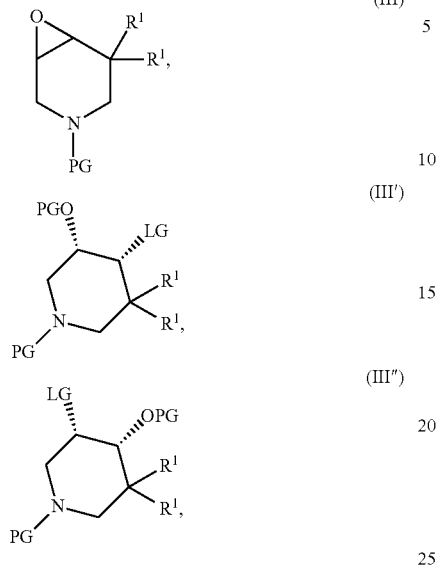

wherein R¹ is as defined in claim 1, LG denotes a leaving group and PG denotes a protecting group; and
removing the groups PG.

13. The compound of claim 1, wherein the compound is a racemic mixture, a substantially pure enantiomer, a mixture of enantiomers, or a mixture of diastereoisomers.

14. The compound of claim 1, wherein the compound is selected from the following group of:

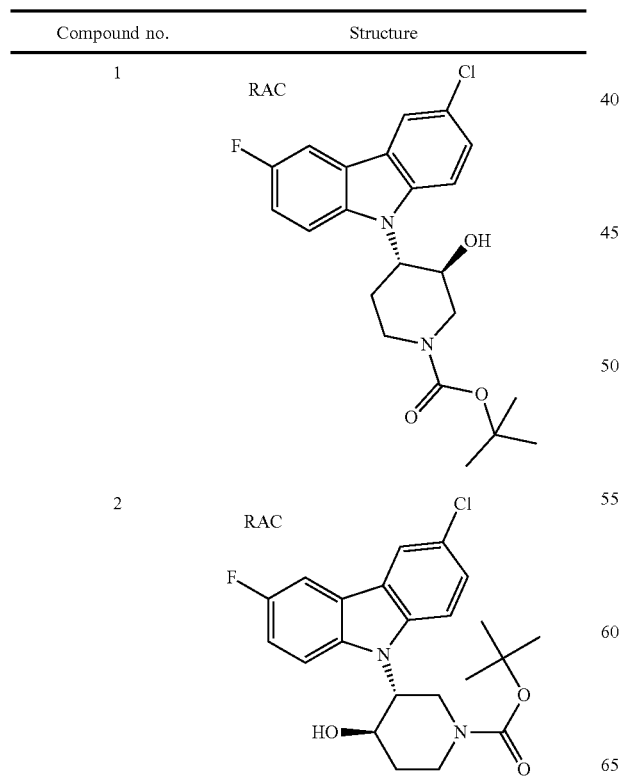

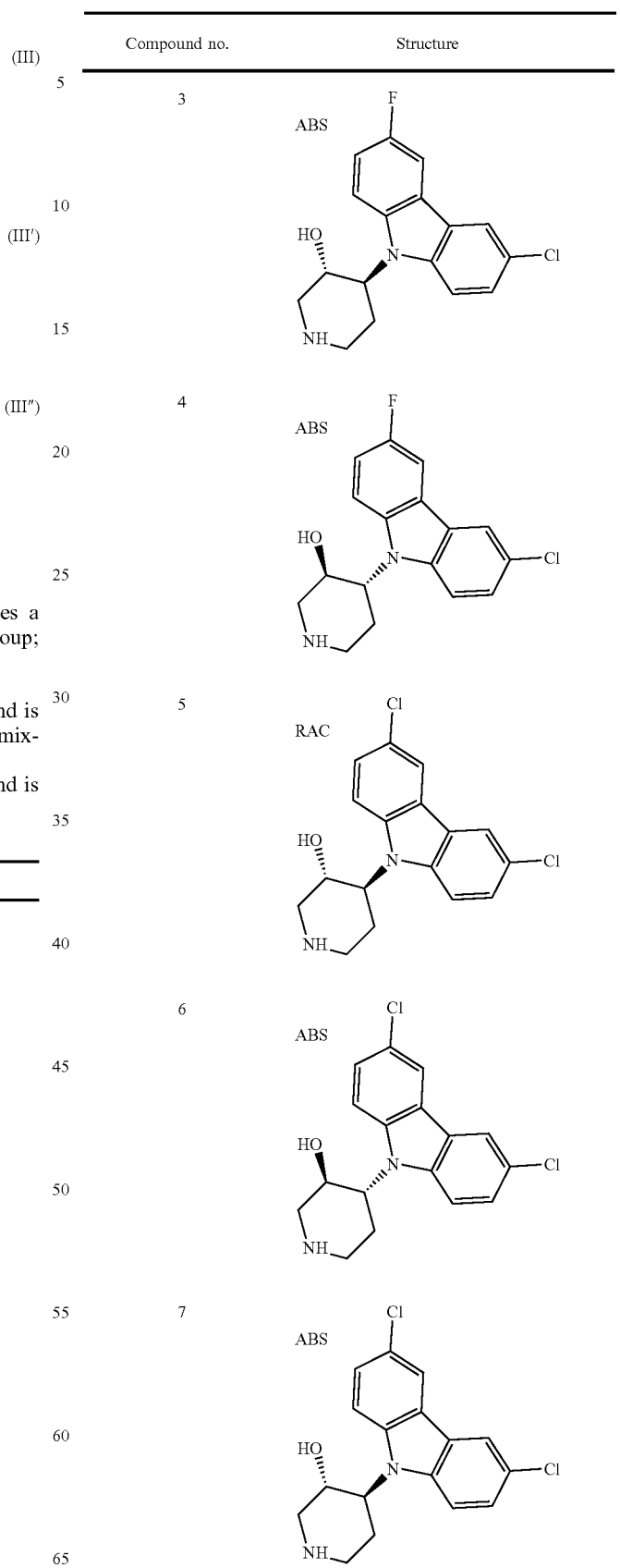

-continued

| Compound no. | Structure |
|---|---|
| 8 | RAC, 3,6-dichlorocarbazole with (3-hydroxypiperidin-4-yl) substituent on N |
| 9 | ABS, 3,6-difluorocarbazole with (3-hydroxypiperidin-4-yl) substituent on N |
| 10 | ABS, 3,6-difluorocarbazole with (3-hydroxypiperidin-4-yl) substituent on N (opposite enantiomer) |
| 14 | RAC, 3,6-dichlorocarbazole N-linked to 3-(1-cyclohexylpiperidin-4-ol)yl |
| 15 | ABS, carbazole N-linked to (3-hydroxypiperidin-4-yl) |

-continued

| Compound no. | Structure |
|---|---|
| 16 | ABS, carbazole N-linked to (3-hydroxypiperidin-4-yl) |
| 17 | ABS, α-carboline N-linked to (3-hydroxypiperidin-4-yl) |
| 18 | ABS, α-carboline N-linked to (3-hydroxypiperidin-4-yl) |
| 19 | ABS, dichloro-α-carboline N-linked to (3-hydroxypiperidin-4-yl) |
| 20 | ABS, dichloro-α-carboline N-linked to (3-hydroxypiperidin-4-yl) |

| Compound no. | Structure |
|---|---|
| 21 | 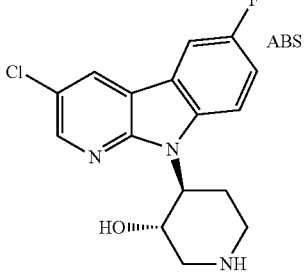 |
| 22 | 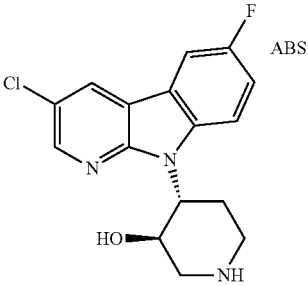 |
| 23 | 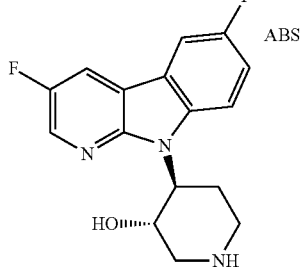 |
| 24 | 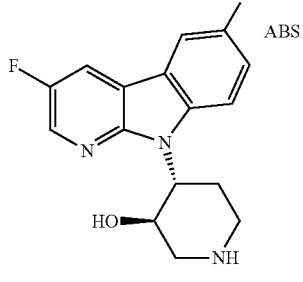 |
| 25 | 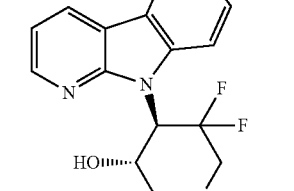 |
| 26 | 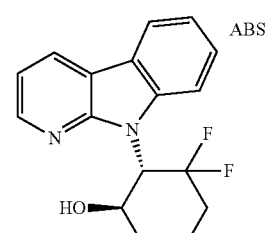 |
| 27 | 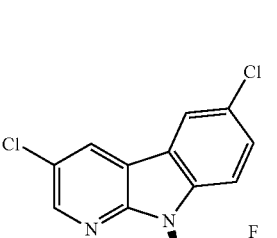 |
| 28 | 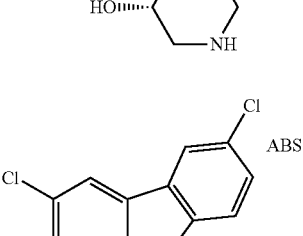 |
| 29 | 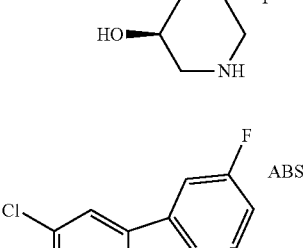 |
| 30 | 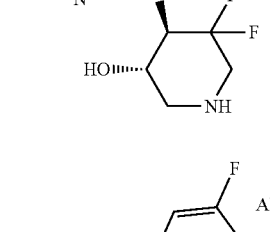 |

| Compound no. | Structure |
|---|---|
| 31 | 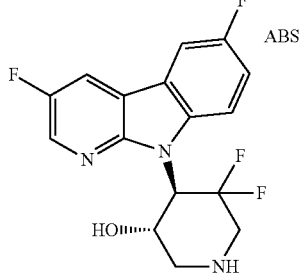 |
| 32 | 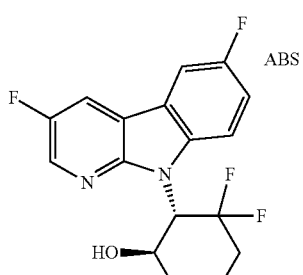 |
| 33 | 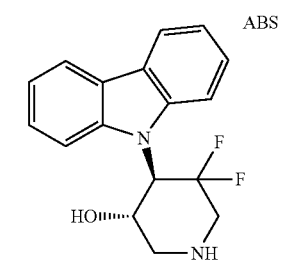 |
| 34 | 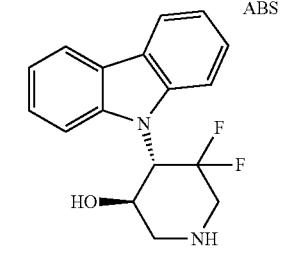 |
| 35 | 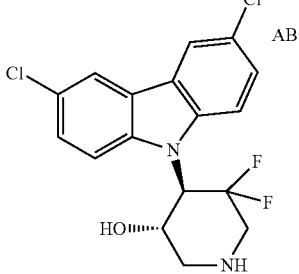 |
| 36 | 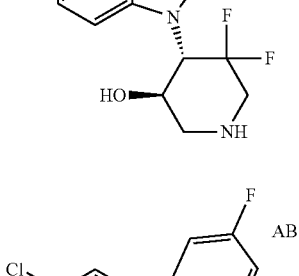 |
| 37 | 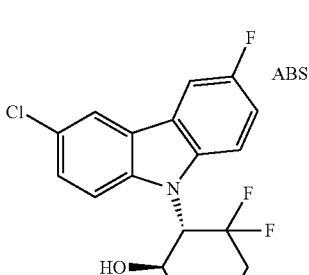 |
| 38 | 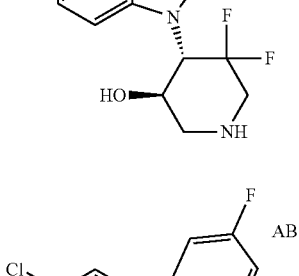 |
| 39 | 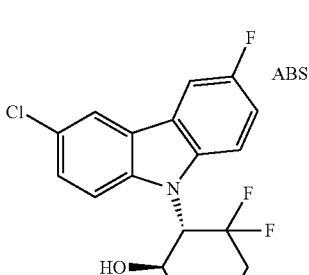 |

-continued
| Compound no. | Structure |
|---|---|
| 40 | 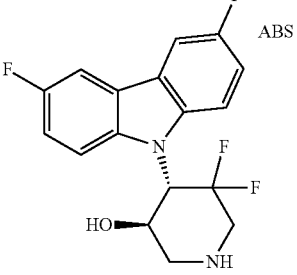 |
| 48 | |
| 56 | |
| 61 | |
| 67 | 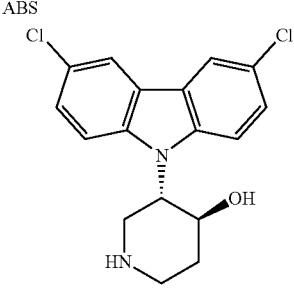 [SMILES: "ABS" ; O[C@H]1CCNC[C@@H]1n1c2ccc(Cl)cc2c2cc(Cl)ccc21] |
| 69 | 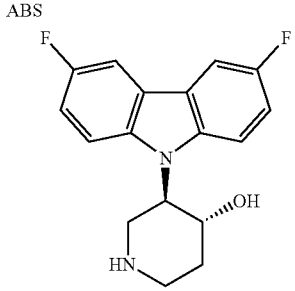 [SMILES: "ABS" ; O[C@@H]1CCNC[C@H]1n1c2ccc(F)cc2c2cc(F)ccc21] |
-continued
| Compound no. | Structure |
|---|---|
| 70 | 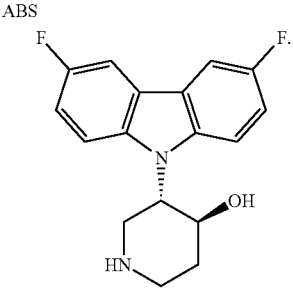 [SMILES: "ABS" ; O[C@H]1CCNC[C@@H]1n1c2ccc(F)cc2c2cc(F)ccc21] |
15. The compound of claim 1, which is a compound of formula 6:
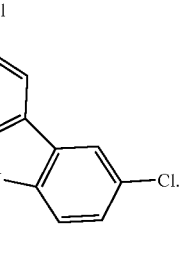
16. The compound of claim 15, which exhibits in vivo efficacy against *P falciparum* PF3D/$^{0087/N9}$.
* * * * *